United States Patent
Ben-Haim et al.

(10) Patent No.: US 11,622,713 B2
(45) Date of Patent: Apr. 11, 2023

(54) ESTIMATORS FOR ABLATION EFFECTIVENESS

(71) Applicant: Navix International Limited, Road Town (VG)

(72) Inventors: Shlomo Ben-Haim, Milan (IT); Yizhaq Shmayahu, Ramat-HaSharon (IL); Yitzhack Schwartz, Haifa (IL); Haim Rodriguez, Tel-Mond (IL); Eli Dichterman, Haifa (IL); Zalman Ibragimov, Rehovot (IL); Yaara Yarden, Jerusalem (IL)

(73) Assignee: Navix International Limited, Road Town (VG)

( * ) Notice: Subject to any disclaimer, the term of this patent is extended or adjusted under 35 U.S.C. 154(b) by 580 days.

(21) Appl. No.: 16/349,999

(22) PCT Filed: Nov. 16, 2017

(86) PCT No.: PCT/IB2017/057186
§ 371 (c)(1),
(2) Date: May 15, 2019

(87) PCT Pub. No.: WO2018/092071
PCT Pub. Date: May 24, 2018

(65) Prior Publication Data
US 2020/0060757 A1    Feb. 27, 2020

Related U.S. Application Data

(60) Provisional application No. 62/445,380, filed on Jan. 12, 2017, provisional application No. 62/445,377, (Continued)

(51) Int. Cl.
*A61B 18/00* (2006.01)
*A61B 34/10* (2016.01)
(Continued)

(52) U.S. Cl.
CPC .......... *A61B 5/4848* (2013.01); *A61B 5/0538* (2013.01); *A61B 5/4878* (2013.01); (Continued)

(58) Field of Classification Search
CPC .......... A61B 2018/00351; A61B 2018/00357; A61B 2018/00363; A61B 2018/00369; (Continued)

(56) References Cited

U.S. PATENT DOCUMENTS

| | | |
|---|---|---|
| 4,917,097 A | 4/1990 | Proudian et al. |
| 5,553,611 A | 9/1996 | Budd et al. |

(Continued)

FOREIGN PATENT DOCUMENTS

| | | |
|---|---|---|
| CA | 2237992 | 3/1998 |
| CN | 102440775 | 5/2012 |

(Continued)

OTHER PUBLICATIONS

Communication Relating to the Results of the Partial International Search dated Aug. 22, 2016 From the International Searching Authority Re. Application No. PCT/IB2016/052686.
(Continued)

*Primary Examiner* — Eun Hwa Kim

(57) ABSTRACT

Methods for estimating of the effectiveness of catheter ablation procedures to form lesions. Lesion effectiveness parameters are received, and effectiveness of a corresponding ablation (optionally planned, current, and/or already performed) is estimated. The estimating is based on use by computer circuitry of an estimator constructed based on observed associations between previously analyzed lesion effectiveness parameters, and observed lesion effectiveness. The estimator is used by application to the received lesion effectiveness parameters.

33 Claims, 26 Drawing Sheets

Related U.S. Application Data filed on Jan. 12, 2017, provisional application No. 62/422,748, filed on Nov. 16, 2016.

(51) Int. Cl.
*A61B 34/20* (2016.01)
*A61B 5/00* (2006.01)
*G06N 20/00* (2019.01)
*A61B 18/14* (2006.01)
*A61B 5/0538* (2021.01)
*A61B 34/00* (2016.01)

(52) U.S. Cl.
CPC .......... *A61B 18/1492* (2013.01); *A61B 34/10* (2016.02); *A61B 34/20* (2016.02); *G06N 20/00* (2019.01); *A61B 5/743* (2013.01); *A61B 34/25* (2016.02); *A61B 2018/00351* (2013.01); *A61B 2018/00577* (2013.01); *A61B 2018/00773* (2013.01); *A61B 2018/00779* (2013.01); *A61B 2018/00791* (2013.01); *A61B 2018/00875* (2013.01); *A61B 2018/00886* (2013.01); *A61B 2034/101* (2016.02)

(58) Field of Classification Search
CPC ........... A61B 2018/00375; A61B 2018/00386; A61B 2018/00577; A61B 5/4848; A61B 34/10; A61B 2034/101
See application file for complete search history.

(56) References Cited

U.S. PATENT DOCUMENTS

| | | |
|---|---|---|
| 5,598,848 A | 2/1997 | Swanson et al. |
| 5,662,108 A | 9/1997 | Budd et al. |
| 5,697,377 A | 12/1997 | Wittkampf |
| 5,724,978 A | 3/1998 | Tenhoff |
| 5,983,126 A | 11/1999 | Wittkampf |
| 6,019,725 A | 2/2000 | Vesely et al. |
| 6,038,468 A | 3/2000 | Rex |
| 6,217,574 B1 | 4/2001 | Webster |
| 6,240,307 B1 | 5/2001 | Beatty et al. |
| 6,266,552 B1 | 7/2001 | Slettenmark |
| 6,301,496 B1 | 10/2001 | Reisfeld |
| 6,317,621 B1 | 11/2001 | Graumann et al. |
| 6,322,558 B1 | 11/2001 | Taylor et al. |
| 6,423,057 B1 | 7/2002 | He et al. |
| 6,515,657 B1 | 2/2003 | Zanelli |
| 6,640,119 B1 | 10/2003 | Budd et al. |
| 6,728,562 B1 | 4/2004 | Budd et al. |
| 6,826,420 B1 | 11/2004 | Beatty et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,989,010 B2 | 1/2006 | Francischelli et al. |
| 6,990,370 B1 | 1/2006 | Beatty et al. |
| 7,001,383 B2 | 2/2006 | Keidar |
| 7,146,210 B2 | 12/2006 | Palti |
| 7,187,973 B2 | 3/2007 | Hauck |
| 7,189,208 B1 | 3/2007 | Beatty et al. |
| 7,306,593 B2 * | 12/2007 | Keidar .................. A61B 90/92 606/41 |
| 7,881,769 B2 | 2/2011 | Sobe |
| 7,996,060 B2 | 8/2011 | Trofimov et al. |
| 8,160,690 B2 | 4/2012 | Wilfley et al. |
| 8,403,925 B2 | 3/2013 | Miller et al. |
| 8,454,589 B2 | 6/2013 | Deno et al. |
| 8,556,888 B2 | 10/2013 | Nields et al. |
| 9,101,333 B2 | 8/2015 | Schwartz |
| 9,259,290 B2 | 2/2016 | Jenkins et al. |
| 9,271,782 B2 | 3/2016 | Paul et al. |
| 9,283,051 B2 | 3/2016 | Garcia et al. |
| 9,636,164 B2 | 5/2017 | Panescu et al. |
| 9,743,854 B2 | 8/2017 | Stewart et al. |
| 9,757,182 B2 | 9/2017 | Bustan et al. |
| 9,757,191 B2 | 9/2017 | Avitall et al. |
| 9,955,946 B2 | 5/2018 | Miller et al. |
| 9,980,653 B2 | 5/2018 | Lichtenstein et al. |
| 10,292,588 B2 | 5/2019 | Ben-Haim |
| 2002/0068931 A1 | 6/2002 | Wong et al. |
| 2003/0074011 A1 | 4/2003 | Gilboa et al. |
| 2003/0220636 A1 | 11/2003 | Bowman et al. |
| 2004/0039278 A1 | 2/2004 | Wacker et al. |
| 2004/0044279 A1 | 3/2004 | Lewin et al. |
| 2004/0097805 A1 | 5/2004 | Verard et al. |
| 2004/0147920 A1 | 7/2004 | Keidar |
| 2004/0176804 A1 | 9/2004 | Palti |
| 2005/0015006 A1 | 1/2005 | Mitschke et al. |
| 2005/0033164 A1 | 2/2005 | Yatsuo et al. |
| 2005/0054913 A1 | 3/2005 | Duerk et al. |
| 2005/0054918 A1 | 3/2005 | Sra |
| 2005/0058328 A1 | 3/2005 | Moreau-Gobard |
| 2005/0245814 A1 | 11/2005 | Anderson et al. |
| 2006/0015165 A1 | 1/2006 | Bertolero et al. |
| 2006/0089552 A1 | 4/2006 | Goldbach |
| 2006/0241401 A1 | 10/2006 | Govari et al. |
| 2007/0043296 A1 | 2/2007 | Schwartz |
| 2007/0049915 A1 | 3/2007 | Haemmerich et al. |
| 2007/0106289 A1 | 5/2007 | O'Sullivan |
| 2007/0167706 A1 | 7/2007 | Boese et al. |
| 2007/0167726 A1 | 7/2007 | Unal et al. |
| 2008/0114235 A1 | 5/2008 | Unal et al. |
| 2008/0118135 A1 | 5/2008 | Averbuch et al. |
| 2008/0125775 A1 | 5/2008 | Morris |
| 2008/0177175 A1 | 7/2008 | Mottola et al. |
| 2008/0183070 A1 | 7/2008 | Unal et al. |
| 2008/0190438 A1 | 8/2008 | Harlev et al. |
| 2008/0208031 A1 | 8/2008 | Kurpad et al. |
| 2008/0221425 A1 | 9/2008 | Olson et al. |
| 2008/0230705 A1 | 9/2008 | Rousso et al. |
| 2008/0275440 A1 | 11/2008 | Kratoska et al. |
| 2008/0275465 A1 | 11/2008 | Paul et al. |
| 2008/0281319 A1 | 11/2008 | Paul et al. |
| 2009/0010519 A1 | 1/2009 | Wakai et al. |
| 2009/0015818 A1 | 1/2009 | Ikeda et al. |
| 2009/0076499 A1 | 3/2009 | Azure |
| 2009/0148012 A1 | 6/2009 | Altmann et al. |
| 2009/0171274 A1 | 7/2009 | Harlev et al. |
| 2009/0221908 A1 | 9/2009 | Glossop |
| 2009/0225077 A1 | 9/2009 | Sudarsky et al. |
| 2009/0262109 A1 | 10/2009 | Markowitz et al. |
| 2009/0275828 A1 | 11/2009 | Shachar et al. |
| 2009/0281566 A1 | 11/2009 | Edwards et al. |
| 2009/0306643 A1 | 12/2009 | Pappone et al. |
| 2010/0063400 A1 | 3/2010 | Hall et al. |
| 2010/0069921 A1 | 3/2010 | Miller et al. |
| 2010/0185087 A1 | 7/2010 | Nields et al. |
| 2010/0217116 A1 | 8/2010 | Eck et al. |
| 2010/0249579 A1 | 9/2010 | Starks |
| 2010/0274239 A1 | 10/2010 | Paul et al. |
| 2010/0029882 A1 | 11/2010 | Leo et al. |
| 2010/0283484 A1 | 11/2010 | Cohen et al. |
| 2010/0312094 A1 | 12/2010 | Guttman et al. |
| 2010/0312096 A1 | 12/2010 | Guttman et al. |
| 2011/0028967 A1 | 2/2011 | Rollins et al. |
| 2011/0106221 A1 | 5/2011 | Neal, II et al. |
| 2011/0144524 A1 | 6/2011 | Fish et al. |
| 2011/0152853 A1 | 6/2011 | Manley et al. |
| 2011/0230758 A1 | 9/2011 | Eichler |
| 2011/0282186 A1 | 11/2011 | Harlev et al. |
| 2011/0306867 A1 | 12/2011 | Gopinathan et al. |
| 2012/0059249 A1 | 3/2012 | Verard et al. |
| 2012/0078129 A1 | 3/2012 | Bailin |
| 2012/0109115 A1 | 5/2012 | Condie et al. |
| 2012/0116210 A1 | 5/2012 | Zino |
| 2012/0123250 A1 | 5/2012 | Pang et al. |
| 2012/0150046 A1 | 6/2012 | Warson et al. |
| 2012/0172724 A1 | 7/2012 | Hill et al. |
| 2012/0173217 A1 | 7/2012 | Heimbecher |
| 2012/0197243 A1 | 8/2012 | Sherman et al. |
| 2012/0209260 A1 | 8/2012 | Lambert et al. |
| 2012/0238866 A1 | 9/2012 | Wang et al. |
| 2013/0137980 A1 | 5/2013 | Waters et al. |

(56) References Cited

U.S. PATENT DOCUMENTS

| | | | |
|---|---|---|---|
| 2013/0184700 A1 | 7/2013 | Dalal et al. | |
| 2013/0272593 A1 | 10/2013 | Lee et al. | |
| 2013/0310673 A1 | 11/2013 | Govari et al. | |
| 2014/0024911 A1 | 1/2014 | Harlev et al. | |
| 2014/0051959 A1* | 2/2014 | Gliner | A61B 5/7267 606/41 |
| 2014/0088943 A1 | 3/2014 | Trayanova et al. | |
| 2014/0180273 A1* | 6/2014 | Nair | A61B 8/0891 606/34 |
| 2014/0187949 A1 | 7/2014 | Zhao et al. | |
| 2014/0243641 A1 | 8/2014 | Boveja et al. | |
| 2014/0243813 A1 | 8/2014 | Paul et al. | |
| 2014/0275991 A1 | 9/2014 | Potter et al. | |
| 2014/0279754 A1 | 9/2014 | Barsoum et al. | |
| 2014/0330111 A1 | 11/2014 | Lichtenstein et al. | |
| 2015/0080762 A1 | 3/2015 | Kassab et al. | |
| 2015/0099942 A1 | 4/2015 | Edouard | |
| 2015/0099979 A1* | 4/2015 | Caves | A61B 5/0071 600/407 |
| 2015/0141978 A1 | 5/2015 | Subramaniam et al. | |
| 2015/0147382 A1 | 6/2015 | Avitall et al. | |
| 2015/0196202 A1 | 7/2015 | Mercader et al. | |
| 2015/0223757 A1 | 8/2015 | Werneth et al. | |
| 2015/0230863 A1 | 8/2015 | Youngquist et al. | |
| 2015/0254422 A1 | 9/2015 | Avisar | |
| 2016/0022375 A1 | 1/2016 | Blake et al. | |
| 2016/0066977 A1 | 3/2016 | Neal, II et al. | |
| 2016/0095651 A1 | 4/2016 | Deno et al. | |
| 2016/0095653 A1* | 4/2016 | Lambert | A61B 18/1492 606/41 |
| 2016/0242667 A1 | 8/2016 | Fay et al. | |
| 2016/0249989 A1 | 9/2016 | DeVam et al. | |
| 2016/0270683 A1 | 9/2016 | Grass et al. | |
| 2017/0014181 A1 | 1/2017 | Bar-Tal et al. | |
| 2017/0027460 A1 | 2/2017 | Shimada et al. | |
| 2017/0071664 A1 | 3/2017 | Lim | |
| 2017/0009805 A1 | 4/2017 | Voth | |
| 2017/0156792 A1 | 6/2017 | Ziv-Ari et al. | |
| 2017/0263021 A1 | 9/2017 | Ben Haim | |
| 2017/0281281 A1 | 10/2017 | He et al. | |
| 2018/0116751 A1 | 5/2018 | Schwartz et al. | |
| 2018/0125575 A1 | 5/2018 | Schwartz et al. | |
| 2018/0153437 A1 | 6/2018 | Schwartz et al. | |
| 2018/0325597 A1 | 11/2018 | Schwartz et al. | |
| 2019/0254564 A1 | 8/2019 | Schwartz et al. | |
| 2019/0328275 A1 | 10/2019 | Shmayahu et al. | |
| 2019/0328458 A1 | 10/2019 | Shmayahu et al. | |
| 2019/0336035 A1 | 11/2019 | Dichterman et al. | |
| 2019/0340837 A1 | 11/2019 | Shmayahu et al. | |
| 2020/0022649 A1 | 1/2020 | Rodriguez et al. | |
| 2020/0315709 A1 | 10/2020 | Shmayahu et al. | |
| 2021/0153933 A1 | 5/2021 | Schwartz et al. | |

FOREIGN PATENT DOCUMENTS

| | | |
|---|---|---|
| CN | 103209654 | 7/2013 |
| CN | 103379873 | 10/2013 |
| CN | 102421356 | 9/2014 |
| CN | 104605928 | 5/2015 |
| EP | 0974936 | 1/2000 |
| EP | 1472975 | 11/2004 |
| EP | 1504713 | 2/2005 |
| EP | 1726268 | 11/2006 |
| EP | 1767166 | 3/2007 |
| EP | 1853162 | 11/2007 |
| EP | 1943974 | 7/2008 |
| EP | 2075763 | 7/2009 |
| EP | 2248480 | 11/2010 |
| EP | 2712543 | 4/2014 |
| EP | 2777584 | 9/2014 |
| HR | P20131208 | 3/2014 |
| JP | 2001-340336 | 12/2001 |
| JP | 2005-199072 | 7/2005 |
| JP | 2009-518130 | 5/2009 |
| JP | 2014-533130 | 12/2014 |
| JP | 2015-503365 | 2/2015 |
| WO | WO 2007/067628 | 6/1997 |
| WO | WO 97/29682 | 8/1997 |
| WO | WO 98/01069 | 1/1998 |
| WO | WO 2007/067628 | 6/2007 |
| WO | WO 2008/097767 | 8/2008 |
| WO | WO 2008/104914 | 9/2008 |
| WO | WO 2010/102794 | 9/2010 |
| WO | WO 2010/129095 | 11/2010 |
| WO | WO 2011/142931 | 11/2011 |
| WO | WO 2012/092016 | 7/2012 |
| WO | WO 2013/052590 | 4/2013 |
| WO | WO 2013/096916 | 6/2013 |
| WO | WO 2013/192598 | 12/2013 |
| WO | WO 2014/118535 | 8/2014 |
| WO | WO 2014/182822 | 11/2014 |
| WO | WO 2016/038499 | 3/2016 |
| WO | WO 2016/088084 | 6/2016 |
| WO | WO 2016/135584 | 9/2016 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |
| WO | WO 2018/078540 | 5/2018 |
| WO | WO 2018/092059 | 5/2018 |
| WO | WO 2018/092062 | 5/2018 |
| WO | WO 2018/092063 | 5/2018 |
| WO | WO 2018/092070 | 5/2018 |
| WO | WO 2018/092071 | 5/2018 |
| WO | WO 2018/130974 | 7/2018 |
| WO | WO 2018/130976 | 7/2018 |
| WO | WO 2018/130981 | 7/2018 |
| WO | WO 2018/134747 | 7/2018 |
| WO | WO 2018/146613 | 8/2018 |
| WO | WO 2018/207128 | 11/2018 |
| WO | WO 2019/034944 | 2/2019 |
| WO | WO 2019/035023 | 2/2019 |
| WO | WO 2019/111180 | 6/2019 |
| WO | WO 2019/215574 | 11/2019 |

OTHER PUBLICATIONS

Communication Relating to the Results of the Partial International Search dated Aug. 22, 2016 From the International Searching Authority Re. Application No. PCT/IB2016/052688.

Communication Relating to the Results of the Partial International Search dated Aug. 25, 2016 From the International Searching Authority Re. Application No. PCT/IB2016/052692.

Communication Relating to the Results of the Partial International Search dated Aug. 26, 2016 From the International Searching Authority Re. Application No. PCT/IB2016/052687.

International Preliminary Report on Patentability dated May 9, 2019 From the International Bureau of WIPO Re. Application No. PCT/IB2017/056616. (8 Pages).

International Preliminary Report on Patentability dated Nov. 23, 2017 From the International Bureau of WIPO Re. Application No. PCT/IB2016/052686. (11 Pages).

International Preliminary Report on Patentability dated Nov. 23, 2017 From the International Bureau of WIPO Re. Application No. PCT/IB2016/052687. (10 Pages).

International Preliminary Report on Patentability dated Nov. 23, 2017 From the International Bureau of WIPO Re. Application No. PCT/IB2016/052688. (9 Pages).

International Preliminary Report on Patentability dated Nov. 23, 2017 From the International Bureau of WIPO Re. Application No. PCT/IB2016/052690. (9 Pages).

International Preliminary Report on Patentability dated Nov. 23, 2017 From the International Bureau of WIPO Re. Application No. PCT/IB2016/052692. (13 Pages).

International Preliminary Report on Patentability dated May 31, 2019 From the International Bureau of WIPO Re. Application No. PCT/IB2017/057186. (13 Pages).

(56) References Cited

OTHER PUBLICATIONS

International Search Report and the Written Opinion dated Feb. 1, 2018 From the International Searching Authority Re. Application No. PCT/IB2017/056616. (14 Pages).
International Search Report and the Written Opinion dated Jan. 2, 2019 From the International Searching Authority Re. Application No. PCT/TB2018/056158. (16 Pages).
International Search Report and the Written Opinion dated Jan. 3, 2017 From the International Searching Authority Re. Application No. PCT/IB2016/052688. (14 Pages).
International Search Report and the Written Opinion dated May 3, 2018 From the International Searching Authority Re. Application No. PCT/IB2017/057185. (18 Pages).
International Search Report and the Written Opinion dated Jun. 6, 2018 From the International Searching Authority Re. Application No. PCT/IB2018/050201. (24 Pages).
International Search Report and the Written Opinion dated May 9, 2018 From the International Searching Authority Re. Application No. PCT/IB2018/050192. (16 Pages).
International Search Report and the Written Opinion dated Oct. 12, 2016 From the International Searching Authority Re. Application No. PCT/IB2016/052686.
International Search Report and the Written Opinion dated Aug. 13, 2018 From the International Searching Authority Re. Application No. PCT/IB2018/053258. (15 Pages).
International Search Report and the Written Opinion dated Apr. 14, 2019 From the International Searching Authority Re. Application No. PCT/IB2018/059672. (49 Pages).
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written dated dated Oct. 21, 2016 From the International Searching Authority Re. Application No. PCT/IB2016/052687. (16 Pages).
International Search Report and the Written Opinion dated Feb. 22, 2018 From the International Searching Authority Re. Application No. PCT/IB2017/057169. (14 Pages).
International Search Report and the Written Opinion dated Feb. 22, 2018 From the International Searching Authority Re. Application No. PCT/IB2017/057175. (15 Pages).
International Search Report and the Written Opinion dated Feb. 22, 2018 From the International Searching Authority Re. Application No. PCT/IB2017/057176. (15 Pages).
International Search Report and the Written Opinion dated Aug. 25, 2016 From the International Searching Authority Re. Application No. PCT/IB2016/052690.
International Search Report and the Written Opinion dated Apr. 30, 2018 From the International Searching Authority Re. Application No. PCT/IB2017/057186. (22 Pages).
International Search Report and the Written Opinion dated Apr. 30, 2018 From the International Searching Authority Re. Application No. PCT/IB2018/050195. (16 Pages).
International Search Report and the Written Opinion dated Nov. 30, 2018 From the International Searching Authority Re. Application No. PCT/IB2018/055344. (15 Pages).
Invitation to Pay Additional Fees and Communication Related to the Results of the Partial International Search and the Provisional Opinion dated Feb. 22, 2018 From the International Searching Authority Re. Application No. PCT/IB2017/057186. (12 Pages).
Invitation to Pay Additional Fees, Communication Relating to the Results of the Partial International Search and the Provisional Opinion dated Mar. 5, 2018 From the International Searching Authority Re. Application No. PCT/IB2017/057185. (13 Pages).
Invitation to Pay Additional Fees, Communication Relating to the Results of the Partial International Search and the Provisional Opinion dated Apr. 25, 2018 From the International Searching Authority Re. Application No. PCT/TB2018/050201. (14 Pages).

Notice Of Allowance dated Dec. 26, 2018 From the US Patent and Trademark Office Re. U.S. Appl. No. 15/572,815. (8 pages).
Official Action dated Aug. 30, 2018 From the US Patent and Trademark Office Re. U.S. Appl. No. 15/572,815. (22 pages).
Ahn et al. "Height-Based Deformation and Ray Supersampling for Colon Unfolding", ICAT'06 Proceedings of the 16th International Conference on Advances in Artificial Reality and Tele-Existence, Lecture Notes in Computer Science, XP047402101, Hangzhou, China, Nov. 29-Dec. 1, 2006, p. 1098-1107, Nov. 29, 2006. Sections 3.1, 3.3, 5, Figs.2, 4, 5.
Anter et al. "Evaluation of a Novel High-Resolution Mapping Technology for Ablation of Recurrent Scar-Related Atrial Tachycardias," Heart Rhythm, 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Bartroli et al. "Nonlinear Virtual Colon Unfolding", Proceedings of the IEEE Conference on Visualization '01, VIS '01, XP031385694, San Diego, CA, USA, Oct. 21-26, 2001, p. 411-420, Oct. 21, 2001. Sections 4, 4.1, 4.2, 5.1, 7, Figs.1, 7a, 7b, 10.
Black-Maier et al. "Risk of Atrioesophageal Fistula Formation With Contact-Force Sensing Catheters", HeartRhythm, 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Canpolat et al. "Relationship Between Vitamin D Level and Left Atrial Fibrosis in Patients With Lone Paroxysmal Atrial Fibrillation Undergoing Cryoballoon-Based Catheter Ablation", Journal of Cardiology, 6991): 16-23, Published Online Aug. 21, 2016.
Caspi et al. "Modeling of Arrhythmogenic Right Ventricular Cardiomyopathy With Human Induced Pluripotent Stem Cells", Circulation: Cardiovscular Genetics, 6(6): 557-568, Published Online Nov. 7, 2013.
Cerit et al. "Association of Pre-Ablation Level of Vitamin D With Atrial Fibrillation Recurrence After Catheter Ablation", Europace, 19(9): 1586, Sep. 1, 2017.
Chierchia et al. "An Initial Clinical Experience With A Novel Microwave Radiometry Sensing Technology Used in Irrigated RF Ablation for Flutter", Academic Hospital Brussels, Belgium, 1 P. Jan. 1, 2011.
Crospon "Esophageal Treatment by Esoflip®", Crospon, Product Sheet, 4 P., 2017.
Crospon "Flip® Technology", Crospon, Product Sheet, 6 P., 2017.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PV1 Lines to Incorporate Non-PV Targets Identified by Pre-Ablation Mapping with the AcQMap System: Update on the Uncover-AF Trial," EP Lab Digest, 17(5), May 2017, 5 pages.

(56) References Cited

OTHER PUBLICATIONS

Hilbert et al. "An Integrative Approach to Slow Pathway Modulation in AVNRT Using A Novel Ultra High-Density Electroanatomical Mapping System", Clinical Research in Cardiology, XP035518036, 104(8): 697-699, Published Online Mar. 31, 2015.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA. May 9-12, 2012, Session: Role of Autonomies in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # PO3-53, May 10, 2012.
Jiang et al. "Association of Pre-Ablation Level of Potential Blood Markers With Atrial Fibrillation Recurrence After Catheter Ablation: A Meta-Analysis", Europace, 19(3): 392-400, Mar. 1, 2017.
Karim et al. "Surface Flattening of the Human Left Atrium and Proof-of-Concept Clinical Applications", Computerized Medical Imaging and Graphics, 38(4): 251-266, Jun. 2014.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
McDowell et al. "Virtual Electrophysiological Study of Atrial Fibrillation in Fibrotic Remodeling", PLOS One, 10(2): e117110-1-e117110-16, Published Online Feb. 18, 2015.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Ranjan et al. "Gaps in the Ablation Line as A Potential Cause of Recovery From Electrical Isolation and Their Visualization Using MRI", Circulation: Arrhythmia and Electrophysiology, XP055452459, 4(3): 279-286, Published Online Apr. 14, 2011.
Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.
Shoemaker et al. "Common Genetic Variants and Response to Atrial Fibrillation Ablation", Circulation: Arrhythmia and Electrophysiology, 8(2): 296-302, Pubhshed Online Feb. 14, 2015.
St. Jude Medical "Cardiac Mapping System/ECG. NSite™ NavX™", St. Jude Medical, Products Sheet, 22 P., 2017.
Ueberham et al. "Genetic ACE I/D Polymorphism and Recurrence of Atrial Fibrillation After Catheter Ablation", Circulation: Arrhythmia and Electrophysiology, 6(4): 732-737, Published Online Jul. 22, 2013.
Vandekerckhove et al. "Flutter Ablation With an Irrigated Catheter Using Microwave Radiometry Sensing Technology: First Report in Men", Sint Jan Hospital, Department of Cardiology, Bruges, Belgium, 1 P., Jan. 1, 2011.
Wang et al. "Association of the Angiotensinogen M235T Polymorphism With Recurrence After Catheter Ablation of Acquired Atrial Fibrillation", Journal of the Renin-Angiotensin-Aldosterone System. 16(4): 888-897, Published Online Aug. 3, 2015.
Wang et al. "Colon Unraveling Based on Electrical Field: Recent Progress and Further Work", Proceedings of the SPIE 3660 Medical Imaging '99: Physiology and Function From Multidimensional Images, San Diego, CA, USA, Feb. 1999, XP055479173, 3660: 125-133, May 20, 1999. Abstract, Sections 1, 2.2, 2.3, Figs.2, 3.
Wang et al. "Microwave Radiometric Thermoetry and Its Potential Applicability to Ablative Therapy", Journal of Interventional Cardiac Electrophysiology, 4(1): 295-300, Feb. 2000.
Wittkampf et al. "LocaLisa: New Technique for Real-Time 3-Dimensional Localization of Regular Intracardiac Electrodes", Circulation, 99(10): 1312-1317, Mar. 16, 1999.
Zhong et al. "On the Accuracy of CartoMerge for Guiding Posterior Left Atrial Ablation in Man", Heart Rhythm, 4(5): 595-602, Published Online Feb. 9, 2007.
International Preliminary Report on Patentability dated Jul. 25, 2019 From the International Bureau of WIPO Re. Application No. PCT/IB2018/050195. (9 Pages).
Notification of Office Action and Search Report dated Mar. 24, 2021 From the State Intellectual Property Office of the People's Republic of China Re. Application No. 201680026934.X. (9 Pages).
International Search Report and the Written Opinion dated Sep. 25, 2018 From the International Searching Authority Re. Application No. PCT/IB2018/050784. (18 Pages).
Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).
Boston Scientific "Rhythmia™ Mapping System: Rhythmia Dispossables Product Information: Intellamap Orion™ High Resolution Mapping Catheter", Boston Scientifc, 2 P., Sep. 2015.
Communication Pursuant to Article 94(3) EPC dated Sep. 4, 2020 From the European Patent Office Re. Application No. 16725589.2. (8 Pages).
Official Action dated Mar. 5, 2020 From the US Patent and Trademark Office Re. U.S. Appl. No. 15/573,493. (21 pages).
Communication Pursuant to Article 94(3) EPC dated Sep. 25, 2020 From the European Patent Office Re. Application No. 16726181.7. (5 Pages).
Decision of Refusal dated Oct. 20, 2020 From the Japan Patent Office Re. Application No. 2017-558704 and Its Translation Into English. (6 Pages).
Final Official Action dated Jul. 1, 2020 from the US Patent and Trademark Office Re. U.S. Appl. No. 15/570,341. (24 pages).
Final Official Action dated Jun. 22, 2020 from the US Patent and Trademark Office Re. U.S. Appl. No. 15/573,491. (14 pages).
International Preliminary Report on Patentability dated Jun. 18, 2020 From the International Bureau of WIPO Re. Application No. PCT/IB2018/059672. (8 Pages).
International Preliminary Report on Patentability dated Nov. 21, 2019 From the International Bureau of WIPO Re. Application No. PCT/IB2018/053258. (8 Pages).
International Preliminary Report on Patentability dated Aug. 22, 2019 From the International Bureau of WIPO Re. Application No. PCT/IB2018/050784. (11 Pages).
International Preliminary Report on Patentability dated Jul. 25, 2019 From the International Bureau of WIPO Re. Application No. PCT/IB2018/050192. (8 Pages).
International Preliminary Report on Patentability dated May 31, 2019 From the International Burau of WIPO Re. Application No. PCT/IB2017/057185. (11 Pages).
International Preliminary Report on Patentability dated May 31, 2019 From the International Bureau of WIPO Re. Application No. PCT/IB2017/057169. (9 Pages).
International Preliminary Report on Patentability dated May 31, 2019 From the International Bureau of WIPO Re. Application No. PCT/IB2017/057175. (9 Pages).
International Preliminary Report on Patentability dated May 31, 2019 From the International Bureau of WIPO Re. Application No. PCT/IB2017/057176. (10 Pages).
Interview Summary dated Dec. 15, 2020 from the US Patent and Trademark Office Re. U.S. Appl. No. 15/570,341. (4 pages).
Interview Summary dated Sep. 29, 2020 from the US Patent and Trademark Office Re. U.S. Appl. No. 15/573,491. (3 pages).

(56) References Cited

OTHER PUBLICATIONS

Notice of Allowance dated Jan. 8, 2021 From the US Patent and Trademark Office Re. U.S. Appl. No. 16/461,384. (37 pages).
Notice of Allowance dated Oct. 22, 2020 From the US Patent and Trademark Office Re. U.S. Appl. No. 15/573,491. (6 Pages).
Notice of Allowance dated Feb. 24, 2021 From the US Patent and Trademark Office Re. U.S. Appl. No. 15/570,341. (8 Pages).
Notice of Allowance dated Mar. 9, 2020 from the US Patent and Trademark Office Re. U.S. Appl. No. 16/349,648. (28 pages).
Notice of Reasons for Refusal dated Mar. 3, 2020 From the Japan Patent Office Re. Application No. 2017-558704 and Its Translation Into English. (14 Pages).
Official Action dated Feb. 6, 2020 From the US Patent and Trademark Office Re. U.S. Appl. No. 15/570,341. (33 pages).
Official Action dated Jan. 8, 2020 From the US Patent and Trademark Office Re. U.S. Appl. No. 15/573,491. (20 pages).
Restriction Official Action dated Jun. 12, 2020 from the US Patent and Trademark Office Re. U.S. Appl. No. 16/461,384. (6 pages).
Third-Party Submission under 37 CFR 1.290 filed on Mar. 2, 2021 From the US Patent and Trademark Office Re. U.S. Appl. No. 16/349,646. (2 Pages).
USPTO Communication dated Mar. 5, 2021 RE Third-Party Submission from the US Patent and Trademark Office Re. U.S. Appl. No. 16/349,646.(2 Pages).
Anselmino et al. "A New Electrophysiology Era: Zero Fluoroscopy", Journal of Cardiovascular Medicine, 14(3): 221-227, Mar. 2013.
Avitall et al. "Novel Dye-Less and Fluoro-Less Approach to Cryoballoon Pulmonary Vein Occlusion Assessment", Heart Rhythm, 14(8): 1241-1246, Aug. 2017.
Bulava et al. "Catheter Ablation of Atrial Fibrillation Using Zero-Fluoroscopy Technique: A Randomized Trial", PACE: Pacing and Clinical Electricophysiology, 38(7): 797-806, Published Online Apr. 16, 2015.
Giaccardi et al. "Near-Zero X-Ray in Arrhythmia Ablation Using A 3-Dimensional Electroanatomic Mapping System: A Multicenter Experience", Heart Rhythm, 13(1): 150-156, Published Online Sep. 1, 2015.
Hou et al. "Fluoroscopy-Free Electrophysiology Study Using 3D Electroanatomic Mapping System: A Case Report and Review of Literature", Journal of Cardiology & Clinical Research, 5(3): 1100-1-1100-4, Mar. 9, 2017.
Koruth et al. "Tissue Temperature Sensing During Irrigated Radiofrequency Ablation: A Novel Strategy to Predict Steam Pops", Heart Rhythm, 33rd Annual Scientific Sessions, Boston, MA, USA, May 9-12, 2012, Presentation Abstract, # AB12-02, May 10, 2012.
Luani et al. "Zero-Fluoroscopy Cryothermal Ablation of Atrioventricular Nodal Reentry Tachycardia Guided by Endovascular and Endocardial Cetheter Visualization Using Intracardia Echocardiography (Ice&ICE Trial)", Journal of Cardiovascular Electrophysiology, 29(1): 160-166, Published Online Oct. 26, 2017.
Macias et al. "A Zero-Fluoroscopy Approach to Cavotricuspid Isthmus Catheter Ablation: Comparative Analysis of Two Electroanatomical Mapping Systems", PACE: Pacing and Clinical Electrophysiology, 37(8): 1029-1037, Published Online Mar. 13, 2014.
O'Brien et al. "Fluoroscopy-Free AF Ablation Using Transesophageal Echocardiography and Electroanatomical Mapping Technology", Journal of Interventional Cardiac Electrophysiology, 50(3): 235-244, Published Online Nov. 14, 2017.
Pinkstone "Needles With Built-In Cameras the Same Width as A Human Hair Capture Ultrasound Images Inside Patients to Help Surgeons Perform Keyhole Surgery", MailOnline, 27 P., Dec. 1, 2017.
Sommer et al. "Safety Profile of Near-Zero Fluoroscopy Atrial Fibrillation Ablation With Non-Fluoroscopic Catheter Visualization: Experience From 1000 Consecutive Procedures", Europace, 20(12): 1952-1958, Published Online Jan. 16, 2016.
Sulkin et al. "Novel Measure of Local Impedance Predicts Catheter-Tissue Contact and Lesion Formation", Circulation: Arrhythmia and Electrophysiology, 11(4): e005831-1-e005831-21, Apr. 2018.
Wang et al. "Ablation of Idiopathic Ventricular Arrhythmia Using Zero-Fluoroscopy Approach With Equivalent Efficacy and Less Fatigue—A Multicenter Comparative Study", Medicine, 96(6): e6080-1-e6080-7, Feb. 2017.
Wannagat et al. "Implemenation of A Near-Zero Fluoroscopy Approach in Interventional Electrophysiology: Impact of Operator Experience", Journal of Interventional Cardiac Electrophysiology, 51(3): 215-220, Published Online Feb. 19, 2018.
Yang et al. "Meta-Analysis of Zero or Near-Zero Fluoroscopy Use During Ablation of Cardiac Arrhythmias", The American Journal of Cardiology, 118(10): 1511-1518, Published Online Aug. 24, 2016.
Notice of Allowance dated Sep. 4, 2020 from the US Patent and Trademark Office Re. U.S. Appl. No. 15/573,493. (14 pages).
Notification Regarding Third-Party Preissuance Submission dated Feb. 10, 2021 From the US Patent and Trademark Office Re. U.S. Appl. No. 16/494,308.(2 Pages).
Third Party IDS Submission under 37 CFR 1.290 filed on Feb. 4, 2021 From the US Patent and Trademark Office Re. U.S. Appl. No. 16/477,204.(2 Pages).
International Search Report and the Written Opinion dated Jun. 7, 2018 From the International Searching Authority Re. Application No. PCT/IB2018/050289. (16 Pages).
Notice of Reasons for Refusal dated Apr. 21, 2020 From the Japan Patent Office Re. Application No. 2017-558702 and Its Translation Into English. (16 Pages).
Official Action dated Oct. 28, 2021 From the US Patent and Trademark Office Re. U.S. Appl. No. 16/477,204. (46 Pages).
Notification of Office Action and Search Report dated Oct. 18, 2021 From the State Intellectual Property Office of the People's Republic of China Re. Application No. 201780083117.2. (6 Pages).
Official Action dated Jun. 6, 2022 from US Patent and Trademark Office Re. U.S. Appl. No. 16/477,204. (20 pages).

\* cited by examiner

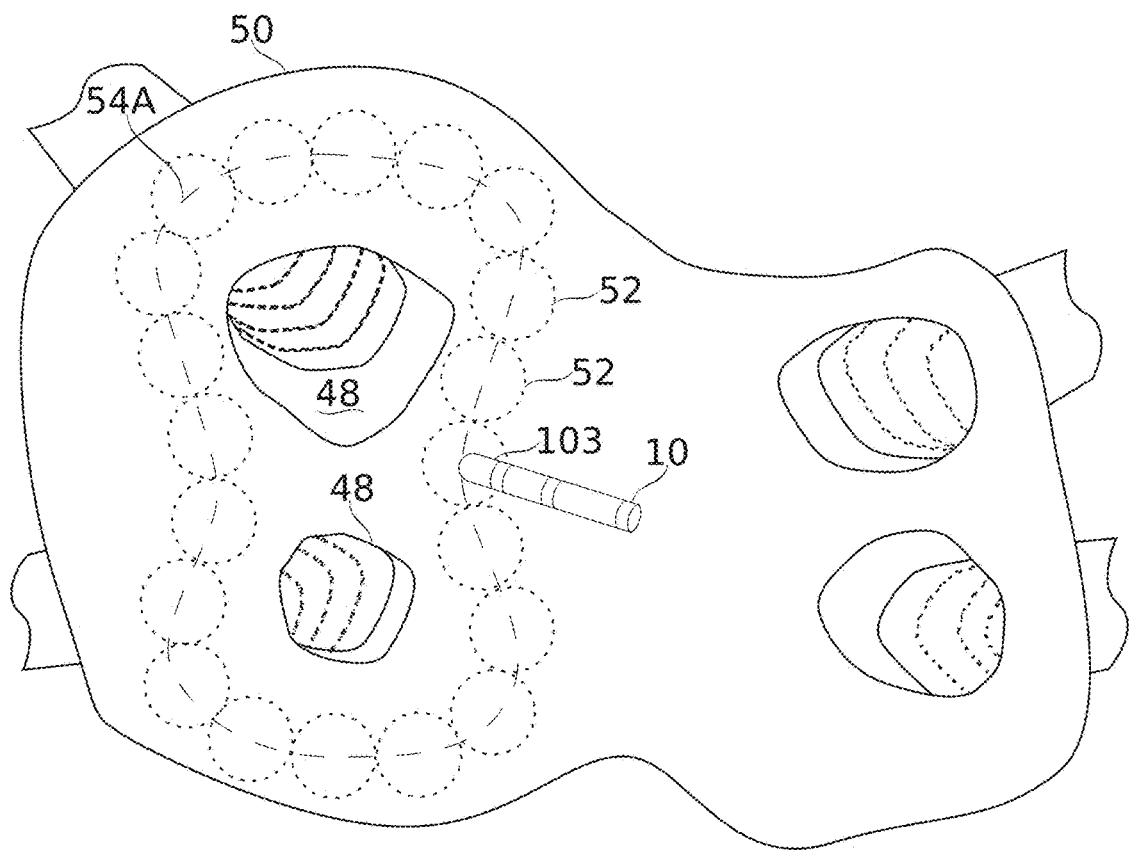
Fig. 2A
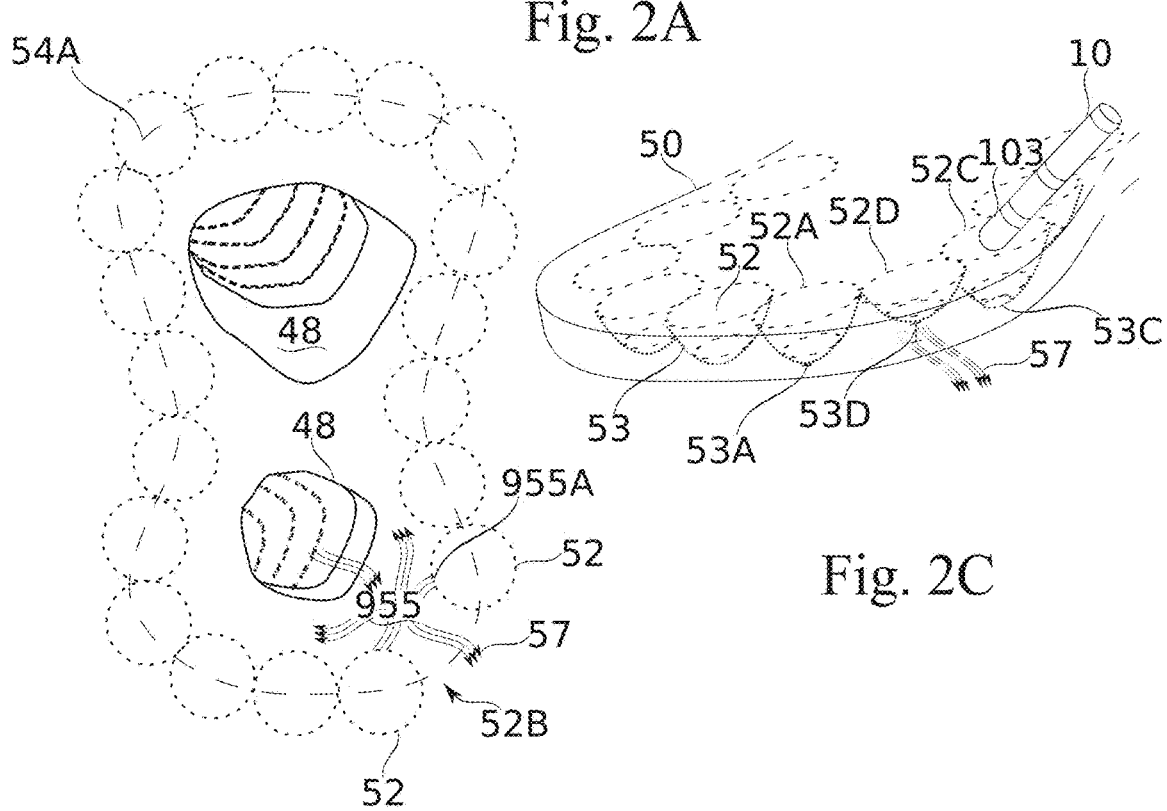
Fig. 2C
Fig. 2B

ESTIMATORS FOR ABLATION EFFECTIVENESS

RELATED APPLICATIONS

This application is a National Phase of PCT Patent Application No. PCT/IB2017/057186 having International filing date of Nov. 16, 2017, which claims the benefit of priority under 35 USC § 119(e) of U.S. Provisional Patent Application Nos. 62/422,748 filed on Nov. 16, 2016, 62/445,377 filed on Jan. 12, 2017 and 62/445,380 filed on Jan. 12, 2017. The contents of the above applications are all incorporated by reference as if fully set forth herein in their entirety.

FIELD AND BACKGROUND OF THE INVENTION

The present invention, in some embodiments thereof, relates to systems and methods for treatment with intrabody catheters and, more particularly, but not exclusively, to systems and methods for estimating prognosis of ablation treatment effectiveness.

Catheterized intra-body ablation probes (for example, RF ablation probes) are in use for minimally invasive ablation procedures. Such procedures are performed, for example, in the treatment of cardiac arrhythmia. In the control of cardiac arrhythmia, a goal of ablation is to create lesions in a pattern which will break pathways of abnormal electrophysiological conduction which contribute to heart dysfunction (such as atrial fibrillation).

Single procedure success rates of catheter ablation at one year appear variable. For example, they have been reported at 15%-60% (Sohns et al., Catheter Contact Force: A Review of Emerging Techniques and Technologies in AF Ablation. Journal Innov Cardiac Rhythm Management, 2014 5:1773-1780).

Earlier time post-procedure success percentages are generally higher. Gaps in the ablation line have been reported to contribute to restoration of impulse conduction (Ouyang et al., Recovered pulmonary vein conduction as a dominant factor for recurrent atrial tachyarrhythmias after complete circular isolation of the pulmonary veins: lessons from double Lasso technique. Circulation. 2005; 111: 127-135).

One form of catheter ablation known as RF ablation relies on heating caused by the interaction between a high-frequency alternating current (e.g., 350-500 kHz) introduced to a treatment region, and a dielectric material (e.g., tissue) in the treatment region. One variable affecting the heating is the frequency-dependent relative permittivity κ of the tissue being treated. The (unitless) relative permittivity of a material (herein, κ or dielectric constant) is a measure of how the material acts to reduce an electrical field imposed across it (storing and/or dissipating its energy). Relative permittivity is commonly expressed as $$\kappa = \varepsilon_r(\omega) = \frac{\varepsilon(\omega)}{\varepsilon_0},$$

where $\omega = 2\pi f$, and f is the frequency (of an imposed voltage signal). In general, $\varepsilon_r(a)$ is complex valued; that is: $\varepsilon_r(\omega) = \varepsilon'_r(\omega) + i\varepsilon''_r(\omega)$.

The real part $\varepsilon'_r(\omega)$ is a measure of how energy of an applied electrical field is stored in the material (at a given electrical field frequency), while the imaginary part $\varepsilon''_r(\omega)$ is a measure of energy dissipated. It is this dissipated energy that is converted, for example, into heat for ablation. Loss in turn is optionally expressed as a sum of dielectric loss $\varepsilon''_{rd}$ and conductivity σ as $$\varepsilon''_r(\omega) = \varepsilon''_{rd} \frac{\sigma}{\omega \cdot \varepsilon_0}.$$

Any one of the above parameters: namely κ, ε, $\varepsilon'_r$, $\varepsilon''_r$, σ, and/or $\varepsilon''_{rd}$, may be referred to herein as a dielectric parameter. The term dielectric parameter encompasses also parameters that are directly derivable from the above-mentioned parameters, for example, loss tangent, expressed as $$\tan \sigma = \frac{\varepsilon''_r}{\varepsilon'_r},$$

complex refractive index, expressed as $n = \sqrt{\varepsilon_r}$, and impedance, expressed as $$Z(\omega) = \sqrt{\frac{i\omega}{\sigma + i\omega\varepsilon_r}} \text{ (with } i = \sqrt{-1} \text{)}.$$

Herein, a value of a dielectric parameter of a material may be referred to as a dielectric property of the material. For example, having a relative permittivity of about 100000 is a dielectric property of a 0.01 M KCl solution in water at a frequency of 1 kHz, at about room temperature (20°, for example; it should be noted that some dielectric properties exhibit temperature dependence). Optionally, a dielectric property more specifically comprises a measured value of a dielectric parameter. Measured values of dielectric parameters are optionally provided relative to the characteristics (bias and/or jitter, for example) of a particular measurement circuit or system. Values provided by measurements should be understood to comprise dielectric properties, even if influenced by one or more sources of experimental error. The formulation "value of a dielectric parameter" is optionally used, for example, when a dielectric parameter is not necessarily associated with a definite material (e.g., it is a parameter that takes on a value within a data structure).

Dielectric properties as a function of frequency have been compiled for many tissues, for example, C. Gabriel and S. Gabriel: Compilation of the Dielectric Properties of Body Tissues at RF and Microwave Frequencies.

SUMMARY OF THE INVENTION

There is provided, in accordance with some embodiments of the present disclosure, a method of estimating effectiveness of ablation to form a lesion, the method comprising: receiving lesion effectiveness parameters; and estimating an effectiveness of the lesion in a tissue; wherein the estimating is based on use by computer circuitry of an estimator constructed based on observed associations between previously analyzed lesion effectiveness parameters, and observed lesion effectiveness, the estimator being applied to the received lesion effectiveness parameters.

In some embodiments, the lesion effectiveness parameters include patient parameter data.

In some embodiments, the lesion effectiveness parameters include one or more of the group consisting of: tissue conditions, parameterized lesion, tissue thickness, fiber orientation, tissue types, contact of an intra-body catheter, measurement of electrical impulse isolation near the lesion, measured intra-lesioning temperature, and dielectric measurements.

In some embodiments, the lesion effectiveness parameters include indications of conditions of formation and/or structure of an ablation lesion in a tissue.

In some embodiments, the conditions of formation of the ablation lesion comprise one or more of the group consisting of ablation power, dielectric quality of contact, angle of contact, force of contact, and timing of ablation.

In some embodiments, the structure of the ablation lesion is indicated by a measure of the depth, size, and/or volume of the ablation lesion.

In some embodiments, the receiving and estimating are performed during an ablation treatment procedure that created the ablation lesion.

In some embodiments, the method comprises adjusting a plan of ablation treatment, based on the estimating.

In some embodiments, the ablation lesion comprises a lesion formed by a single event of applying ablation energy to a focal region of the tissue.

In some embodiments, estimating an effectiveness of the ablation lesion is with respect to one or more criteria of effectiveness.

In some embodiments, the one or more criteria of effectiveness comprise success of electrical isolation of electrical impulses.

There is provided, in accordance with some embodiments of the present disclosure, a method of planning an ablation plan or portion thereof, comprising: receiving patient parameter data; and estimating a prognosis for an ablation plan including ablation plan parameters including planned conditions of formation and/or structure of one or more lesions in a heart wall; wherein the estimating is based on application to the patient parameter data and the ablation plan parameters to an estimator; wherein the estimator is constructed based on observed associations between patient parameter data, parameters of previously performed ablation procedures parameter data, and ablation treatment effectiveness of the previously performed ablation procedures with respect to the one or more criteria of effectiveness.

In some embodiments, the method comprises generated a plurality of ablation plans, and selecting one of the plurality of ablation plans for use, based on the estimating a prognosis.

There is provided, in accordance with some embodiments of the present disclosure, a method of estimating effectiveness of ablation to form an ablation line, the method comprising: receiving ablation line effectiveness parameters; and estimating an effectiveness of the ablation line in a tissue; wherein the estimating is based on use by computer circuitry of an estimator constructed based on observed associations between previously analyzed ablation line effectiveness parameters, and observed ablation line effectiveness, the estimator being applied to the received ablation line effectiveness parameters.

In some embodiments, the ablation line effectiveness parameters include patient parameter data.

In some embodiments, the ablation line effectiveness parameters include one or more of the group consisting of: tissue conditions, parameterized lesion, tissue thickness, fiber orientation, tissue types, contact of an intra-body catheter, measurement of electrical impulse isolation near a lesion of the ablation line, measured intra-lesioning temperature, and dielectric measurements.

In some embodiments, the ablation line effectiveness parameters include indications of conditions of formation and/or structure of a lesion of the ablation line in a tissue.

In some embodiments, the conditions of formation of the ablation line comprise one or more of the group consisting of ablation power, dielectric quality of contact, angle of contact, force of contact, and timing of ablation.

In some embodiments, the structure of the ablation line is indicated by a measure of the depth, size, and/or volume of a lesion of the ablation line.

In some embodiments, the receiving and estimating are performed during an ablation treatment procedure that created the ablation line.

In some embodiments, the method comprises adjusting a plan of ablation treatment, based on the estimating.

In some embodiments, a lesion of the ablation line comprises a lesion formed by a single event of applying ablation energy to a focal region of the tissue.

In some embodiments, estimating an effectiveness of the ablation line is with respect to one or more criteria of effectiveness.

In some embodiments, the one or more criteria of effectiveness comprise success of electrical isolation of electrical impulses across the ablation line.

There is provided, in accordance with some embodiments of the present disclosure, a method of estimating effectiveness of ablation to form an ablation segment, the method comprising: receiving ablation segment effectiveness parameters; and estimating an effectiveness of the ablation segment in a tissue; wherein the estimating is based on use by computer circuitry of an estimator constructed based on observed associations between previously analyzed ablation segment effectiveness parameters, and observed ablation segment effectiveness, the estimator being applied to the received ablation segment effectiveness parameters.

In some embodiments, the ablation segment effectiveness parameters include patient parameter data.

In some embodiments, the ablation segment effectiveness parameters include one or more of the group consisting of: tissue conditions, parameterized lesion, tissue thickness, fiber orientation, tissue types, contact of an intra-body catheter, measurement of electrical impulse isolation near a lesion of the ablation segment, measured intra-lesioning temperature, and dielectric measurements.

In some embodiments, the ablation segment effectiveness parameters include indications of conditions of formation and/or structure of a lesion of the ablation segment in a tissue.

In some embodiments, the conditions of formation of the ablation segment comprise one or more of the group consisting of ablation power, dielectric quality of contact, angle of contact, force of contact, and timing of ablation.

In some embodiments, the structure of the ablation segment is indicated by a measure of the depth, size, and/or volume of a lesion of the ablation segment.

In some embodiments, the receiving and estimating are performed during an ablation treatment procedure that created the ablation segment.

In some embodiments, the method comprises adjusting a plan of ablation treatment, based on the estimating.

In some embodiments, a lesion of the ablation segment comprises a lesion formed by a single event of applying ablation energy to a focal region of the tissue.

In some embodiments, estimating an effectiveness of the ablation segment is with respect to one or more criteria of effectiveness.

In some embodiments, the one or more criteria of effectiveness comprise success of electrical isolation of electrical impulses across the ablation segment.

According to some exemplary embodiments of the present disclosure, a method of estimating ablation segment effectiveness comprises: receiving dielectric measurements; and estimating an effectiveness of the ablation segment in a tissue; wherein the estimating is based on an estimator constructed based on observed associations between previously analyzed dielectric measurements and observed ablation segment effectiveness, the estimator being applied to the received dielectric measurements.

According to some exemplary embodiments of the present disclosure, a method of estimating ablation line effectiveness comprises: receiving dielectric measurements; and estimating an effectiveness of the ablation line in a tissue; wherein the estimating is based on an estimator constructed based on observed associations between previously analyzed dielectric measurements and observed ablation line effectiveness, the estimator being applied to the received dielectric measurements.

According to some exemplary embodiments of the present disclosure, a method of estimating lesion effectiveness comprises: receiving dielectric measurements; and estimating an effectiveness of the lesion in a tissue; wherein the estimating is based on an estimator constructed based on observed associations between previously analyzed dielectric measurements and observed lesion effectiveness, the estimator being applied to the received dielectric measurements.

According to some exemplary embodiments of the present disclosure, a method of estimating edema elicited in a tissue by contact with an intrabody probe: receiving dielectric measurements; and estimating edema elicited in the tissue; wherein the estimating is based on an estimator constructed based on observed associations between previously analyzed dielectric measurements and observed a edema elicited in the tissue, the estimator being applied to the received dielectric measurements.

According to some embodiments, dielectric measurements include signals sensed at one or more electrodes positioned intra-body.

According to some embodiments, wherein the one or more electrodes are provided on an intra-body catheter.

According to some embodiments, the one or more electrodes act in performing the lesion.

According to some embodiments, lesion comprises formation of a lesion in cardiac tissue for the treatment of atrial fibrillation According to some exemplary embodiments of the present disclosure, a method of estimating edema elicited in tissue by contact with an intrabody probe, comprising: receiving input data indicating at least a force applied between the intrabody probe and the tissue; and applying the input data to an elicited edema estimator constructed based on observed associations between previously analyzed input data, and elicited edema, the previously analyzed input data comprising input data indicating at least a force applied between an intra-body probe and a tissue.

There is provided, in accordance with some exemplary embodiments of the present disclosure, a method of estimating prognosis of ablation treatment effectiveness, the method comprising: receiving parameter data, including both patient parameter data and indications of conditions of formation and/or structure of an ablation lesion in a heart wall; and estimating a prognosis for effectiveness of the ablation lesion with respect to one or more criteria of effectiveness; wherein the estimating is based on an estimator constructed based on observed associations between previously analyzed parameter data, and lesion effectiveness with respect to the one or more criteria of effectiveness, the estimator being applied to the received parameter data.

According to some embodiments of the present disclosure, the receiving and estimating are performed during an ablation treatment procedure that created the ablation lesion, and the method comprising adjusting a plan of ablation treatment, based on the estimating.

According to some embodiments of the present disclosure, the ablation lesion comprises a lesion formed by a single event of applying ablation energy to a focal region of the heart wall.

According to some embodiments of the present disclosure, the one or more criteria of effectiveness comprise success of electrical isolation of electrical impulses in one segment of the heart wall from propagation to another segment of the heart wall.

There is provided, in accordance with some exemplary embodiments of the present disclosure, a method of estimating prognosis of ablation treatment effectiveness, the method comprising: receiving parameter data, including both patient parameter data and indications of conditions of formation and/or structure of an ablation line, the ablation line comprising a plurality of adjacent focal ablations in a heart wall; and estimating a prognosis for effectiveness of the ablation line with respect to one or more criteria of effectiveness; wherein the estimating is based on an estimator constructed based on observed associations between previously analyzed parameter data, and ablation line effectiveness with respect to the one or more criteria of effectiveness, the estimator being applied to the received parameter data.

According to some embodiments of the present disclosure, the receiving and estimating are performed during an ablation treatment procedure that created the ablation line, and the method comprising adjusting a plan of ablation treatment, based on the estimating.

There is provided, in accordance with some exemplary embodiments of the present disclosure, a method of planning an ablation procedure or portion thereof, comprising: receiving patient parameter data; and estimating a prognosis for an ablation plan including ablation plan parameters including planned conditions of formation and/or structure of one or more lesions in a heart wall; wherein the estimating is based on application to the patient parameter data and the ablation plan parameters of an estimator; wherein the estimator is constructed based on observed associations between patient parameter data, parameters of previously performed ablation procedures parameter data, and ablation treatment effectiveness of the previously performed ablation procedures with respect to the one or more criteria of effectiveness.

According to some embodiments of the present disclosure, the method comprises generated a plurality of ablation plans, and selecting one of the plurality of ablation plans for use, based on the estimating a prognosis.

There is provided, in accordance with some exemplary embodiments of the present disclosure, a method of mapping a tissue region, comprising: obtaining a plurality of dielectric property measurements of tissue near an electrode probe as the electrode probe is moved through the tissue region, each dielectric property measurement being associated to a position within the tissue region; and creating a map, based on the dielectric property measurements and the positions to which they are associated.

According to some embodiments of the present disclosure, the method comprises associating each dielectric property measurement to a tissue type, based on matching of the dielectric property measurement to known dielectric properties of the tissue type.

According to some embodiments of the present disclosure, the method comprises displaying the map on a computer display.

There is provided, in accordance with some embodiments of the present disclosure, a method of estimating outcome of ablation treatment effectiveness, the method comprising: receiving input data indicating at least one of conditions of formation of and the structure of an ablation segment, wherein the ablation segment comprises a plurality of sub-lesions ablated in a heart wall; and estimating an effectiveness of the ablation segment with respect to one or more criteria of effectiveness; wherein the estimating is based on an estimator constructed based on observed associations between previously analyzed input data, and ablation segment effectiveness with respect to the one or more criteria of effectiveness, the estimator being applied to the received input data.

According to some embodiments of the present disclosure, the criteria of effectiveness comprise blockage of electrical impulse transmission across an extent of the ablation segment.

According to some embodiments of the present disclosure, the indicated conditions of formation include at least one position of an anatomical region in which the ablation segment is formed.

According to some embodiments of the present disclosure, the indicated conditions of formation include at least one of the group consisting of a frequency, power, duration of use, duty cycle, and/or phase of delivery of power through different electrodes.

According to some embodiments of the present disclosure, the indicated conditions of formation include at least one of a thickness, fiber orientation, a frequency, power, duration of use, duty cycle, and/or phase of delivery of power through different electrodes.

According to some embodiments of the present disclosure, the indications of structure include dynamics of change of an electrical measurement obtained from an ablated region of the ablation segment.

According to some embodiments of the present disclosure, the dynamics of change include classification of the change of at least one of linear, exponential, and logarithmic.

According to some embodiments of the present disclosure, the receiving and estimating are performed during an ablation procedure.

According to some embodiments of the present disclosure, the method comprises selecting parameters for a further ablation of the ablation procedure, based on the estimating.

According to some embodiments of the present disclosure, the method comprises displaying to a physician estimated outcome for a plurality of parameter sets for further ablation, so as to allow the physician to select parameters for further ablation based on the estimating.

According to some embodiments of the present disclosure, the conditions of formation include time elapsed between two ablations.

According to some embodiments of the present disclosure, the method further comprises: receiving patient parameter data; and wherein the estimating uses an estimator constructed based on observed associations between previously analyzed patient data, dielectric measurements and ablation segment effectiveness with respect to the one or more criteria of effectiveness, the estimator being applied to the received patient parameter data and dielectric measurements.

There is provided, in accordance with some embodiments of the present disclosure, a method of planning an ablation procedure or portion thereof, the method comprising: receiving patient parameter data; estimating effectiveness of an ablation procedure including ablation procedure parameters comprising indications of at least one of planned conditions of formation of and the planned structure of an ablation segment, wherein the ablation segment comprises a plurality of sub-lesions ablated in a heart wall; and wherein the estimating is based on application of an estimator to the patient parameter data and the ablation procedure parameters; wherein the estimator is constructed based on observed associations between patient parameter data, parameters of previously performed ablation procedures, and ablation effectiveness of the previously performed ablation procedures with respect to the one or more criteria of effectiveness.

There is provided, in accordance with some embodiments of the present disclosure, an estimator estimating outcome of ablation treatment effectiveness wherein the estimator is constructed based on observed associations between: parameter data including indications for a plurality of ablation segments of at least one of conditions of formation of and the structure of an ablation segment, and ablation segment effectiveness with respect to the one or more criteria of effectiveness.

There is provided, in accordance with some embodiments of the present disclosure, a system for estimating an ablation treatment effectiveness, the system comprising computer hardware configured to: receive input data, indicating at least one of conditions of formation of and the structure of an ablation segment, wherein the ablation segment comprises a plurality of sub-lesions ablated in a heart wall; and estimate an effectiveness of the ablation segment with respect to one or more criteria of effectiveness; wherein the computer hardware is configured to estimate using an estimator constructed based on observed associations between previously analyzed input data, and ablation segment effectiveness with respect to the one or more criteria of effectiveness, the estimator being applied to the received input data.

There is provided, in accordance with some exemplary embodiments of the present disclosure, a method of estimating edema elicited in tissue by contact with an intrabody probe, comprising: receiving input data indicating at least a force applied between the intrabody probe and the tissue; and applying the input data to an elicited edema estimator constructed based on observed associations between previously analyzed input data, and elicited edema.

According to some embodiments of the present disclosure, the input data also indicate a duration of force applied between the intrabody probe and the tissue.

According to some embodiments of the present disclosure, the input data also indicate a lesion assessment of the tissue ablation.

According to some embodiments of the present disclosure, the input data also indicate tissue characteristics.

According to some embodiments of the present disclosure, the input data includes dielectric measurements.

According to some embodiments of the present disclosure, the input data includes patient parameter data.

According to some embodiments of the present disclosure, the method further comprises estimating the edema elicited in the tissue based on the applying.

According to some embodiments of the present disclosure, the method further comprises displaying the estimated edema elicited in tissue.

According to some embodiments of the present disclosure, the method further comprises displaying in a map the estimated edema elicited in tissue.

According to some embodiments of the present disclosure, the elicited edema estimator is constructed using machine learning based on the observed associations.

There is provided, in accordance with some exemplary embodiments of the present disclosure, a method of estimating edema elicited in tissue by ablation from an intrabody probe, comprising: receiving input data indicating ablation energy applied by the intrabody probe to the tissue; and applying the input data to an elicited edema estimator constructed based on observed associations between previously analyzed input data, and elicited edema.

According to some embodiments of the present disclosure, the elicited edema estimator produces an estimate based on a model of thermal energy delivery to the tissue.

According to some embodiments of the present disclosure, the elicited edema estimator produces an estimate based on prior observations of a time course of elicited edema in response to temperature.

According to some embodiments of the present disclosure, the elicited edema estimator is calibrated to a particular patient based on observations of a time course of elicited edema in the particular patient.

According to some embodiments of the present disclosure, the elicited edema estimator is constructed using machine learning based on the observed associations.

According to some embodiments of the present disclosure, the elicited edema estimator estimates at least two different time courses of edema for regions affected by the ablation energy.

According to some embodiments of the present disclosure, the input data also indicate a lesion assessment of the tissue ablation.

According to some embodiments of the present disclosure, the input data also indicate tissue characteristics.

According to some embodiments of the present disclosure, the input data includes dielectric measurements.

According to some embodiments of the present disclosure, the input data includes patient parameter data.

According to some embodiments of the present disclosure, the method further comprises estimating the edema elicited in the tissue based on the applying.

According to some embodiments of the present disclosure, the method further comprises displaying the estimated edema elicited in tissue.

According to some embodiments of the present disclosure, the method further comprises displaying in a map the estimated edema elicited in tissue.

There is provided, in accordance with some exemplary embodiments of the present disclosure, a method of estimating edema elicited in tissue by contact with an intrabody probe, comprising: receiving input data indicating at least one tissue characteristics; and applying the input data to an elicited edema estimator constructed based on observed associations between previously analyzed input data, and elicited edema.

According to some embodiments of the present disclosure, the input data also indicate a lesion assessment of the tissue ablation.

According to some embodiments of the present disclosure, the input data also indicate tissue characteristics.

According to some embodiments of the present disclosure, the input data includes dielectric measurements.

According to some embodiments of the present disclosure, the input data includes patient parameter data.

According to some embodiments of the present disclosure, the method further comprises estimating the edema elicited in the tissue based on the applying.

According to some embodiments of the present disclosure, the method further comprises displaying the estimated edema elicited in tissue.

According to some embodiments of the present disclosure, the method further comprises displaying in a map the estimated edema elicited in tissue.

According to some embodiments of the present disclosure, the elicited edema estimator is constructed using machine learning based on the observed associations.

According to some embodiments of the present disclosure, the method further comprises planning an ablation path based on the estimation.

According to some embodiments of the present disclosure, the method further comprises adjusting pre-planned ablation path based on the estimation.

According to some embodiments of the present disclosure, the method further comprises creating an edema map for the specific patient based on the estimation.

According to some embodiments of the present disclosure, the method further comprises displaying the edema map.

There is provided, in accordance with some embodiments of the present disclosure, a method of estimating edema elicited in tissue by ablation from an intrabody probe, comprising: receiving input data indicating ablation energy applied by the intrabody probe to the tissue; and applying the input data to an elicited edema estimator constructed based on a model of edema incorporating modeling of temperature as a function of ablation energy applied, matched to a time course of modeled edema elicited.

According to some embodiments of the present disclosure, the time course of modeled edema includes an initial lag of at least 1 minute, followed by a rising phase.

According to some embodiments of the present disclosure, the modeled edema rises to at least 98% of a maximum value within about 30 minutes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s)

having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 2A-2C schematically illustrate aspects of lesioning to block of tissue conduction, for example for the treatment of atrial fibrillation, in accordance with some exemplary embodiments of the disclosure;

Figure 1A:
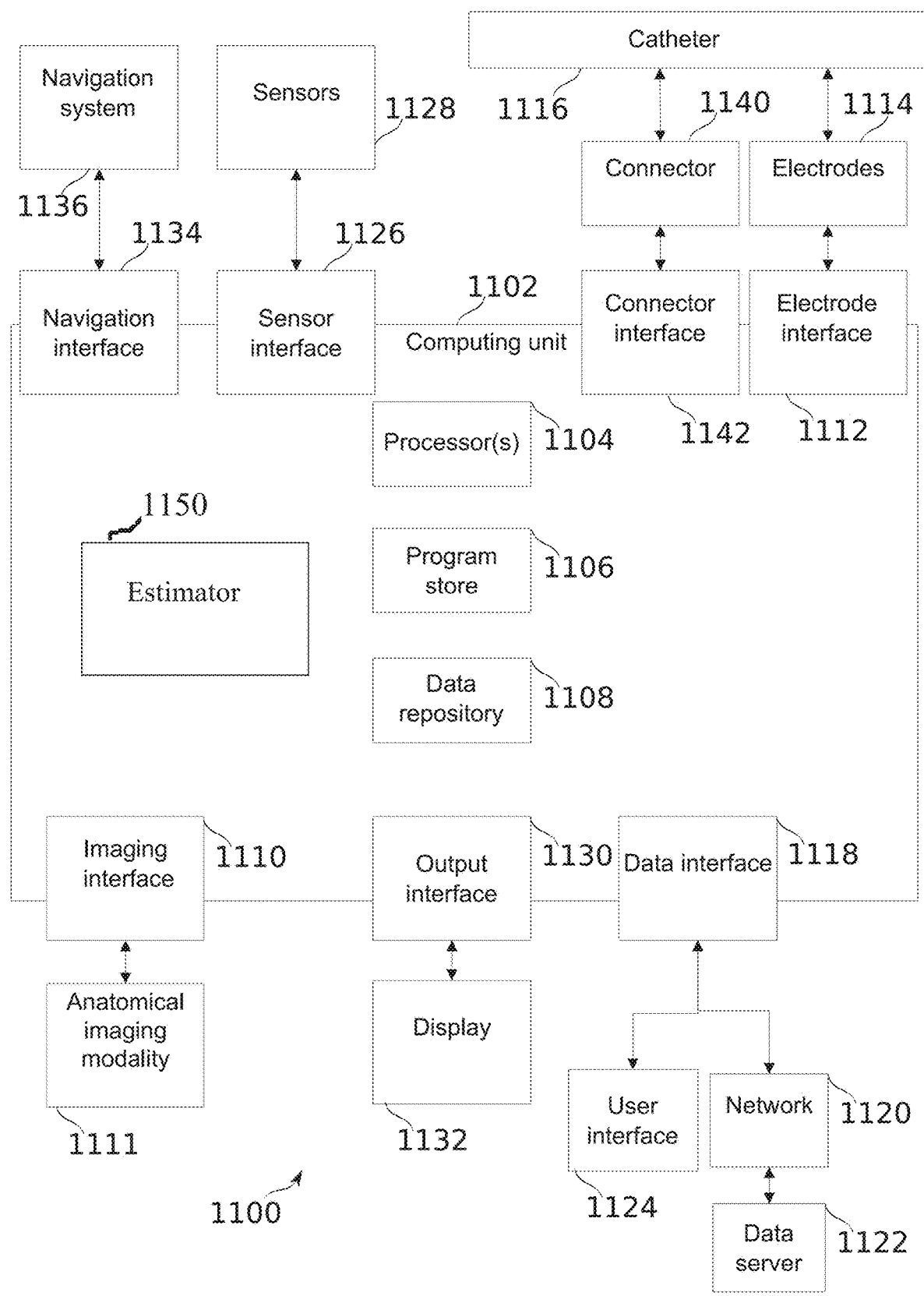
FIG. 1A is a block diagram of components of a system for ablation and/or tracking the position of an intra-body catheter, which may be used with an estimator, in accordance with some embodiments of the present disclosure.

DESCRIPTION OF SPECIFIC EMBODIMENTS
OF THE INVENTION

The present invention, in some embodiments thereof, relates to systems and methods for treatment with intrabody catheters and, more particularly, but not exclusively, to systems and methods for estimating prognosis of ablation treatment effectiveness, and/or planning and/or dynamically adjusting planning of treatments such as ablation treatments performed using intrabody catheters based on the estimation.

Overview

An aspect of some embodiments of the current invention relates to the use of estimators to predict short, medium, and/or long-term outcomes of an ablation procedure, or portion thereof (ablation treatment effectiveness). In some embodiments, the ablation procedure is a procedure to ablation atrial wall tissue, e.g. to treat cardiac arrhythmias, such as: atrial fibrillation. Optionally, the ablation procedure is carried out using an RF ablation probe. The term "ablation treatment effectiveness" may include lesion effectiveness (also referred to as effectiveness of an ablation lesion), ablation line effectiveness (also referred to as effectiveness of an ablation line), and/or ablation segment effectiveness as next described. As used herein, an estimator or effectiveness estimator may refer to a lesion effectiveness estimator, ablation line effectiveness estimator and/or ablation segment effectiveness estimator (also referred as segment estimator or ablation segment estimator).

In some embodiments of the invention, an estimator may be used to predict acute (e.g., immediate) and/or persistent (e.g., over a period of at least 1 month, 3 months, 6 months, 1 year, 2 years, 5 years, or another longer, shorter, or intermediate period) effectiveness of an ablation treatment.

In some embodiments of the invention, a lesion effectiveness estimator may be used to predict acute (e.g., immediate) and/or persistent (e.g., over a period of at least 1 month, 3 months, 6 months, 1 year, 2 years, 5 years, or another longer, shorter, or intermediate period) effectiveness of an ablation lesion. Effectiveness of an ablation lesion, in some embodiments, comprises completeness of electrical isolation across, under, or over the lesion (transmurality of the lesion).

In some embodiments of the invention, an ablation line effectiveness estimator may be used to predict acute (e.g., immediate) and/or persistent (e.g., over a period of at least 1 month, 3 months, 6 months, 1 year, 2 years, 5 years, or another longer, shorter, or intermediate period) effectiveness of an ablation line lesion. Effectiveness of an ablation line, in some embodiments, comprises completeness of electrical isolation across, under, or over the ablation line (transmurality of the ablation line).

"Effectiveness" is a general term used herein to refer to achievement of any targeted outcome, for example, electrical isolation, absence of disease (optionally, absence of disease for some particular period post-treatment), and/or safety conditions, according, for example, to the feedback data used in the construction of the estimator. Any such targeted outcome is also referred to herein as a "criterion of effectiveness".

An aspect of some embodiments of the current invention relates to the use of estimators to plan and/or predict outcomes of an ablation procedure; and more particularly, in some embodiments, to plan and/or predict outcomes related to ablation treatment effectiveness of an ablation segment ablated as part of an ablation procedure.

In some embodiments, an estimator comprises a set of learned weights applied, for example, to a neural network, to terms of a model equation, and/or inputs to a function. In some embodiments, an estimator is nonlinear, e.g., the weights include nonlinear combinations.

Application of an estimator may comprise plugging into the estimator appropriate input values, and calculating the result. The result may be produced as an estimated lesion "effectiveness" or an estimated ablation line "effectiveness" or an estimated ablation segment "effectiveness", wherein effectiveness can be defined and/or expressed differently in different embodiments, as described herein. The estimator may be created based on a dataset associating input parameters, for example: parameters of the lesion, lesion of the ablation line, and/or lesion of the ablation segment; lesioning procedure, and/or patient data parameters with observed outcomes. Patient data parameters are also referred to herein as patient parameter data.

Optionally, the estimator is created using machine learning to discover correlations between input parameters and observed outcomes; additionally or alternatively, the estimator is created, for example, based on general statistical methods. The estimator may be applied to one or more input parameters of subsequent lesions/lesioning procedures, and the result may be used as a basis for further decision making. For example, within a procedure, updated estimator results are optionally used to indicate whether or not the procedure so far is likely to lead to a successful result, or whether mitigating actions should be taken. Optionally, simulated results of intended mitigating actions are also subjected to the estimator before being undertaken, for example, to help select from among a plurality of mitigating action choices which is most likely to be effective.

In some embodiments, the estimator may also accept patient data parameters. Patient data parameters may include, for example: age, sex, weight, blood pressure, patient medical history, laboratory tests or self-tests, and/or patient genetics.

In some embodiments, an effectiveness estimator is used to predict long-term persistence of lesions. Optionally, planning of follow-up treatment is based at least partially on predictions of the effectiveness estimator.

In some embodiments, an effectiveness estimator may take into account the occurrence (or predicted occurrence) of edema in the vicinity of a lesion location. Edema is typically acutely elicited in heart tissue by lesioning or mechanical insult, and once developed (after several minutes) can interfere with the effect of subsequent ablations. In some embodiments, an estimator takes into account the positions and relative times of recent ablations in order to help predict the effectiveness of subsequent ablations (actual ablations and/or planned ablations). Optionally, the system suggests alternative plans to help adjust for the effects of edema—for example, suggesting a different order of ablations, different timing, and/or different operating settings (power, time, frequency, phase) for the ablation modality.

In some embodiments of the invention, an ablation line effectiveness estimator is used to predict acute and/or persistent effectiveness of an ablation line for overall completeness of electrical isolation (e.g., to estimate a likelihood of there being or developing an inter-lesion gap allowing electrical reconnection). An ablation line, in some embodiments, comprises a group of lesions introduced together by ablation to achieve a clinical result. Typically, the lesions are introduced as a chain of lesions extending along a pathway (herein, this may be referred as an ablation line, ablation path, lesion line, lesion path, or path), with the target of creating an uninterrupted barrier to electrical transmission from one side to the other. Even if each individual lesion of an ablation line is apparently transmural and permanent (for example, as actually measured, and/or as judged and/or predicted by the lesion effectiveness estimator), there remains a possibility that the individual lesions are placed so that the ablation line overall still allows electrical impulse transmission across it. The ablation line effectiveness estimator, in some embodiments, is applied to data describing the overall shape of the ablation line, from which an estimate of the ablation line's overall electrical isolation effectiveness in the immediate, short-term, and/or long-term future is produced.

The ablation line effectiveness estimator is optionally created based on a dataset associating input parameters of the ablation line and/or ablation line procedure with observed outcomes. The estimator may be applied to the input parameters of subsequent ablation procedures, and the result optionally used as a basis for further decision making. For example, within a procedure, updated estimator results are optionally used to indicate whether or not the procedure so far is likely to lead to a successful result, or whether mitigating actions should be taken. Optionally, simulated results of intended mitigating actions are also subjected to the estimator before being undertaken, for example, to help select from among a plurality of mitigating action choices which is most likely to be effective.

An aspect of some embodiments of the current invention relates to systems and methods for planning catheter ablation (using a probe of the catheter) of a tissue in a patient (producing what is referred to herein as an ablation plan, lesion plan, line of planned ablation, lesioning plan, plan of ablation treatment, or planned lesion).

In some embodiments, an ablation plan includes specification of where ablation is to occur; optionally defined as a line or path, an area, and/or a volume (herein, ablation plans for a path are provided as examples, without limitation away from embodiments using areal or volumetric specifications). An ablation plan optionally comprises the definition of ablation parameters along the ablation line (for example, frequency, total energy delivered, power and/or timing). An ablation plan optionally specifies movements of an ablation probe more particularly—for example, from what start point, in what order, to what end point, at what angle, and/or with what timing between movements. Optionally, the ablation plan includes specification of the ablation catheter (e.g., its probe) itself.

In some embodiments, the method for planning an ablation line comprises receiving (for example, receiving by a lesion planning system, by a processor configured to implement lesion planning, and/or from a user) an indication of a preliminary target form of a lesion to be formed on and/or within a target anatomical structure of the patient by the planned catheter ablation. Optionally, the preliminary target form is indicated as a path (for example a continuous path, and/or a path described as a series of locations to be lesioned) specified with respect to a representation (e.g., a 3-D display) of patient-specific anatomy.

In some embodiments, patient-specific anatomy comprise 3-D imaging data (for example, MRI, CT, NMR, and/or data from another imaging modality) describing and/or displaying patient-specific anatomy. In some embodiments, the data are marked (and/or characterized after receipt) with respect to thermal and/or dielectric properties. Optionally, thermal properties include, for example, thermal conductivity, heat capacity, rate of active heat transfer (for example, by blood perfusion), and/or rate of metabolic heat generation. Optionally, dielectric properties include, for example, the frequency-dependent relative permittivity of tissue, and/or another property related to relative permittivity; for example, as described in the Background of the Invention, herein.

In some embodiments, planning an ablation plan is described herein in terms of the placement of the ablation path, the plan of ablation probe movement along that path and/or the parameters of ablation which optionally are selected to vary as the probe moves along the path. In some embodiments, these plan features are optionally determined together and/or in parallel. For example, which sub-lesion positions are optimal along a portion of the lesion path is potentially influenced by how much and/or with what timing lesioning energy is delivered. In some embodiments, determining a final ablation plan comprises iteratively adjusting these plan features to approach more optimal results, and/or generating a selection of alternative plans from which the most optimal result is chosen. In some embodiments, one or more steps of such planning may be carried out by application of a thermal and/or dielectric property simulation of the tissue to be treated.

In some embodiments, planning an ablation plan includes planning an optimal path. In some embodiments, the optimal path may be understood as the path which best simultaneously satisfies several, potentially contradictory, constraints and/or criteria. In general, the overall ablation plan preferably seeks effectiveness of the block while protecting against collateral damage, and achieving the greatest speed of lesioning compatible with these two goals. More specifically, the constraints and/or criteria include, for example:

minimization of path length;
minimization of sub-lesion number;
minimization of complexity, required precision, and/or time of catheter maneuvering;
avoidance of collateral damage to non-target tissue;
access to the target, dependent, for example, on anatomy shape and/or catheter mechanics; and/or
features of the target anatomy, for example, tissue wall thickness, existing lesions, and/or fiber direction.

In some embodiments, the method for planning an ablation line comprises calculating (e.g., by a lesion planning system) simulated results of lesioning, based on the characterization of data describing patient-specific anatomy. In some embodiments, estimated results of lesioning may be obtained by an effectiveness estimator. Estimated results of lesioning may include short-term effects such as heating, collateral effects on nearby tissue, reversible block, and/or edema; as well as predictions of long-term effects such as the irreversibility of block. Estimated results of lesioning obtained by an effectiveness estimator may include ablation treatment effectiveness.

In some embodiments, the simulation is based on thermal and/or dielectric tissue properties specified in the received data. In some embodiments, the simulation comprises simulation of the effects of power loss density (PLD) in tissue under excitation by a RF field modeled after a field produced by an ablation probe of an RF ablation catheter. Optionally, when non-RF ablation is performed (such as by substance injection, cryoablation and/or irreversible electroporation), another equation is used to simulate the initial distribution of ablating energy to (or its ablating removal from) tissue. Additionally or alternatively, simulation of thermal conduction is also performed (for example, based on the thermal continuity equation). Optionally, simulation comprises accounting for interaction between thermal and dielectric properties, for example, changes in dielectric properties during heating as a result of temperature change potentially subsequently influence heating itself in turn. Optionally, simulation comprises accounting for interaction between ablation and physiological responses, for example, edema arising post-ablation potentially affects how later attempts to ablate the same and/or a nearby region proceeds. Optionally, this is accounted for between sequential sub-lesions, and/or as an ablation probe moves along a line of planned ablation.

In some embodiments, the estimated results of lesioning may be used in planning a target form of a lesion (e.g., in planning an ablation). Optionally, the planning comprises planning an ablation line (e.g., a line of locations at which ablation is performed to create sub-lesions), along which a lesion is to be formed. Optionally, the ablation plan comprises specification of ablation parameters to be used along the line—for example, particular positions, angles, and/or pressures for contact between an ablation probe and target tissue; energies used to activate the probe (optionally including frequency and/or voltage); selection of electrodes (optionally including specification of phased activation of electrodes); and/or durations of ablation. Optionally parameters of ablation (for example, parameters defining energies, details of positioning, and/or durations) are varied at different positions along the line (other spatial arrangement) of planned ablation. Optionally, an ablation plan may include the order of ablations, for example, where ends of a looping line of ablation should meet, and/or placement and/or timing of sub-lesions to take advantage of previously existing lesions and/or recent administration of ablation energy. Herein, the term "sub-lesion" is used to indicate portions of a larger ablation result created by an ablation probe upon or along a portion of larger area to be lesioned (e.g., defined as a line or path, but not excluding definitions as areas or volumes). Ablation is optionally performed by a probe moved stepwise between lesion foci (with ablation at each step defining a sub-lesion), and/or by dragging an ablation probe over a continuous extent of target tissue (where a sub-lesion is defined by the extent of dragged-out ablation, and/or optionally by a change in parameter, for example, a change in ablation power, rate of drag, or another parameter). Herein, the term lesion, used as a noun, is generally equivalent to the term "sub-lesion".

Optionally, the ablation plan takes into account (and is formulated to avoid damaging) the patient-specific positions of anatomical structures subject to collateral damage (for example, the esophagus, phrenic nerve, and/or venous roots, as in the case of ablations to treat atrial fibrillation). Optionally, the ablation plan takes into account aspects related to maneuvering within the confines of an anatomical space. For example, there may be mechanical limitations on the maneuvering of an ablation catheter. In another example, a requirement for precision of placement may be relaxed in some positions along a line of planned ablation (e.g., a tolerance to gaps in a lesion line may be greater where fibers are oriented so that they are cut by, rather than running between, adjacent sub-lesions); while certain maneuvers (such as joining lesion line ends) are potentially more prone to error and/or complication. In some embodiments, an ablation plan is designed to match more difficult maneuvers to lesion positions where delay and/or error is potentially less damaging to the end result. In some embodiments, the ablation plan is calculated for a shortest line of planned ablation, a minimal number of sub-lesions placed, and/or a minimal use of ablation energy, compatible with the relative importance (e.g., priority and/or weighting) of other criteria and/or constraints.

In some embodiments, the method comprises providing (for example, to a lesion planning system) an indication of the planned target form. Optionally, the indication comprises showing a line of planned ablation together with a 3-D representation of the target anatomical structure. Optionally, the indication also comprises display of targeted ablation positions along the line, and/or the order and/or timing in which the ablation positions are to be targeted. The indication may also include detailed aspects of the plan such as planned lesion size and/or lesioning parameters such as power and duration. Optionally, expected results of an ablation plan are presented to a user a priori, for example, as an ablation line indication presented together with a 3-D model of the target tissue, as one or more estimates of time of ablation (partial or overall), as a likelihood of successful treatment, etc. In some embodiments, likelihood of successful treatment is calculated based on success in other patients having similar ablation procedure characteristics.

In some embodiments, the planning comprises automatic adjustment of the preliminary target form of the lesion to satisfy one or more criteria and/or constraints; for example, criteria and/or constraints affecting safety, procedure outcome, efficiency of power application, and/or treatment duration; and/or practicability of the lesion plan. In some embodiments, adjusting a preliminary target form of a lesion may be based on results obtained by an effectiveness estimator during an ablation treatment.

In some embodiments, an ablation plan includes the definition of intermediate target results which can be monitored while the plan is carried out. For example, lesion effectiveness or ablation line effectiveness may be monitored (e.g., by an estimator) during an ablation in progress (for example, based on dielectric property and/or thermal measurements). In some embodiments, intermediate target results may be used to adjust one or more parameters of the ablation in progress, and/or another parameter of the ablation plan.

In some embodiments, a preliminary target form is provided automatically and/or by a user as an indication of a selection of a more generally specified lesion form, for example, a selection specified in terms of one or more anatomical landmarks, and/or a topographic relationship of the lesion with respect to the landmarks. For example, the indication may be "surrounding a root of a pulmonary vein" (additionally or alternatively, the root of a plurality of veins, of another blood vessel, or any other relationship between anatomical landmark and lesion form suitable to the application).

An aspect of some embodiments of the current invention relates to systems and/or methods of dynamic adjustment of an ablation plan of a tissue in a patient. In some embodiments, adjustment may be based on results obtained from an effectiveness estimator. In some embodiments, differences between an ablation plan and the actual ablation as it occurs are automatically adjusted for by changing the plan in media res, optionally while still taking into account criteria and/or constraints affecting safety, procedure outcome, and/or speed and/or practicability of the lesion plan. Ablation plan adjustments may occur entirely automatically, and/or be provided as suggestions and/or alternatives for a user to follow and/or select among. Optionally, alternatives (particularly when they are presented in response in the contingency of a complication or error in the procedure) are presented with an indication of likely relative risks/benefits. In some embodiments, an effectiveness estimator may be used to estimate the relative risks/benefits.

In some embodiments, the ablation plan includes a sequence of position targets describing lesioning positions of a target anatomical structure at which sub-lesions and/or other portions of a completed larger lesion are planned to be created. Optionally, the sequence comprises a discrete sequence—for example, a sequence of spot-like sub-lesions along a line of planned ablation. Optionally, the sequence comprises continuous sequence—for example, a sequence of positions passed through as an ablation catheter ablation probe is dragged along a portion of a line of planned ablation.

In some embodiments, an ablation plan is received; for example, received by a system configured to track a probe of an ablation catheter during ablation. In some embodiments, the sequence of position targets is compared to the actual (e.g., tracked by a catheter tracking system) positions of an ablation catheter where it performs ablation. Preferably, the comparison occurs during an ablation procedure. Optionally, this is followed by automatic correction (optionally augmented by user input such as confirmation and/or selection of options) before certain difficulties caused by delay arise—for example, loss of lock between the relative position of the ablation catheter and the lesion, and/or evolution of the lesion to a form which may be more difficult to lesion (tissue typically becomes edematous within a few minutes of lesioning, which can in turn make it difficult to reliably make further lesioning adjustments afterward).

In some embodiments, the ablation plan is adjusted, based on differences between the sequence of position targets and the sequence of tracked positions. Generally, the adjustment seeks to preserve key features of the final lesion which are potentially at risk due to a partial deviation from the plan. One significant form of error which can arise in the treatment of atrial fibrillation by lesioning is the placement of sub-lesions which are not sufficiently close to prevent impulse transmission from crossing between them. In some embodiments, the plan is adjusts by inserting one or more additional lesions, and/or by adding further lesioning energy at one of the sub-lesion positions. At the same time, in some embodiments, safety constraints are also imposed on the plan: for example, to prevent collateral damage to sensitive structures such as the esophagus, venous roots, autonomic ganglia, and/or phrenic nerve.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Systems for Ablation and/or Tracking the Position of an Intra-Body Catheter

Reference is now made to FIG. 1A, which is a block diagram of components of a system for ablation and/or tracking the position of an intra-body catheter, which may be used with an estimator, in accordance with some embodiments of the present invention.

In some embodiments, the system of FIG. 1A may allow an operator to monitor progress of an intra-body procedure according to a treatment plan, for example, lesioning along an ablation, optionally with sufficient accuracy and precision to allow monitoring actual vs. planned ablations. In some embodiments, an estimator may be used to predict acute (e.g., immediate) and/or persistent (e.g., over a period) effectiveness of an ablation treatment.

Optionally, the system is configured to dynamically adjust the ablation plan according to the progress of the procedure and/or based on results obtained by an effectiveness estimator during an ablation treatment. The system of FIG. 1A may execute, for example, the method of FIGS. 1B and/or 6, either by an estimator embedded in processor 1104 or by a dedicated estimator 1150. Estimator 1150 may be learned lesion estimator 1604 (as described in FIG. 1B) and/or ablation line estimator 1804 (as described in FIG. 6) and/or ablation segment estimator 2104 (as described in FIG. 14A) and/or edema estimator 2604 (as described in FIG. 18).

It is noted that the system of FIG. 1A may track the location of the distal end of the catheter (the probe end) by separately and substantially simultaneously tracking the position of sensors, electrodes and/or other conducting ports on the distal end of the catheter.

As used herein, the terms sensor and electrode are sometimes interchangeable, for example, where referring to an element that performs measurements of one or more electrical properties (e.g., dielectric properties, conductance, impedance, voltage, current, and/or electrical field strength). For example, the electrodes may function as the sensors, such as by transmitting from one electrode to a second electrode, where the second electrode functions as a sensor. Impedance may be measured between respective electrode pairs, and/or between a designated electrode and a reference electrode (which may be located outside the body and/or within the body, such as on the catheter).

The system of FIG. 1A may provide additional features, for example, estimation of contact force applied by the distal end of the catheter (the probe at the probe end of the catheter) to the tissue wall, estimation of the lesion formation (e.g., estimation of lesion structure, for example, size, volume and/or depth), estimation of tissue temperature, and/or mapping of fibrotic regions.

System 1100 may include a program store 1106 storing code, and a processor 1104 coupled to program store 1106 for implementing the stored code. Optionally, more than one processor may be used. It is noted that program store 1106 may be located locally and/or remotely (e.g., at a remote server and/or computing cloud), with code optionally downloaded from the remote location to the local location for local execution (or code may be entirely or partially executed remotely).

System 1100 may include an imaging interface 1110 for communicating with one or more anatomical imaging modalities 1111 that acquire a dataset of imaging data of a patient, for example, anatomical imaging data, e.g., a computer tomography (CT) machine, an ultrasound machine (US), a nuclear magnetic resonance (NM) machine, a single photon emission computed tomography (SPECT) machine, a magnetic resonance imaging (MRI) machine, and/or other structural and/or functional anatomical imaging modality machines. Optionally, imaging modality 1111 acquires three dimensional (3-D) data and/or 2-D data. It is noted that the anatomical images may be derived and/or acquired from functional images, for example, from functional images from an NM machine.

System 1100 may include an output interface 1130 for communicating with a display 1132, for example, a screen or a touch screen. Optionally, physically tracked location coordinates are displayed within a presentation of the dataset; for example, the 3-D acquired anatomical images are displayed on display 1132, with a simulation of the location of the distal end of the catheter within the displayed image.

System 1100 may include an electrode interface 1112 for communicating with a plurality of physical electrodes 1114 and/or sensors (optionally, the electrodes serve as the sensors) located on a distal end portion of a physical catheter 1116 designed for intra-body navigation; for example: an electrophysiology (EP) ablation catheter, and/or another ablation catheter (e.g., a chemical ablation or injection catheter). Alternatively or additionally, system 1100 includes a navigation interface 1134 for communicating with a catheter navigation system 1136; optionally a non-fluoroscopic navigation system; optionally, an impedance measurement based system.

In some embodiments, intra-body navigation is performed based on body surface electrodes that receive and/or transmit current (e.g., alternating current) in different frequencies and/or different times between co-planar directions. Analysis of the electrical and/or thermal parameters obtained from the sensors of the catheter, separated into the different channels, is optionally used to estimate the location of each sensor relative to each body surface electrode. A calibration of the distances between the sensors (e.g., based on manufacturing specifications of the catheter, and/or measurements such as using fluoroscopy or other methods) may be performed.

Optionally, system 1100 includes a sensor interface 1126 for communicating with one or more sensors 1128, which may be in the body or external to the body; for example, for measuring electrical and/or thermal parameters, for example, impedance and/or conductivity and/or thermal conductivity and/or heat capacity and/or metabolic heat generation of the blood, the myocardium, and/or other tissues.

Optionally, system 1100 includes a data interface 1118, for communicating with a data server 1122, directly or over a network 1120, to acquire estimated dielectric and/or thermal tissue values for association with the acquired imaging dataset. Alternatively, the estimated dielectric and/or thermal values are stored locally, for example, on data repository 1108.

In some embodiments, data interface 1118 may be used to acquire patient data parameters and/or additional data required for estimator 1150.

Optionally, a user interface 1124 is in communication with data interface 1118, for example, a touch screen, a mouse, a keyboard, and/or a microphone with voice recognition software.

Optionally, system 1100 (e.g., computing unit 1102) includes a connector 1140 connecting between catheter 1116 (e.g., RF ablation catheter, injection catheter) and a connector interface 1142 (and/or electrode interface 1112). Connector 1140 may be used to add additional features to existing catheters, such as off the shelf catheters, for example, RF ablation catheters, at least by acting as an input of signals communicated by the catheter for processing by system 1100. The signals communicated by the catheter are intercepted by circuitry within connector 1140 and transmitted to interface 1142 and/or 1112, without interfering with the signal transmission. The intercepted signals may be analyzed by system 1100, for example, to perform real-time tissue measurements (e.g., contact force, pressure, ablated volume and/or depth, temperature, and/or fibrosis mapping), to perform localization of the catheter, to estimate ablation treatment effectiveness and/or to identify the type of the catheter.

It is noted that one or more of interfaces 1110, 1118, 1112, 1126, 1130, 1134, 1142 may be implemented, for example, as a physical interface (e.g., cable interface), and/or as a virtual interface (e.g., application programming interface). The interfaces may each be implemented separately, or multiple (e.g., a group or all) interfaces may be implemented as a single interface.

Processor 1104 may be coupled to one or more of program store 1106, data repository 1108, and interfaces 1110, 1118, 1112, 1126, 1130, 1134, 1142.

Optionally, system 1100 includes a data repository 1108, for example, for storing the dataset (e.g., imaging data of a patient), the simulation, received electrical and/or thermal parameters, and/or other data (such as: patient data parameters). The data may be displayed to a user (e.g., physician) before, during and after the procedure.

It is noted that one or more of processor 1104, program store 1106, data repository 1108, and interfaces 1110, 1118, 1112, 1126, 1130, 1134, 1142 may be implemented as a computing unit 1102, for example, as a stand-alone computer, as a hardware card (or chip) implemented within an existing computer (e.g., catheterization laboratory computer), and/or as a computer program product loaded within the existing computer.

Program store 1106 optionally includes code implementable by processor 1104 that represents an effectiveness estimator based on one or more lesion effectiveness parameters and/or other data.

In some embodiments, a dataset of a body portion of a patient including anatomical imaging data of the patient (optionally 3-D data) is provided, for example, acquired from imaging modality 1111 (e.g., CT, MRI), retrieved from repository 1108, and/or acquired from an external server or other storage. Alternatively or additionally, the dataset is acquired and/or derived from a functional imaging modality, for example, NM and/or SPECT. For example, data from the NM modality may be used to infer the location of autonomous nervous system components (e.g., one or more ganglion plexi) designated for treatment on the dataset from the CT modality. In some embodiments, anatomical imaging data may be otherwise obtained, for example: anatomical structure may be reconstructed from one or more signals obtained by electrodes 1114 or sensor 1128. In some embodiments, an intrabody electrode probe comprising electrodes 1114 is used to map out an anatomical space in which a procedure is to be performed, effectively producing a 3-D model of the space, optionally in parallel with performing the procedure. In some embodiments, reconstruction from the mapping uses known spatial constraints on the relative positions of a plurality of sensing electrodes positioned at known spaced positions relative to the geometry of the intrabody probe. Optionally, local spatial calibration defined by the spatial constraints is used in combination with constraints on the spatial coherence of measurements as part of the reconstruction process.

The anatomical imaging data may serve as a basis for geometrical structure and/or modeling of internal organs of the patient, for example, the organs are segmented using image segmentation code.

Optionally, the anatomical imaging data includes the target tissue for treatment in a catheterization procedure; for example, the heart. Optionally, the anatomical imaging data includes tissues surrounding the target tissue, for example, a full body scan, a full thorax scan, a chest and abdominal scan, and/or a chest scan. For example, for an intra-cardiac ablation procedure, a full thorax scan may be performed.

Optionally, the anatomical imaging data is analyzed and/or processed to identify different types of tissues within the imaging data, for example, each pixel data or region is classified into a tissue type. Suitable classification methods include, for example, according to image segmentation methods, according to a predefined imaging atlas, and/or based on Hounsfield units.

It is noted that the patient may undergo imaging before the catheterization procedure, for example, as a separate outpatient procedure.

In some embodiments, ablation is carried out according to an ablation plan. Optionally, the ablation plan is specified largely automatically based on inputs which set parameters for an ablation procedure such as regions targeted to be isolated by the procedure, optionally along with information that characterizes the environment of the procedure-tissue states and shapes, for example. The ablation plan may be understood as comprising one or more of the three levels described herein. At the high level is the overall line of ablation along which lesions will be formed. In addition to design for effectiveness (that is, to achieve complete isolation), the line of ablation may be preferably efficient (minimum suitable length), safe (minimized potential for side effects) and/or reliable (avoiding areas that are prone to mistakes and/or difficulties). At the lowest level are individual lesions (also called "sub-lesions" herein) which should be connected together along the line of ablation to form a complete block, and moreover should be transmural (extending across the heart wall) so that they also block transmission throughout the wall thickness. An intermediate level of planning is at the level of lesion segments, comprising pairs of adjacent lesions and their relationship to one another. Adjacent lesions may interact, e.g., temporally through residual temperature effects as one lesion is ablated following another. The lesions also interact with each other spatially, since each lesion segment needs to be placed such that there is no effective gap permitting transmission between two lesions. Ablation plans may be adjusted, even in the course of a procedure underway, in response, for example, to unforeseen conditions and/or events, difficulties in carrying out the original ablation plan, and/or unanticipated results of ablation.

Estimators for Lesion Effectiveness

Figure 1B:
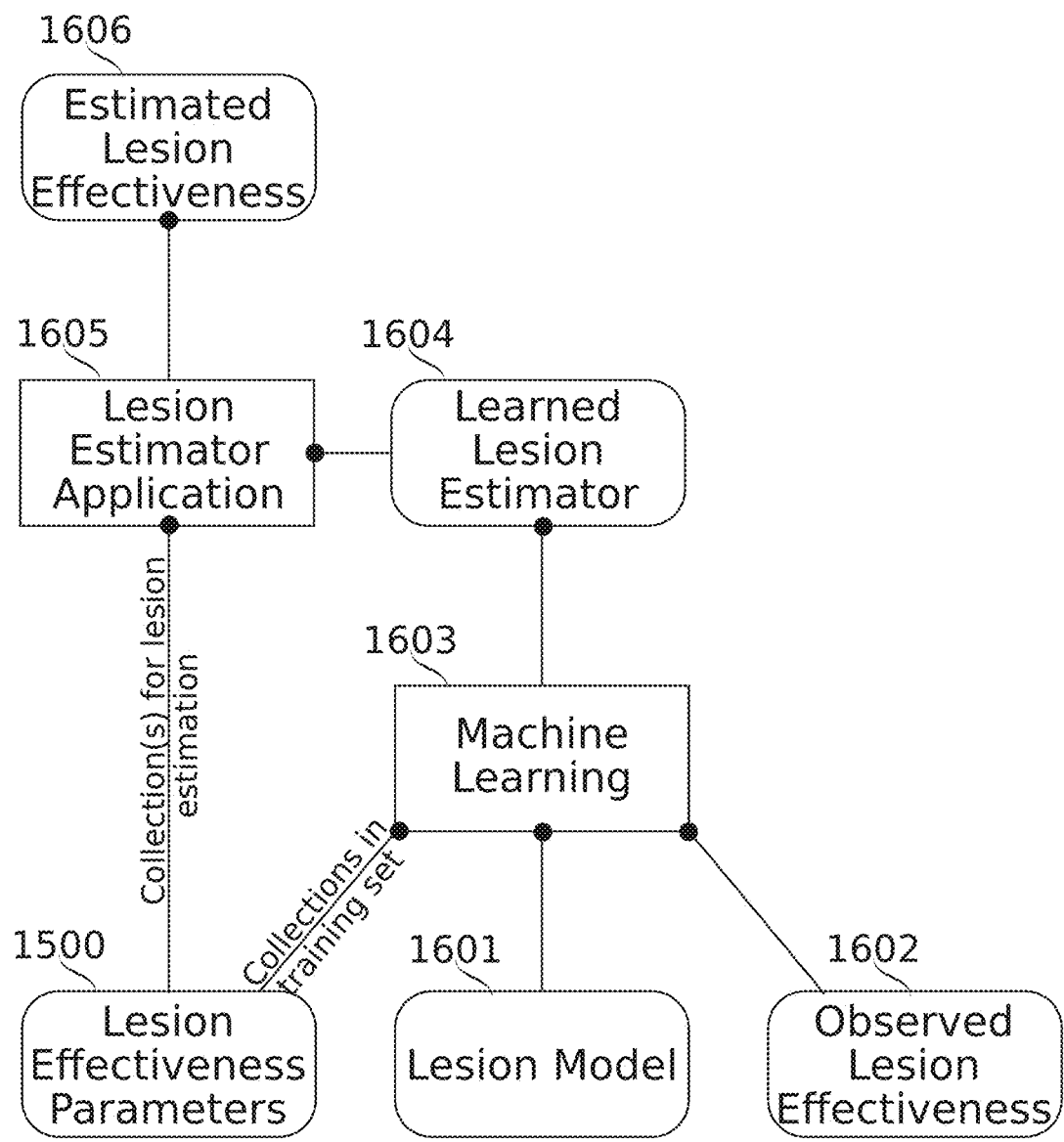
FIG. 1B is a schematic flowchart of a method of deriving and applying an estimator for predicting lesion effectiveness, according to some embodiments of the present disclosure.

Reference is now made to FIG. 1B, which is a schematic flowchart of a method of deriving and applying an estimator for predicting lesion effectiveness, according to some embodiments of the present disclosure. First, inputs to and operation of machine learning at block 1603 are described (however, it should be understood that creation of an estimator based on associations between input parameters and/or measurements and outcomes is optionally performed using a non-machine learning method, such as general-purpose statistical methods). Then application of a learned lesion estimator 1604 at block 1605 is described. With respect to FIG. 1B, "lesion" refers to an individual lesion focus or "sub-lesion", formed by operation of an ablation probe in contact with tissue, while an "ablation line" refers to a sequence or chain of such lesions.

In some embodiments, ablation treatment of a tissue region such as a tissue wall (for example, cardiac tissue of the atria) comprises the formation of a substantially continuous lesion of tissue which serves as a block to conduction. In some embodiments, the targeted region of block is along a lesion path formed from a plurality of sub-lesions arranged along it a substantially contiguous fashion.

The line of planned ablation can be defined on any suitable tissue surface; for example, within the left atrium (e.g., around one or more pulmonary veins), or within the right atrium (e.g., around one or more branches of the vena cava). For purposes of discussion, the example of an ablation line in a left atrium is described, however it is to be understood that the discussion also applies, changed as necessary, to the definition of ablation lines along other surfaces.

Optionally, the user indicates a preferred preliminary line type (e.g., by selecting from a menu a target such as "around the superior left pulmonary vein root", or another such target). Optionally, a preliminary line of planned ablation is automatically generated and/or selected based on the indication.

Effective blockage treatment of an irregular impulse conduction disease such as atrial fibrillation potentially fails when the blockage is broken or incomplete. However, the procedure for forming a blocking lesion is subject to conflicting requirements, such as the need to avoid collateral damage to non-target tissue, the difficulty of maneuvering a catheter subject to constrained degrees of freedom, and time pressure to complete the procedure as quickly as possible.

Reference is now made to FIGS. 2A-2C, which schematically illustrate aspects of lesioning to block of tissue conduction, for example for the treatment of atrial fibrillation, according to some exemplary embodiments of the present disclosure. Shown in FIGS. 2A-2B is a lesion path 54A which encircles two pulmonary veins 48 of a left atrium (a view from inside the atrium is shown).

In some embodiments, an ablation probe 10 comprising at least one ablation device 103 is moved sequentially along path 54A, ablating at a plurality of locations to create a chain sub-lesions 52 at each location. In some embodiments, ablation device 103 comprises one or more electrodes, e.g., an electrode used in RF ablation. Optionally, the electrode(s) may act as a sensing electrode for sensing dielectric properties of the tissue near it. Optionally, one or more additional electrodes may be provided for sensing dielectric properties.

In FIG. 2B, impulse 955 is shown arising from the vicinity of a pulmonary vein 48. Where it encounters a completed sub-lesion 52 (for example, at boundary 955A), conduction is stopped. However, a gap 52B potentially allows impulse portion 57 to escape into surrounding tissue, where it may contribute to an irregular heartbeat. The minimum size of a gap allowing conduction can be, for example, about 1.0 mm, 1.3 mm, 1.5 mm, or another larger, smaller or intermediate value.

Insofar as lesions may compromise a non-uniform profile through the thickness of a tissue (e.g., as for a hemi-ellipsoid or paraboloid), it should be understood that any region throughout the tissue thickness exceeding this gap width (as long as it has sufficient depth, for example, 0.55 mm, or another value of at least about 0.5 mm-2 mm, to support transmission) can serve as a pathway for impulse "escape". Thus, lesions which superficially contact one another, or even overlap-even if transmural at some region—may nonetheless (at least in principle) be sufficiently distant at some depth to allow impulse escape therebetween. However, for purposes of discussion and illustration, at least partially transmural lesions shown herein as superficially contacting are generally assumed to be close enough to block transmission therebetween at any depth, except as otherwise indicated.

Figure 5A:
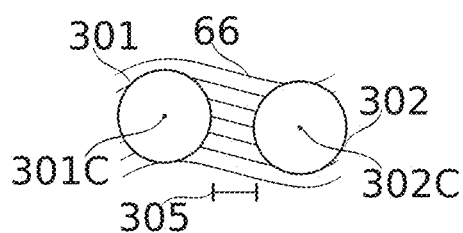
FIGS. 5A-5B schematically illustrate aspects of the planned placement of sub-lesions of a lesion line related to myocardial fiber direction, in accordance with some exemplary embodiments of the present disclosure.
Figure 5B:
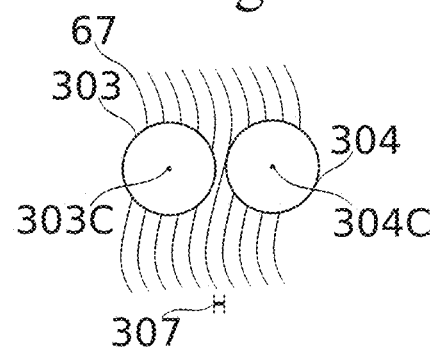

The maximum size of the gap which still prevents blockage may also depend on the structure of the underlying tissue; for example, a direction of myocardial fibers in relation the orientation of the gap (this is also discussed herein, for example, in relation to FIGS. 5A-5B). Optionally, the relevant orientation (which potentially varies through the thickness of the tissue) is selected from one or more layers in which the gap may exist.

FIG. 2C illustrates how lesion depth potentially relates to relatively effective or ineffective conduction block. Tissue region 50 is shown with a chain of sub-lesions 52, 52A, 52D, 52C already formed. The various depths of these lesions are schematically outlined as dotted line paraboloids 53, 53A, 53D, 53C.

Electrode 103 is shown in contact with a surface of tissue 50, over lesion and targeted tissue area 52C. Here, the lesion is transmural, to the degree that it has begun to spread across the opposite surface of tissue 50 at region 53C. Lesion 52A is also a deep lesion, but the degree of transmurality is lower (for example, a small distance 53A has been left). This may not be a reason for concern, if gap 53A is too small to allow impulse conduction. However, at lesion 52D, the lesion is too shallow, and gap 53D is sufficiently large to allow impulse portion 57 to pass through it. In some embodiments, a transmurality gap of about 0.55 mm or smaller is considered small enough to prevent impulse escape, depending also in part on the width of the gap.

Although ablation is generally described herein with respect to ablation of an atrial wall for the treatment of atrial fibrillation, it should be understood that the descriptions also apply, changed as necessary, to the planning of ablation in other tissues; for example: neural tissue, tumor tissue (for example, cancer), other abnormal growth tissue such as warts, skin tissue, mucous membrane, or another tissue.

Figure 3A:
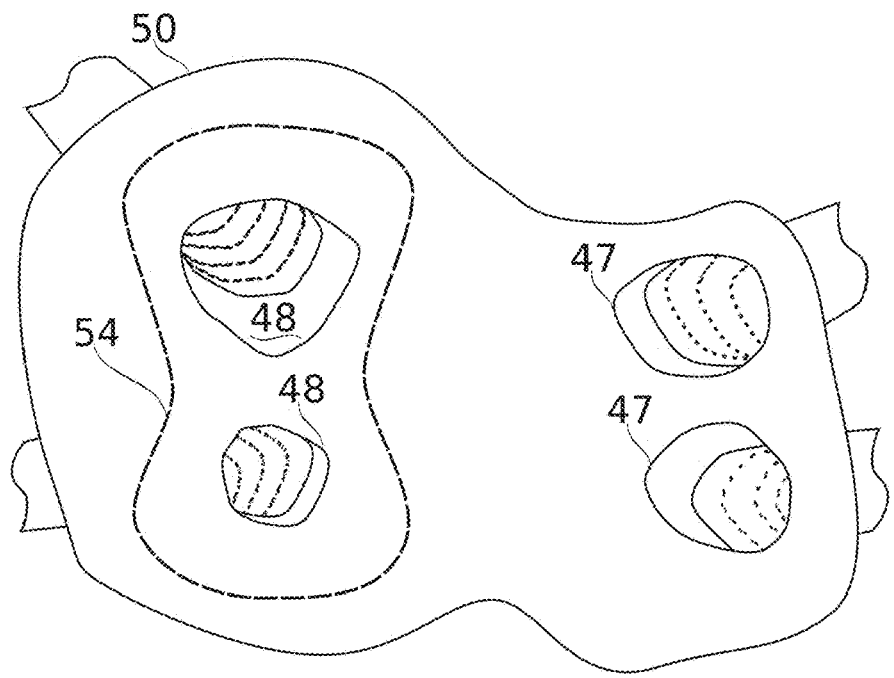
FIG. 3A is a schematic illustration of a tissue wall of a left atrium, including roots of left and right pulmonary veins, and a preliminary line of planned ablation, in accordance with some exemplary embodiments of the present disclosure.

Reference is now made to FIG. 3A, which is a schematic illustration of a tissue wall 50 of a left atrium, including roots of left and right pulmonary veins 47, 48, and a preliminary line of planned ablation 54, in accordance with some exemplary embodiments of the invention.

Optionally, preliminary line of planned ablation 54 encircles both left pulmonary veins, for example as shown. Optionally, the line of planned ablation serves as a basis for further modifications which result in a final ablation line which satisfies certain criteria of safety and/or effectiveness.

Figure 3B:
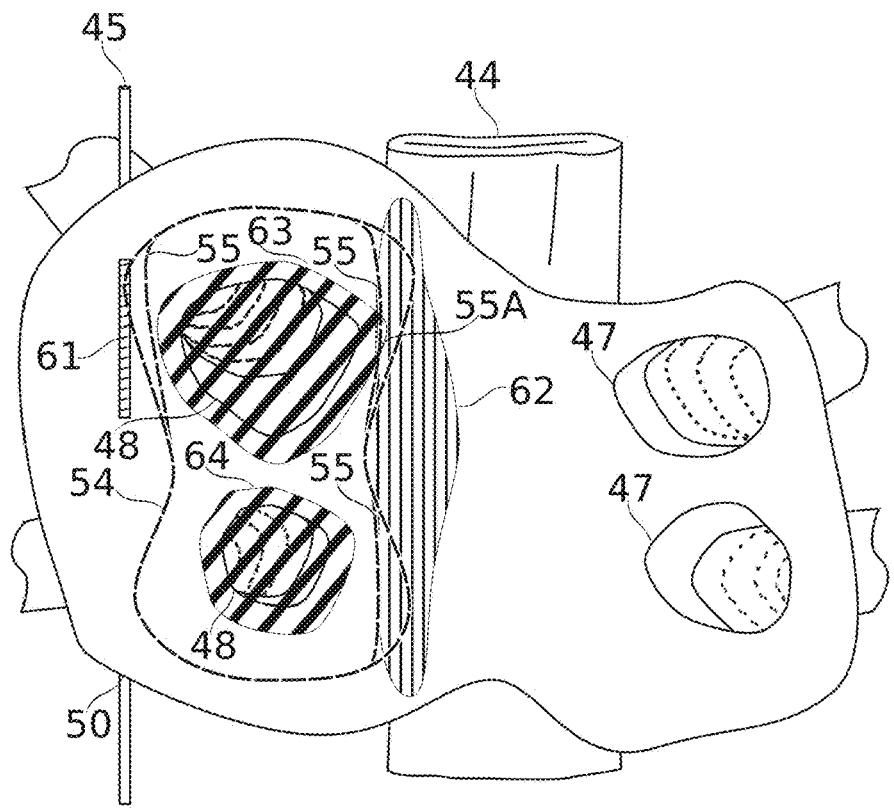
FIG. 3B is a schematic illustration of tissue wall, together with a section of a phrenic nerve, an esophagus, and roots of pulmonary veins, each of which is potentially vulnerable to lesion damage due to proximity with tissue wall, in accordance with some exemplary embodiments of the present disclosure.

Reference is now made to FIG. 3B, which is schematic illustration of tissue wall 50, together with a section of a phrenic nerve 45, an esophagus 44, and roots of pulmonary veins 47, 48; potentially vulnerable to lesion-damage around preliminary line of ablation 54 due to proximity with tissue wall 50 at regions 61, 62, 63, or 64; in accordance with some exemplary embodiments of the invention.

In some embodiments, a planned ablation of one tissue (e.g., tissue wall 50) involves potential risk of damage to one or more adjoining tissues. For example, thermal ablation (e.g., by RF energy application) which enters into region 62 of tissue wall 50 potentially also induces heating in esophagus 44 which could lead to damage. Region 61, adjacent to a portion of phrenic nerve 45, is another region of potential risk; damaging the phrenic nerve can lead to partial respiratory paralysis. In some embodiments, lesion placement criteria exclude and/or limit lesioning from entering certain regions of the lesioned surface itself. Regions 63 and 64 are defined, for example, to exclude lesions from entering the ostia of the pulmonary veins.

Exclusion may be defined such that no heating or cooling of an at-risk tissue can rise above (or fall below) a certain temperature threshold, e.g., according to a simulated ablation operation. In some embodiments, the temperature threshold is, for example, about 50° C., 55° C., 58° C., 60° C., 65° C., 70° C., 75° C., or another larger, smaller or intermediate temperature. Optionally, a functional criterion is used: for example, a plan which includes heating for more than T seconds at energy Y by a probe within X mm is preferably excluded. Optionally, values for T, Y and/or X are chosen based on general simulations and/or experimental data, for use as heuristics in the cases of actual patient treatments. For example, T is varied between about 15 seconds to about 45 seconds; Y varies between about 15 W and 30 W, and/or X varies between about 5 mm-10 mm. Use of heuristic criteria has the potential advantage of bypassing at least some of the computational load of an individualized simulation.

In some embodiments, lesioning in a risky area is made potentially safer by controlling parameters such as ablation power and/or ablation timing, optionally in addition to controlling the parameter of ablation probe placement. Conversely, there may be regions where the risk of collateral damage is relatively low. For example, relatively low thermal conductivity of adjacent tissue (e.g., air-filled lung tissue) potentially allows more aggressive lesioning of heart wall tissue, which has a potential advantage for speed of lesioning.

Figure 3C:
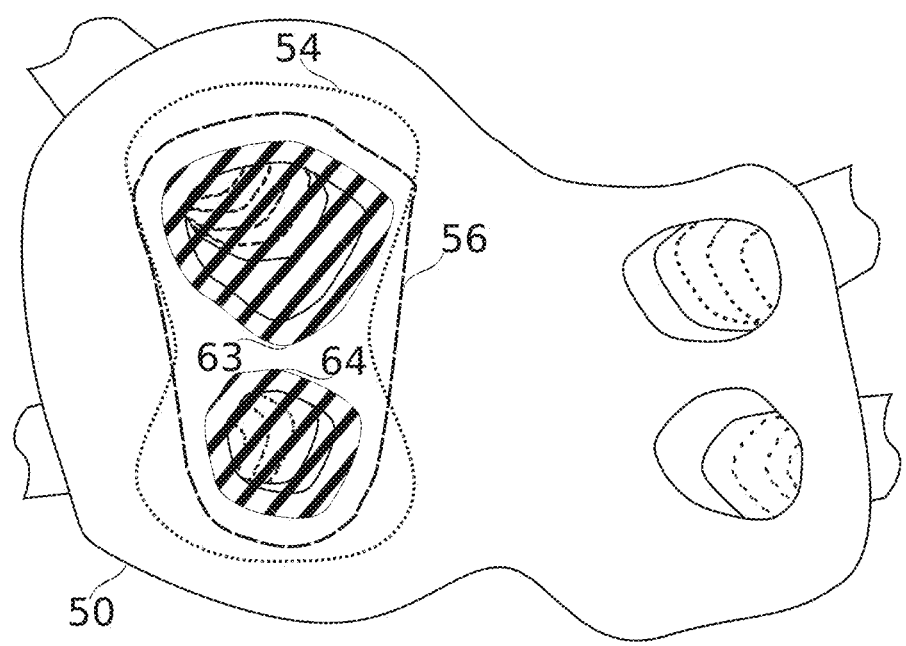
FIG. 3C is a schematic illustration of an alternative line of planned ablation, in accordance with some exemplary embodiments of the present disclosure.

The line of planned ablation 55 shown in FIG. 3B is minimally disturbed from the preliminary line of planned ablation 54 for applying protective criteria, without also minimizing path length. However, reference is now made to FIG. 3C, which is a schematic illustration of an alternative line of planned ablation 56, in accordance with some exemplary embodiments of the invention. In this instance, preliminary line of planned ablation 54 is shown aggressively optimized for reduced length as alternative line of planned ablation 56. Optionally, preliminary line of planned ablation 54 is "shrunk" until some sub-lesions produced therealong would just reach to the limit of vein ostium protection regions 63, 64. In some embodiments, lengthening the path by over-shrinkage is prevented; the effect is as though a rubber band were extended between sub-lesions which are not in direct contact with the vein ostium protection regions 63, 64.

In FIG. 3B, line of planned ablation 55 is shown adjusted from preliminary line of planned ablation 54 by diversions which pull the line centrally away from regions 61 and 62 at which ablation is indicated to accompany a potential risk for collateral damage.

Figure 3D:
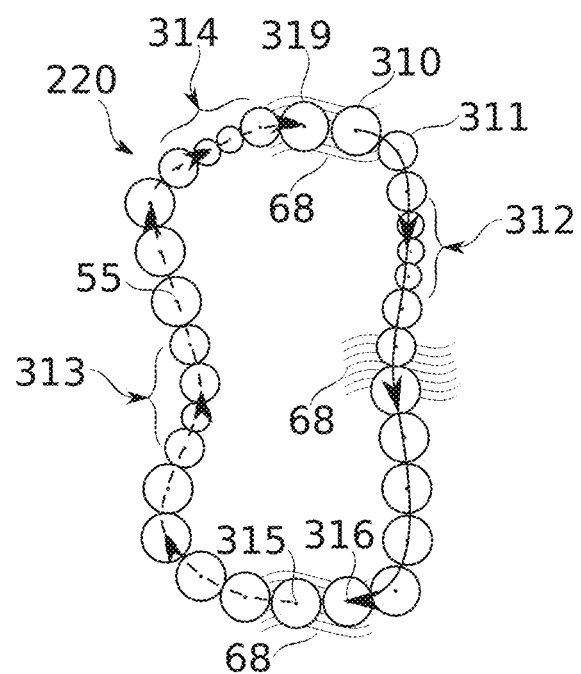
FIG. 3D is a schematic illustration highlighting details of a planned set of sub-lesions of a lesion line, and their traversal along a line of planned ablation, in accordance with some exemplary embodiments of the present disclosure.
Figure 3E:
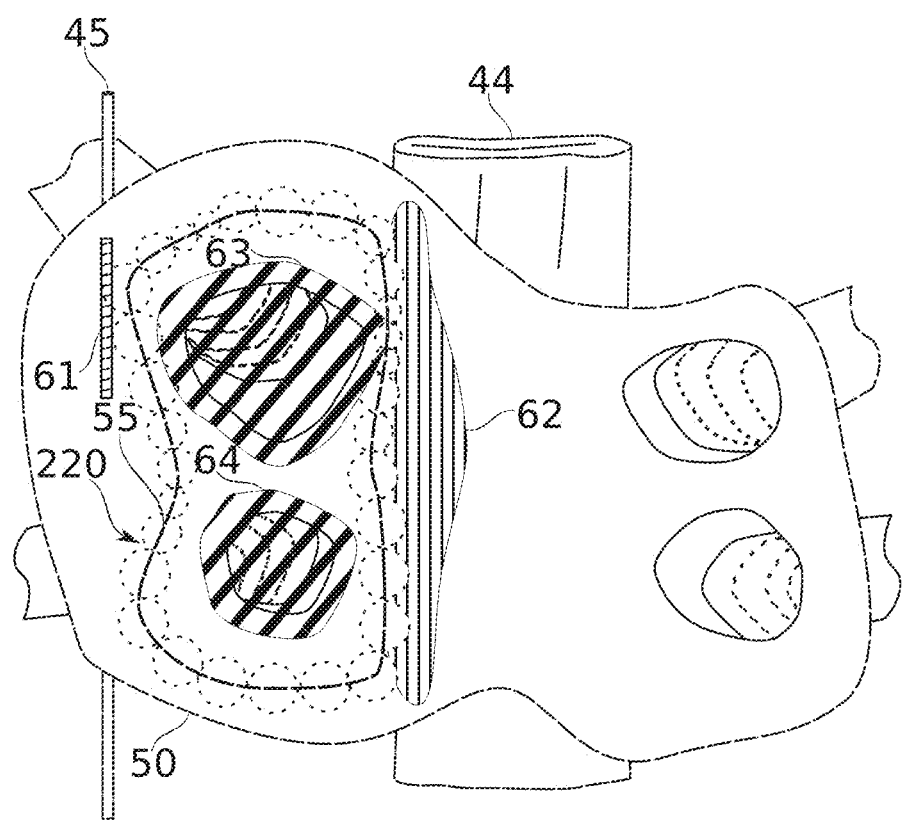
FIG. 3E is a schematic illustration of a planned set of ablation sub-lesions for ablating along line of planned ablation, in accordance with some exemplary embodiments of the present disclosure.

Continuing reference is made to FIG. 3D, and also to FIG. 3E, which is a schematic illustration in a wider anatomical context of the planned set of ablation sub-lesions 220 for ablating along line of planned ablation 55, in accordance with some exemplary embodiments of the invention.

It is noted that most of the sub-lesion locations marked (e.g., sub-lesion 310) are relative large in diameter. Optionally, this reflects a default ablation setting, wherein a full-power, full-duration ablation is planned to be carried out at the given position. This may be appropriate, for example, when the tissue wall 50 is relatively thick, and there is a relatively low risk of serious collateral damage which allows proceeding rapidly. Somewhat smaller sub-lesion sizes are shown, for example, at sub-lesion 311, and in particular through regions 312, 313, and 314. In some embodiments, smaller sub-lesions are formed, for example, by use of a lower ablation power, and/or by use of a shorter lesioning dwell time. Smaller lesions through region 312, for example, optionally reflect an increase in care to avoid damage to the esophagus (compare, for example, to the positions of ablation sub-lesions 220 in FIG. 3E relative to regions 62 and 63). Optionally, smaller lesions through regions 313 and 314 reflect the presence of another constraint or condition; for example, a thinner tissue wall thickness, and/or a locally higher rate of perfusion which reduces the ability to heat nearby tissue.

Although sub-lesions 220 are drawn as abutting circles, it is to be understood that an ablation plan optionally overlaps sub-lesion areas to help ensure that deeper tissue is not subject to impulse-transmitting gaps. Optionally, sub-lesion shapes are different than circular, due, for example, to oblique angles of contact between the ablation probe 10 and the tissue wall. Optionally, an ablation probe is slowly dragged across a surface, leaving a more streak-like sub-lesion. Another factor which can affect sub-lesion shape is the interaction between heating delivered at different sub-lesion locations.

Figure 8A:
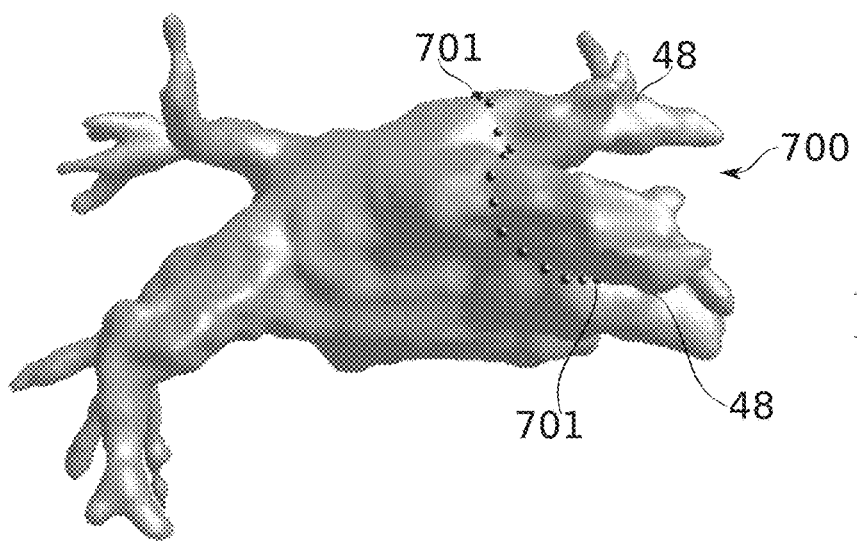
FIGS. 8A-8C illustrate the 3-D display of a lesion plan for a left atrium, in accordance with some exemplary embodiments of the present disclosure.
Figure 8B:
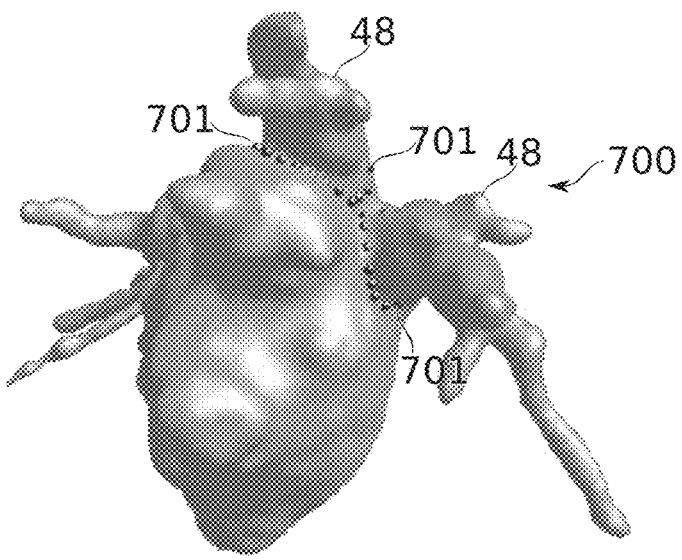
Figure 8C:
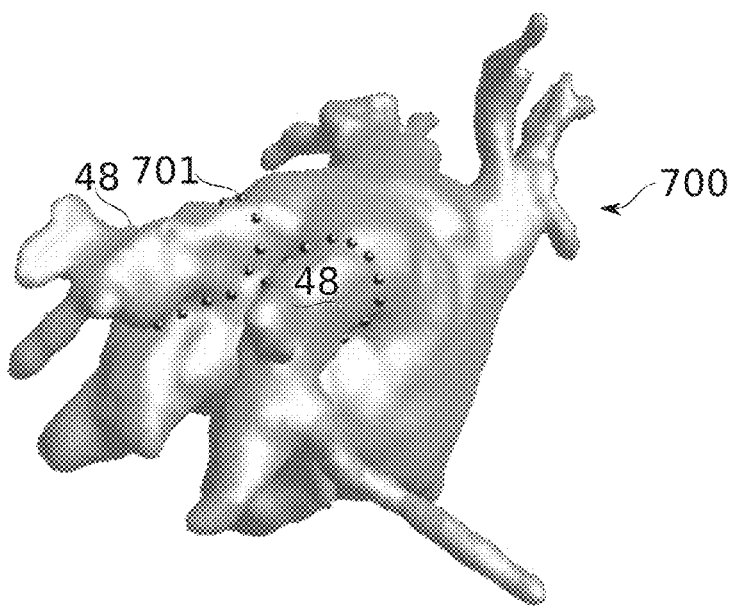

Reference is now made to FIGS. 8A-8C, which illustrate the 3-D display of a lesion path for a left atrium 700, in accordance with some exemplary embodiments of the invention.

In some embodiments, the lesion path is shown to a user by use of a 3-D display. FIGS. 8A-8C illustrate one such plan display. A 3-D model of a left atrium 700 (porcine, in this example) is shown from three viewpoints. Sub-lesion loci are indicated by the trails of dark marks 701 (modeled as embedded spheres, for example). In this case, the lesion lines are shown extending around portions of the roots of the inferior vena cava 48.

In some embodiments, a goal of ablation is to create a blockage lesion having a substantially transmural extent. To meet this goal, thicker tissue walls potentially require application of more lesioning energy (e.g., at a higher power and/or for a longer time) than thinner walls. Over-lesioning, however, can weaken the tissue, and/or lead to damage to surrounding tissue. Over-lesioning can also extend lesioning time unnecessarily. In some embodiments, tissue thickness throughout the region targeted for lesioning is characterized, for example based on analysis of anatomical images of the individual patient (obtained, e.g., by MRI, CT, or another method), and/or based on dielectric measurements.

Prior Inputs to Machine Learning

In some embodiments, the flowchart block marked 1500 comprises a plurality of "collections" of lesion effectiveness parameters 1500. Each such collection in turn comprises a heterogeneous set of data inputs relating to a particular lesion (that is, a lesion formed at a focus by a single application of ablation energy; corresponding, for example, to the sub-lesions 52 of FIGS. 2A-2C). The particular lesion is formed (and/or is planned to be formed) by the operation of an ablation modality (e.g., radio frequency ablation, cryoablation, microwave ablation, laser ablation, irreversible electroporation, substance injection ablation, and high-intensity focused ultrasound ablation) acting on tissue which is targeted for ablation. The data inputs of a collection of lesion effectiveness parameters 1500 may include indications of conditions of formation of the lesion; for example, lesion placement, ablation tool settings governing lesion formation (such as ablation power, dielectric quality of contact, angle of contact, force of contact, and timing of ablation), and/or tissue conditions within which the lesion is situated. Lesion effectiveness parameters 1500 may include lesion measurements such as dielectric measurements, calculated results of ablation, and/or other indications of the structure of an ablation lesion (e.g., depth, linear size, areal size, and/or volume of tissue). Optionally, lesion effectiveness parameters 1500 include other data; for example: patient data parameters, and/or previously acquired ablation data for the same patient.

As used herein, dielectric measurements may include any measured dielectric parameters, for example: impedance, voltage etc. Dielectric measurements may be obtained by one or more electrodes (for example: electrodes 1114 or electrodes 103) and/or by one or more sensors (for example: sensors 1128). Dielectric measurements may be obtained by one or more electrodes and/or one or more sensors provided on a probe of the ablating catheter (for example: catheter 1116). Dielectric measurements may be obtained by one or more sensors provided on a dedicated intra-body probe, e.g., used solely for such dielectric measurements). Dielectric measurements may be obtained at a single frequency or at a plurality of frequencies. In some embodiments, dielectric measurements include measurement at various frequencies, e.g., from about 10 kHz to about 1 MHz. In some embodiments, dielectric measurements may include complex values. In some embodiments, dielectric measurements may include impedance measurements including measurements of impedance between different electrodes on the ablation catheter (e.g., between a tip electrode on a probe of the ablation catheter and another electrode on the same catheter), between one or more electrodes on the ablation catheter and one or more electrodes on another catheter, and/or between one of more of the ablation electrodes and one or more body surface electrodes.

Optionally, patient data parameters may include the medical state of the patient; for example, medications the patient is taking (e.g., which may affect the ionic concentration of the tissues of the patient, affecting the electrical and/or thermal parameters), and a history of previous treatments (e.g., which may help predict the effects of the current treatment). Additional examples of patient data parameters are described below.

Moreover, the inputs of each collection of lesion effectiveness parameters 1500 at least potentially indicate (individually and/or in aggregate) information about the "effectiveness" of the particular lesion to which they relate. In some embodiments of the present invention, "effectiveness" is defined in relation to targeted outcomes of cardiac ablation treatments for atrial fibrillation (AF). In AF ablation treatments, an effective lesion is a lesion in a cardiac wall (i.e., an atrial wall) which substantially blocks electrophysiological impulse transmission from passing through, over, and/or under it (that is, an effective lesion provides transmural electrical isolation). In some embodiments, persistence (or permanence) of the lesion and/or its blocking characteristics is a criterion of effectiveness. Other definitions of "effectiveness" applicable in some embodiments of the present invention are described hereinbelow. In some embodiments, effectiveness relates to conditions of safety. Optionally, for example, "effectiveness" is at least partially defined as comprising avoidance of some particular outcome, for example, avoiding lesioning of the esophagus, the phrenic nerve, and/or the venous roots, each of which can potentially lead to serious complications. Optionally, an estimator is used for any combination of "effectiveness" conditions; additionally or alternatively, a plurality of estimators are used, which optionally each cover a single criterion of effectiveness, or a plurality of effectiveness criteria.

At block 1603, in some embodiments, a plurality of collections of lesion effectiveness parameters 1500 is provided as a training set data for use in one or more machine learning methods, in order to generate a learned lesion estimator 1604 (herein, black dots mark the receiving side of a connecting line). The example of "machine learning" is used herein as an example of a method of creating an estimator, and should not be considered limiting: alternatives include, for example general purpose statistical methods and/or estimator definition based on theoretical equations accounting for observed correlations. In some embodiments, training set data used in generating the learned lesion estimator 1604 are obtained in vivo. In some embodiments, at least part of the training set data used to generate the learned lesion estimator are obtained in vitro, for example based on lesioning of porcine heart wall.

Feedback Inputs to Machine Learning

In some embodiments of the invention, for each collection of lesion effectiveness parameters 1500 in the training set data, there is also provided as input to block 1603 a corresponding data collection indicating observed lesion effectiveness 1602. For example, the observed lesion effectiveness optionally includes a measurement showing one or more of the following:

acute electrical isolation is established by the lesion at the end of the ablation procedure;

persistent electrical isolation remains for at least 5 days, 30 days, 60 days, 90 days, or another longer, shorter, or intermediate duration after the end of the ablation procedure;

asymptomatic
hospitalization
survival
AF burden <5%
- a fibrotic area corresponding to the lesion persists for at least 5, 30, 60, 90, or another longer, shorter, or intermediate period after the end of the ablation procedure; and/or
- the patient is disease free for at least 1 month, 3 months, 6 months, 1 year, 2 years, 5 years, or another longer, shorter or intermediate period after the end of the ablation procedure.

In some embodiments, lesion effectiveness is a local measure. Thus, the more global conditions just listed ("disease free", for example) may not apply to such embodiments, since on an individual lesion analysis, it may not be clear on which (failed) lesion a reappearance of disease should be blamed. There may not even be a single failed lesion as such, only a failure to place otherwise adequate lesions correctly. However, in some embodiments (e.g., FIG. 4B), at least some local context is taken into account, so that if every lesion is estimated as effective, then the overall ablation line should normally be effective as well. In some embodiments, observed lesion effectiveness relates to safety—for example that the lesion was or was not associated with a complication such as damage to the esophagus, damage to the phrenic nerve, damage to the venous roots, and/or a risk-associated event during ablation such as charring or "steam pop". Steam pop is a term for a condition wherein rapid expansion of steam during an ablation creates an audible "pop"; this is associated in the literature with a risk of complications such as heart wall perforation.

In some embodiments, data indicating observed lesion effectiveness may be obtained by the same catheter that was used to form the ablation. For example, a probe of an RF ablation catheter is operated to ablate tissue, and then electrodes of the same catheter are used to measure potential (e.g., in high frequency electrical fields) induced in the vicinity of the ablation. From these measurements, impedance properties indicating lesion state are optionally calculated. In some embodiments, the impedance properties in turn indicate dielectric properties of tissue that are changed as a result of tissue ablation. Dielectric properties and/or impedance are optionally interpreted as indicating local tissue state and in particular, local tissue state(s) as being permanently lesioned (e.g., converted to fibrotic tissue), edematous but not fibrotic, and/or healthy. Data provided as a collection of observed lesion effectiveness data 1602 is optionally expressed in any or all of these formats (voltages, impedances, dielectric parameters, and/or tissue state(s) inferred therefrom). Optionally, another measure of observed lesion effectiveness is provided, for example, measurements of electrical isolation (e.g., lack of impulse conduction across the lesion), or clinical observation that disease is absent.

Model Input to Machine Learning, and Pre-Processing of Inputs

In some embodiments, the machine learning of block 1603 proceeds on the basis of an assumed lesion model 1601. Optionally, lesion model 1601 may be very simple, and simply hypothesizes for the machine learning of block 1603 a correlation (naïve as to underlying structure) between the prior inputs of lesion effectiveness parameters 1500 and the feedback inputs of observed lesion effectiveness 1602. However, it may be a potential advantage to at least partially structure inputs. The structure can be provided as part of lesion model 1601, and/or by pre-processing of data provided as inputs. For example, inputs from the side of the lesion effectiveness parameters 1500 are optionally pre-processed to be expressed in terms of lesion size (diameter and/or depth, for example). Additionally or alternatively, such measurements are structured by the lesion model itself into indications of lesion size (e.g., machine learning is applied to a model equation operating on the lesion effectiveness parameters in one or more combined terms, rather than only in terms each comprising a different raw lesion effectiveness parameters). Discussion of FIG. 4A describes this and other levels of structuring that are optionally used in some embodiments of the present invention.

On the feedback side, pre-interpretation of raw measurements indicating lesion effectiveness (e.g., interpretation of electrical field measurements such as dielectric measurements to identify local tissue state) provides a potential advantage by reducing complexity of the data space (and potentially noise in the data) before applying machine learning to it. However, there is a potential disadvantage in over-simplifying the data in observed lesion effectiveness 1602 by pre-interpreting, as this can reduce or destroy correlations latent in the raw data. Optionally, use of pre-processing enables creating estimators which are applicable to different types of raw input. For example, part of the difference between simulations of lesion size (e.g., before lesioning) and measurements of lesion size after lesioning can be abstracted away by making lesion size itself one of the inputs in the lesion effectiveness parameters 1500. That has the potential advantage of allowing comparison of predictions from a planned procedure with predictions from actual procedure results, for example.

In some embodiments, the raw measurements indicating lesion effectiveness (e.g., electrical field measurements such as dielectric measurements) may be used as lesion effectiveness parameters 1500 (e.g., without any calculations) and may be input as training set data.

Learned Lesion Estimator

After the above-described inputs are suitably defined and received for a plurality of lesions (e.g., 50, 100, 1000, or another larger, smaller, or intermediate number of lesions), machine learning at block 1603 uses of one or more machine learning methods, to produce a learned lesion estimator 1604. Examples of machine learning methods used in some embodiments of the present invention include, for example: decision tree learning, association rule learning, an artificial neural network, deep-learning artificial neural network, inductive logic programming, a support vector machine, cluster analysis, Bayesian networks, reinforcement learning, representation learning, similarity and metric learning, and/or another technique taken from the art of machine learning. In some embodiments, the estimator output (e.g., estimated lesion effectiveness) may include a binary prediction (e.g., +1 or −1). In some embodiments, the estimator output (e.g., estimated lesion effectiveness) may include a probabilistic output, e.g., between zero and one (e.g., a dynamic score). Such embodiments may be advantageous when using estimator during an ablation procedure, e.g., to facilitate a user decision whether to proceed or complete the procedure and/or to adjust the ablation plan.

In some embodiments, the learned lesion estimator 1604 comprises a set of learned weights applied to terms of lesion model 1601.

Application of the lesion estimate at block 1605 comprises plugging into the model appropriate values from other collection of lesion effectiveness parameters 1500, and calculating the result. The result is produced as an estimated lesion effectiveness 1606. Other collections of ablation line effectiveness parameters 1500 may refer to ablation line effectiveness parameters 1500 collected after learned ablation line estimator 1604 was created, e.g., ablation line effectiveness parameters 1500 collected in run-time during a medical procedure. Other collections of ablation line effectiveness parameters 1500 may include dielectric measurements measured run-time during a medical procedure. Such dielectric measurements may be used as inputs to learned lesion estimator 1604 to obtain estimated lesion effectiveness 1606.

It should be noted that learned ablation line estimator 1604 may be updated and/or adjusted (also referred to as refreshed) based on such other collections of ablation line effectiveness parameters 1500. Estimated lesion effectiveness 1606 may be presented to a user (e.g., physician) during a medical procedure. Such Estimated lesion effectiveness 1606 may be used to adjust an ablation plan.

In some embodiments, the estimated lesion effectiveness 1606 is expressed in the same terms as used by lesion model 1601 for learning. Optionally, the estimated lesion effectiveness 1606 may also be accompanied by an estimate of the certainty of the prediction, for example, based on statistically determined specificity and/or sensitivity. Optionally, post-processing is applied to convert the estimated lesion effectiveness 1606 into another form. For example, the feedback input in the observed lesion effectiveness 1602 may not itself encode a spatial extent of the region electrically isolated by a particular lesion; but rather, for example, it may simply indicate that the electrical isolation is sufficient to maintain disease prevention. Since this implies that the lesion is transmural, it is possible, optionally, to infer at a later stage that the depth of the lesion is about the same as the thickness of the tissue. Similarly, the positions and sizes of adjoining lesions optionally provide post-processing constraints on lesion diameter. It should be understood that it is often possible to alternatively make such adjustments in a stage of pre-processing (e.g., convert "successful block" to size constraints in the feedback input indicating observed lesion effectiveness 1602), and/or to account for them in lesion model 1601 itself (e.g., define model 1601 to output an estimate comparing lesion depth to atrial wall width, rather than a binary "successful/unsuccessful" result).

Stand-Alone Lesion Effectiveness Estimator

Figure 4A:
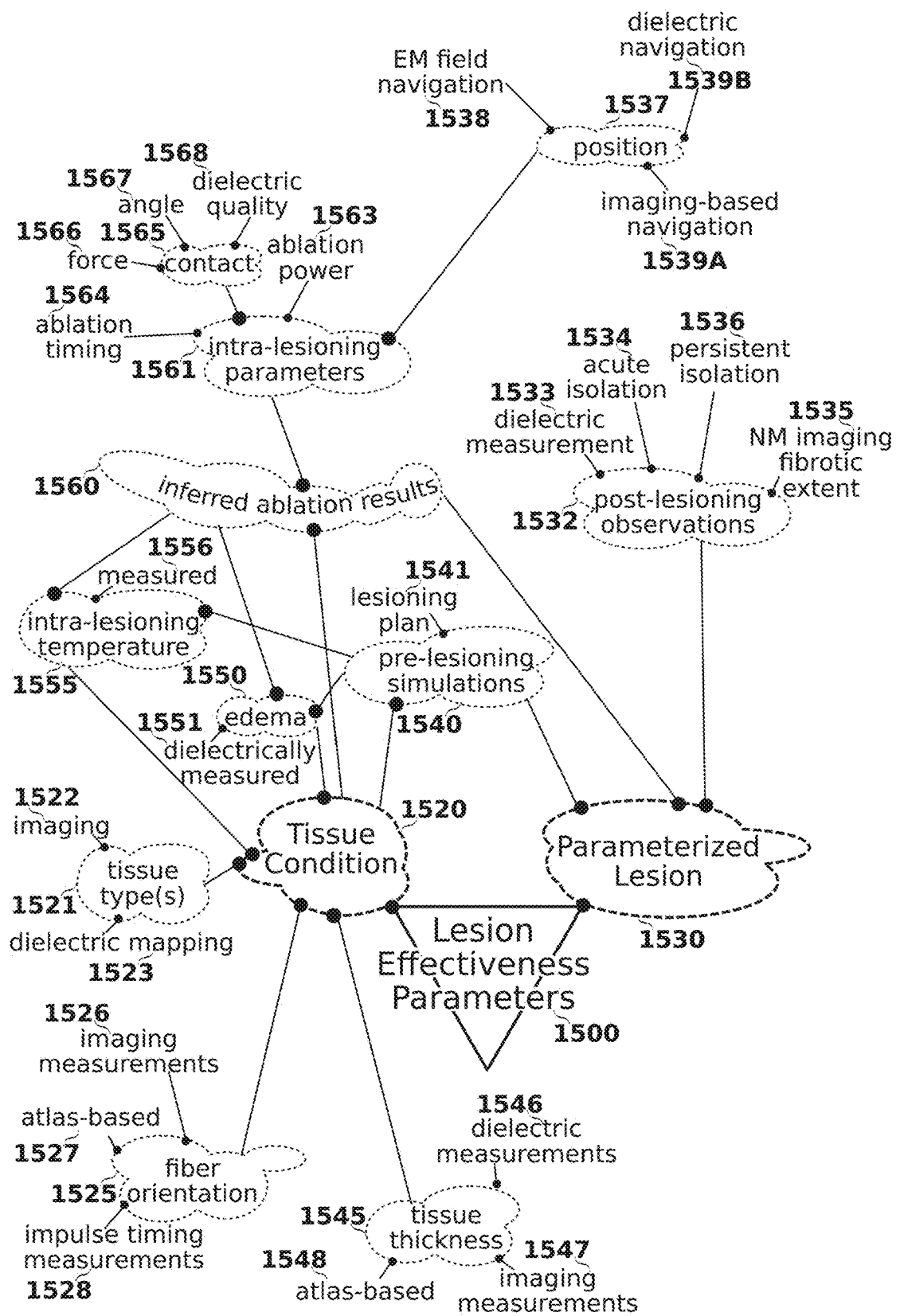
FIG. 4A schematically represents a range of options for prior inputs to a lesion effectiveness estimator and/or for machine learning of the estimator, comprising parameters potentially relating to lesion effectiveness, according to some embodiments of the present disclosure.

Reference is now made to FIG. 4A, which schematically represents a range of options for prior inputs to a lesion effectiveness estimator and/or for machine learning of the estimator, comprising parameters potentially relating to lesion effectiveness, according to some embodiments of the present disclosure.

The number of possible separate inputs to a collection of lesion effectiveness parameters, in some embodiments, is both large and optionally variable. The inputs listed in FIG. 4A may be viewed as providing a menu of examples of parameters, from which any suitable subset is optionally used. Optionally, another parameter source not shown among those in the FIG. 4A may be used.

The broadly hierarchical (mostly branched, but in some places looping) arrangement by which optional inputs are shown in FIG. 4A is primarily used as a guide to help organize the descriptions that follow. Terminal nodes (terms without borders) represent numerous types of basic inputs (e.g. measurements, settings, and outside data such as anatomical atlas data). Nodes surrounded by thin cloud-shaped borders list intermediate organizational concepts that link the basic inputs (and/or other organizational concepts) as alternative and/or complementary contributions to the full collection of lesion effectiveness parameters 1500, as detailed for each. Optionally (as indicated in the more detailed descriptions following), some of the cloud-bordered nodes represent higher level abstractions used in the lesion effectiveness parameters in place of one or more basic inputs.

Next to the triangle that indicates the root of the hierarchy of lesion effectiveness parameters 1500 are two clouds with thicker borders. These clouds define a basic conceptual division of the lesion effectiveness parameters into two: parameters indicating information about size and/or position of the lesion itself (parameterized lesion 1530, which may be said to be characterized by lesion parameterizing data), and parameters indicating information about the tissue environment in which the lesion is placed (tissue condition 1520).

Apart from the organization just described, the parameters of FIG. 4A belong to one or more of three time stages:

Pre-lesioning Inputs indicate, for example, results of planning activities (ablation line definition, pre-ablation simulations of ablation extent, etc.)

Intra-Lesioning Inputs include, for example, measurements taken and operational parameters used during a lesioning procedure (including parameters optionally measured immediately after lesioning but before the overall procedure ends; for example: dielectric measurements)

Post-Lesioning Inputs include, for example, clinical observations in the period after the procedure ends (day to years), post-procedure imaging, and/or follow-up catheterization procedures.

For some parameters, stages are explicitly mentioned in FIG. 4A (e.g., as pre-lesioning simulation 1540, intra-lesioning parameters 1561 indicative of the conditions of formation of a lesion, and post-lesioning observations 1532). Staging relevant to other inputs is mentioned where those inputs are described. These three stages of parameter availability are also discussed with respect to FIG. 11, in the context of their relationship to each other, and to different future times for estimation. Starting now from the node labeled parameterized lesion 1530: In some embodiments, the lesion is parameterized based on one or more of pre-lesioning simulations 1540, post-lesioning observations 1532, inferred ablation results 1560, and/or any of the other parameters which are shown feeding into these nodes. Inferred ablation results 1560 may include one or more inferences of a tissue state from dielectric measurements and/or any manipulation (such as mathematical manipulation) on such dielectric measurements). Inferred ablation results 1560 may include one or more inferred results inferred from dielectric measurements by analytical calculations and/or machine learning techniques, for example, type of tissue (healthy or fibrotic, for example), size of a lesion, thickness of tissue, and/or quality of contact with tissue.

In some embodiments, the lesion is parameterized non-geometrically in the collection of lesion effectiveness parameters 1500 supplied to an estimator. For example, a dielectric measurement 1533 optionally provides information about how much local tissue in the region of a measurement electrode has been lesioned, without necessarily providing information about how the lesion is shaped. Potentially, a non-geometrical parameterization may still provide enough information for machine learning to converge on an estimator linking the lesion parameterization to an estimated lesion effectiveness.

Additionally or alternatively, in some embodiments, the lesion is parameterized as a geometrical object having a well-defined shape. For example, a geometrical parameterization of lesion shape optionally defines at least a lesion depth and/or a proximal diameter (diameter of a lesion at the side directly in contact with the lesioning device, such as a probe of an intra-body catheter). Optionally, these parameters are incorporated into a definition of a geometrical solid representing the shape of the lesion; for example, a frustum of a paraboloid, ellipsoid, cone, or another shape. Parameterization of lesions as geometrical shapes, though potentially subject to estimation errors of its own, has the potential advantage of being interconvertible between outputs of pre-lesioning simulation 1540, inferred ablation results 1560 (and/or intra-lesioning parameters 1561), and post-lesioning observations 1532. Optionally, this may allow the same estimator to be used on data from different original sources. Additionally or alternatively, a non-spatial "common parameterization" may be used; for example, a spatial definition of a lesion determined by simulation is optionally re-parameterized by the results of simulated "measurements". Optionally, re-parameterization is be used to convert lesion effectiveness parameters from in vitro studies into lesion effectiveness parameters more convenient for direct in vivo use, and/or conversely.

Each of the three main lesion parametrizing data stages is now discussed in turn.

In some embodiments, pre-lesioning simulations 1540 produce parameterized descriptions of lesions which are planned to be made during an ablation procedure. Pre-lesioning simulation 1540 may comprises simulations such as EM (Electro-Magnetic) simulation; e.g., RF absorption simulation, and/or thermal simulation on a simulated tissue to be treated. The pre-lesioning simulations 1540 may be based on a lesioning plan 1541 which may describe where and how ablations are to be made, and optionally modulated by relevant parameters of tissue condition 1520 (e.g. tissue thickness 1545, state of edema 1550, tissue type(s) 1523, fiber orientation 1525, and/or intra-lesioning temperature 1555, each further described below). As examples of plan modulation, ablation intensity (power, and/or time of ablation energy deliver) is optionally increased for a larger tissue thickness, and/or reduced for a higher than expected intra-lesioning temperature. Optionally, fiber orientation modulates how close together lesions are planned (lesions placed adjacent along fibers are potentially less prone to gap formation at increasing distances than lesions where fibers are oriented to pass between the adjacent lesions). Tissue having developed edema may require more energy to successfully ablate, and/or may be preferably avoided in preference to another ablation location and/or strategy. Tissue of a type which is already fibrotic may not require additional ablation.

Optionally, the pre-lesioning simulation 1540 is produced as part of creating the lesioning plan 1541 in the first place. Insofar as the pre-lesioning simulation optionally comprises spatially defined simulations such as an RF absorption simulation and/or thermal simulation, it may be relatively straightforward to define the parameterized lesion 1530 in terms of geometrical shape.

In some embodiments, parameterized lesion 1530 is based on inferred ablation results 1560. Similarly as with pre-lesioning simulations 1540, the inferred ablation results may estimate the effects of parameters used during ablation, optionally modulated by the parameters of tissue condition 1520. However, instead of choosing ablation parameters from a lesioning plan 1541, the intra-lesioning parameters 1561 used in actual ablation (and, accordingly, also indicative of the conditions of formation of a lesion) are used. Examples of intra-lesioning parameters 1561 include ablation probe contact 1565, ablation power 1563, ablation timing 1564, and optionally other ablation parameters not shown, such as phase and/or frequency. In some embodiments, contact 1565 is measured and/or estimated based on force measurements 1566 (e.g., measurements by one or more force sensors on the ablation probe), dielectrically-measured quality of contact 1568, and/or angle 1567 of probe contact with tissue, which can be measured, for example, by comparing readings from a plurality of force sensors, and/or based on indications of dielectrically measured quality of contact. Dielectric measurement of contact quality is described, for example in International Patent Application No. PCT/IB2016/052686, the contents of which are included by reference herein in their entirety. In some embodiments, lesion effectiveness parameters may include the measured position 1537 of the probe, which can be measured, for example, based on electromagnetic field-guided navigation 1538, dielectrically-guided navigation 1539B, and/or imaging-based navigation 1539A.

In some embodiments, post-lesioning observations 1532 are made. Post-lesioning observations 1532 optionally include one or more of dielectric measurements 1533 which may characterize lesion state, measurements of acute electrical isolation 1534 (that is, measurements made within the time of the initial ablation procedure), measurements of persistent electrical isolation 1536 (that is, measurements made in the days, months, and/or years after the initial ablation procedure), and/or measurements made by image 1535, for example, nuclear medicine imaging of fibrotic extent. Use of dielectric measurements for characterizing lesion and/or other tissue states such as edema, is described, for example, in International Patent Application Nos. PCT/IB2016/052690 and PCT/IB2016/052686, the contents of which are incorporated by reference herein in their entirety. Optionally, a lesioning procedure is completed by making post-lesioning observations at positions near lesions and/or along the ablation line which the lesions define. In some embodiments, the post-lesioning observation positions are suggested automatically, for example, to check on tissue state at the locations between lesions most at risk for allowing electrical reconnection, and/or to check the lesions where there was is some indication of problems during the ablation procedure itself.

Turning now to tissue conditions 1520, the main relevant conditions were listed already above in relation to pre-lesioning simulations 1540, and inferred ablation results 1560. In some embodiments, at least some of the tissue conditions 1520 are provided as part of the lesion effectiveness parameters 1500. For example, a lesion partially characterized in the lesion effectiveness parameters by its depth may be transmural or not (and thus electrically isolating or not) depending on the thickness 1545 of the tissue ablated. Similarly, a lesion may more or less isolating depending on the local orientation 1525 of myocardial fibers.

In contrast, some tissue conditions shown are effectively accounted for, in some embodiments, by the parameterization of the lesion 1530. These can be optionally be left out of the lesion effectiveness parameters based on which machine learning and/or effectiveness estimation are performed. For example, temperature measured during lesioning may affect how a lesion is parameterized, but leave little residual effect affecting the estimation of lesion effectiveness.

Tissue thickness 1545 is a factor governing transmurality. Thicker tissue potentially requires deeper lesioning in order to get effective electrical isolation. Effects of tissue thickness on lesion effectiveness are discussed herein in relation, for example, to FIGS. 2B-2C. Thickness is optionally characterized based on tissue atlas information 1548, and/or based on imaging measurements 1547 obtained by analysis of anatomical images of the individual patient (obtained, e.g., by MRI, CT, nuclear medicine, or another method). Tissue thickness 1545 may be calculated and/or inferred (e.g., by machine learning methods) from dielectric measurements 1546.

Intra-lesioning temperature 1555 is optionally simulated in pre-lesioning simulations 1540, inferred from actual ablation parameters as part of inferred ablation results 1560, and/or measured 1556 during ablation. With RF ablation, for example, temperature can be an indication of ablation progress.

Similarly, edema may be simulated, inferred, or dielectrically measured 1551. Edema in cardiac tissue is potentially elicited by nearby ablations, or even by rough contact with a probe. Edematous tissue is potentially more resistant to effective ablation: for example, edematous fluid can thickens tissue so that lesion transmurality is harder to achieve.

Tissue type 1521 is optionally characterized (typically before a procedure) by one or more imaging modalities 1522. Tissue type 1521 can also be characterized intra-procedure by dielectric mapping 1523. Optionally, dielectric mapping may include creating a dielectric map of a given region of the heart, for example a map of all of or a section of a heart wall and/or heart chamber. In particular, dielectric mapping 1523 (e.g., mapping based on converting impedance measurements into dielectric properties attributable to tissue positions) potentially allows distinguishing within a mapped region between healthy, cellular tissue, and fibrotic (possibly after ablation) tissue in which cellular structure has been disrupted. In some embodiments, the dielectric measurements of tissue dielectric properties are carried out, for example, as described in International Patent Application Nos. PCT/IB2016/052690 and/or PCT/IB2016/052686, the contents of which are incorporated by reference herein in their entirety. Electrical fields of different frequencies (and preferably also established between electrode pairs in different positions) may be generated through a body tissue region of interest. Differences in impedance as a function of these field parameters may be analyzed to isolate impedance effects arising from tissue regions near the electrode. The isolated impedance effects may be analyzed for their properties in order to identify the tissue type that gives rise to them, for example, based on published tissue impedance data and/or modeling.

In some embodiments, dielectric mapping is applied to create a more general dielectric map, identifying tissue regions of any type having distinctive dielectric properties. In some embodiments, for example, the map distinguishes dielectric property differences due to tissue thickness (e.g., heart wall thickness), tissue cellular and cellular matrix makeup (including, for example, differences due to fatty deposits, collagen, muscle fiber composition, and the like), tissue cellular integrity (intact or disrupted), fluid content (e.g., edema), other tissue layers (for example, tissues lying beyond the heart wall such as lung, esophagus, and/or nervous tissue), and/or surface structure, which can potentially affect quality of contact.

In some embodiments of the invention, the level of spatial resolution of adjacent features provided by the dielectric mapping 1523 is between about 0.1 and 1 mm. Optionally, the spatial resolution is about 0.1 mm, about 0.5 mm, 1 mm, 2 mm, 5 mm, or another larger, smaller, and/or intermediate value. In some embodiments, the map is made available for display to an operator.

Finally, fiber orientation 1525 is discussed in detail herein in relation to FIGS. 5A-5B.

Reference is now made to FIGS. 5A-5B, which schematically illustrate aspects of the planned placement of lesions 301, 302, 303, 304 related to myocardial fiber direction, in accordance with some exemplary embodiments of the invention.

In some embodiments, the maximum impulse-blocking distance 305, 307 between two sub-lesions 301, 302, 303, 304 centered on points 301C, 302C, 303C, and 304C, respectively, is predicted in part by the orientation of myocardial fibers 66, 67 in the region of the gap. In general, fibers running parallel to the direction of impulse flow across the gap can transmit impulses through a smaller gap (for example, a gap of no more than about 0.3 mm, 0.4 mm, 0.5 mm, or another distance) than fibers running perpendicular to it (where the maximum size of an inhibiting gap may be, for example, about 1 mm, 1.5 mm, 2 mm, or another distance). Discussion of the influence of fiber orientation and gap size on myocardial fiber impulse transmission is found, for example, in Ranjan et al. (*Gaps in the Ablation Line as a Potential Cause of Recovery From Electrical Isolation and Their Visualization Using MRI*. Circ Arrythm Electrophysiol 2011; 4:279-286). In the computational modeling of Ranjan et al., the reported maximum gap at which conductivity failed was 1.4 mm when fiber direction was perpendicular to the ablation line. When fiber direction was parallel to the ablation line, conductivity failure was reported only up to 0.3 mm gaps. Ranjan et al. suggest that larger gaps which appear to at least initially block conduction in in vivo studies may include tissue with temporarily reduced conductivity which could later recover and resume conduction.

In some embodiments of the invention, myocardial fiber orientation is modeled from anatomical atlas data giving typical orientations, and/or measured for the individual patient using, for example, echocardiography-based shear wave imaging (Lee et al., *Mapping myocardial fiber orientation using echocardiography-based shear wave imaging*. IEEE Trans Med Imaging 2012; 31(3):554-62), Diffusion tensor magnetic resonance imaging (Pashakhanlo et al., *Myofiber Architecture of the Human Atria as Revealed by Submillimeter Diffusion Tensor Imaging*. Circ Arrhythm Electrophysiol. 2016; 9:e004133), or another method.

Reference is now made to FIG. 3D, which is a schematic illustration highlighting details of a planned set of ablations creating sub-ablations 220, and their traversal along a line of planned ablation 55, in accordance with some exemplary embodiments of the invention.

Potentially, positioning for lesioning achieved by direct movement between adjacent lesion foci (sub-lesions, for example) is less prone to errors and/or delays which can introduce gaps in the ablation line that permit impulse transmission. However, joining between the starting and stopping points of an ablation line generally requires making a join between sub-lesions, where the later sub-lesion is formed up to several minutes after the earlier one. During the interval, not only does the tissue tend to cool (which can reduce a degree of sub-lesion chaining), but there can also be an edematous response by the tissue which affects ablation effectiveness. In some embodiments, these effects are simulated and/or estimated as part of ablation planning.

In some embodiments, an ablation plan is designed so that such joins are positioned over regions where myocardial fiber orientation 68 (just a few patches of fiber orientation 68 are shown for illustration) generally cuts across to the direction of potential propagation across the gap. For example, sub-lesion 310 is optionally a preferred candidate for a starting lesioning position, since the local direction of fibers means that sub-lesion neighbor 319 can be placed with greater error, while still maintaining an effective block.

The effectiveness of an ablation lesion for creating electrical isolation is potentially affected by the direction of myocardial fibers running nearby: for example, fibers oriented to run through a gap (for example, as in FIG. 5B) apparently transmit impulses more efficiently than fibers oriented so that impulses must jump laterally from fiber to fiber to pass the gap (for example, as in FIG. 5A). Optionally, fiber orientation used in simulating or inferring ablation effects is derived from atlas-based assumptions 1527 about heart wall anatomy. Additionally or alternatively, fiber orientation is imaged 1526, for example, using echocardiography-based shear wave imaging, and/or diffusion tensor imaging. In some embodiments, fiber orientation between two points is inferred from the rate of impulse transmission therebetween, e.g., from impulse timing measurements 1528.

In some embodiments of the invention, patient data parameter are also provided as part of lesion effectiveness parameters 1500. Optionally, the patient data parameter include patient medical history and/or patient vital statistics, for example, one or more of:

- Patient demographics (gender, age, height, weight, body mass index [BMI]);
- Occupation;
- CHAD2 Score for atrial fibrillation (AF) stroke risk (e.g. scored as: congestive heart failure history +1, hypertension history +1, age ≥75 years +1, diabetes mellitus history +1, stroke or transient ischemic attack [TIA] symptoms previously +2);
- CHAD2VASc Score (e.g., scored as: age in years: <65 0, 65-74+1, ≥75+2, sex: male 0, female +1, congestive heart failure history +1, hypertension history +1, stroke/TIA/thromboembolism history +2, vascular disease history +1, diabetes mellitus +1);
- Family history of AF;
- Known genetic predisposition to AF (for example mutations in the KCNE2, KCNJ2, and/or KCNQ1 genes);
- AF subtype characteristics (e.g., symptoms, age of first documented episode, time since first discovered, number and duration of episodes, need of cardioversion, hospitalization);
- AF definition (e.g., paroxysmal, persistent, chronic persistent, permanent);
- Other coexisting arrhythmia (e.g., atrial flutter, accessory pathway, atrial tachycardia);
- Drug therapy (e.g., antiarrhythmic rate or rhythm control, antithrombotic, anticoagulation);
- Compliance with drug therapy;
- Known hypercoagulability;
- Other heart disease (e.g., structural, previous surgery, previous cardiac catheterization, ischemic, cardiomyopathy);
- Life style and habits;
- Smoking;
- Drug abuse;
- Alcohol consumption;
- Other comorbidities (e.g., endocrine dysfunction, malignancy);
- Other drug therapy;
- Autonomic nervous system state (e.g., hyperactive, normal, hypoactive);
- Left atrial characteristics (e.g., diameters, volume, function, left atrial artery [LAA] shape type, presence of clot, presence of patchy fibrosis, scars, etc.);
- Mitral valve function (e.g., degree of regurgitation if present, degree of floppiness if mitral valve prolapse is present);
- Function of other cardiac valves;
- Presence of prominent Eustachian valve;
- presence and type of patent foramen *ovale* (e.g., documented right to left or left to right inter-atrial shunt, presence of marked inter-atrial septal aneurysmatic motion);
- Atherosclerosis (e.g., state of carotid arteries, state of the circle of Willis, state of coronary arteries, state of renal arteries);
- Peripheral artery disease;
- History of deep vein thrombosis or pulmonary emboli (long seated position syndrome);
- Characteristics of self-healing process (e.g., levels of angiogenesis growth factors, scar formation)
- Level of myocardial injury biomarkers following the cardiac ablation procedure (e.g., creatinine kinase [CK], myocardial bound for CK [CK-MB], Troponin-I [TnI]);
- Heart rhythm during the ablation procedure (normal sinus rhythm [NSR], atrial fibrillation, or atrial flutter) and/or need for cardioversion during the procedure;
- Recurrence of AF post-ablation (e.g., timing, symptoms, duration of episodes, need for cardioversion, drug therapy);
- Remodeling of left atrium post-cardiac ablation (documented on CT/MR imaging);
- Left atrium stunning post ablation (documented on electrocardiography, e.g. TTE or TEE);
- Number and duration of hospitalizations post ablation
- Stroke or documented brain MR lesions post ablation; and/or
- Quality of life post-ablation (subjective questionnaire).

Optionally, data indicating therapeutic strategy and/or events are included in the lesion effectiveness parameters 1500, for example:

- Pulmonary vein isolation (PVI) only
- PVI together with an additional roof or mitral ablation line;
- PVI+focal ablations, e.g. due to complex fractionated atrial electrograms, dominant frequency and/or rotors;
- Neuromodulation (ganglionated plexi ablation);
- Number of ablation points;
- Procedure time; and/or Immediate complication (e.g. cardiac perforation, tamponade, esophageal lesions, phrenic nerve palsy).

Context-Adjusted Lesion Effectiveness Estimator

Figure 4B:
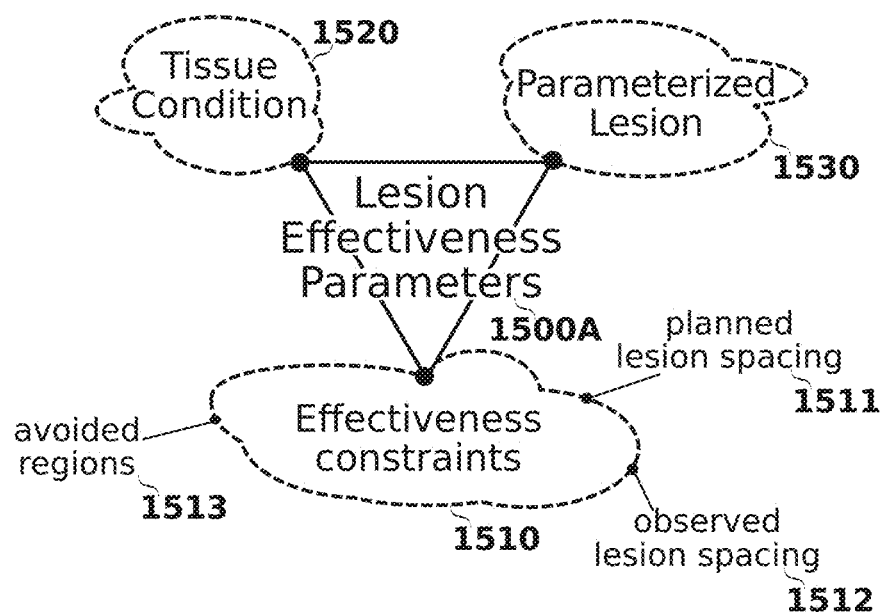
FIG. 4B schematically represents a range of options for prior inputs to a lesion effectiveness estimator and for machine learning of the estimator, comprising parameters potentially relating to lesion effectiveness, including prior inputs defining conditions for lesion effectiveness, according to some embodiments of the present disclosure.

Reference is now made to FIG. 4B, which schematically represents a range of options for prior inputs to a lesion effectiveness estimator and for machine learning of the estimator, comprising parameters potentially relating to lesion effectiveness, including prior inputs defining conditions for lesion effectiveness, according to some embodiments of the present disclosure.

For simplicity, FIG. 4B is abbreviated from FIG. 4A to show just the two main divisions of tissue condition 1520 and parameterized lesion 1530; however, any of the parameter descriptions mentioned in relation to FIG. 4A should also be considered as included within this FIG. 4B. The substantial difference from FIG. 4A is that the lesion effectiveness parameters 1500A may be supplemented by an optional requirements node: effectiveness constraints 1510. Optionally, lesion effectiveness parameters 1500A also includes any parameters described with respect to patient data parameter and/or ablation strategy in regards to lesion effectiveness parameters 1500.

Effectiveness constraints 1510 are optionally derived, for example, from planned lesion spacing 1511 and/or observed (for example, dielectrically measured) lesion spacing 1512. Planned lesion spacing 1511 and/or observed lesion spacing 1512 may be expressed in terms of distances (for example, when lesion shape is geometrically defined as a basis for machine learning), but can also be otherwise defined, e.g., as a constraint on the minimum strength of a dielectric signal indicating fibrotic tissue under the electrode.

Optionally, effectiveness constraints include regions where lesioning should be avoided (avoided regions 1513). These places optionally include, for example, lesions located too near to the esophagus, too near the phrenic nerve, and/or too near the venous roots. Effectiveness constraints such as avoided region 1513 optionally provide a potential advantage, e.g. for indicating whether or not an ablation plan is safe, and/or for indicating a potential for complications, in case the ablation procedure has already been performed. Additionally or alternatively, other safety constraints are used; for example, constraints on maximum power settings, maximum duration of ablation, etc., which, if exceeded, could indicate an increased potential for complications during and/or after a procedure.

A potential effect of adding effectiveness constraints to the lesion effectiveness parameters 1500A is to allow the machine learning process to incorporate some information about local tissue context into the effectiveness estimator. A lesion's effect on electrical isolation potentially depends not only on being transmural, but also on being joined up to adjacent lesion positions. Effectively, this requirement may allow the machine learning process to distinguish between lesions of the same diameter, where the effective lesion meets the required size for its position (that is, contacts its neighbors), but the ineffective lesion does not contact its neighbors, and so fails to provide effective electrical isolation.

This local-context approach, which may be applied to every sub-lesion in an ablation line potentially provides a way to judge the overall effectiveness of electrical isolation of the ablation line, emergent from estimation of the effectiveness of each sub-lesion. Alternatively, estimation overall ablation line effectiveness may be treated as a separate problem, either independently calculated, or calculated in cascade with estimations of individual sub-lesion effectiveness.

Estimators for Ablation Line Effectiveness

Figure 6:
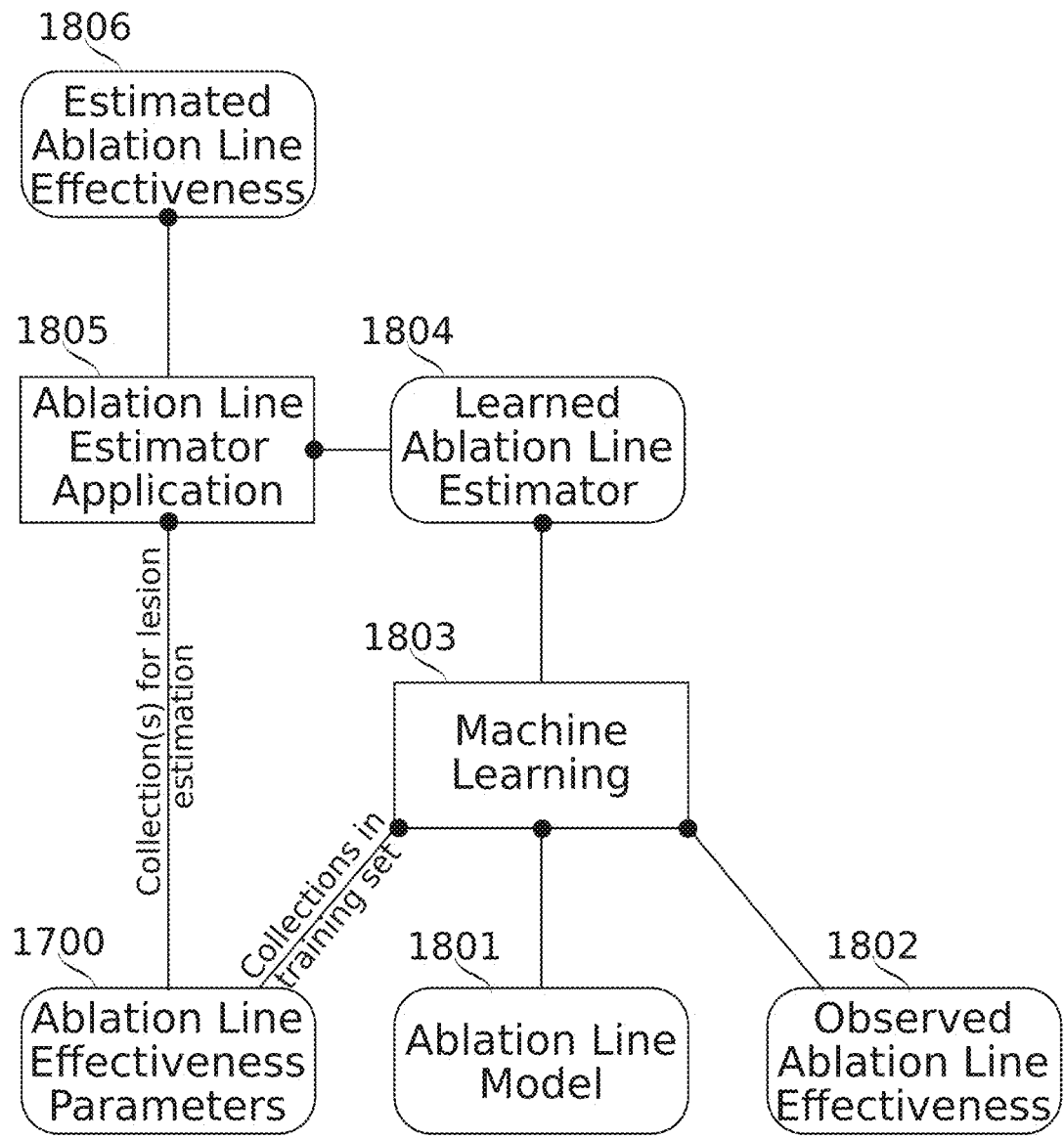
FIG. 6 is a schematic flowchart of a method of deriving and applying an estimator for predicting ablation line effectiveness, according to some embodiments of the present disclosure.

Reference is now made to FIG. 6, which is a schematic flowchart of a method of deriving and applying an estimator for predicting ablation line effectiveness, according to some embodiments of the present disclosure.

Conceptually, the blocks of FIG. 6 correspond to the blocks of FIG. 1B with the substitution of ablation line effectiveness (that is, the effectiveness of a linked group of lesions, e.g., at creating electrical isolation) for individual lesion effectiveness. Ablation line effectiveness parameters 1700 are provided, e.g., as described in relation to FIGS. 10A-10B. Machine learning at block 1803 may be applied to collections of ablation line effectiveness parameters 1700 assigned to a training set, each with a corresponding observed ablation line effectiveness 1802, and optionally based on an ablation line model 1801. Machine learning at block 1803 may be in accordance with techniques described in relation to machine learning 1603. Ablation line effectiveness parameters 1700 may include one or more parameters described in relation to lesion effectiveness parameters 1500 or 1500A, for example as described in relation to FIGS. 4A and 4B. Ablation line effectiveness parameters 1700 may include dielectric measurements. Ablation line effectiveness parameters 1700 may include indications of conditions of formation of an ablation line and/or sub-lesions of the ablation line; for example, lesion placement, ablation tool settings governing sub-lesion formation (such as ablation power, dielectric quality of contact, angle of contact, force of contact, and timing of ablation), and/or tissue conditions within which the sub-lesion is situated. Ablation line effectiveness parameters 1700 may include indications of structure of an ablation line (e.g., depth, size, volume of tissue etc.).

The resulting learned ablation line estimator 1804 is the applied at block 1805 to other collections of ablation line effectiveness parameters 1700, producing estimates of ablation line effectiveness 1806. Other collections of ablation line effectiveness parameters 1700 may refer to ablation line effectiveness parameters 1700 collected after learned ablation line estimator 1804 was created, e.g., ablation line effectiveness parameters 1700 collected in run-time during a medical procedure. Other collections of ablation line effectiveness parameters 1700 may include dielectric measurements measured run-time during a medical procedure. Such dielectric measurements may be used as inputs to learned ablation line estimator 1804 to obtain estimated ablation line effectiveness 1806.

It should be noted that learned ablation line estimator 1804 may be updated and/or adjusted based on such other collections of ablation line effectiveness parameters 1700.

In some embodiments, the estimator output (e.g., estimated ablation line effectiveness) may include a binary prediction (e.g., +1 or −1). In some embodiments, the estimator output (e.g., estimated ablation line effectiveness) may include a probabilistic output, e.g., between zero and one (e.g., a dynamic score). Such embodiments may be advantageous when using estimator during an ablation procedure. For example, they may facilitate a user decision whether to proceed or complete the procedure and/or to adjust the ablation plan.

Estimated ablation line effectiveness 1806 may be presented to a user (e.g., physician) during a medical procedure. Such estimated lesion effectiveness 1806 may be used to adjust an ablation plan.

In the context of ablation lines, effectiveness also applies relative to criteria of electrical isolation, lesion persistence, and/or freedom from disease at various time points, as also described in relation to FIG. 1B. Optionally, estimates of ablation line effectiveness 1806 are accompanied by a metric of certainty, for example, sensitivity and/or selectivity. Estimated ablation line effectiveness 1806 optionally is configured to identify the most likely location or locations along the ablation line where incomplete electrical isolation occurs or will occur. In some embodiments, estimated ablation line effectiveness 1806 is displayed within an interactive user interface allowing an operator to examine the estimate of ablation line effectiveness from different perspectives: for example, to check certainty of results, to check estimated lesion effectiveness 1606 which may correspond to estimated position of failed electrical isolation along the ablation line, to compare the current ablation line with other ablation lines in the database which historically have produced similar estimator results, etc.

The primary difference from FIG. 1B is that the estimator now is able to take into account the whole context of a line of lesions, rather than each lesion individually, or lesions individually within a local context. For example, there may be a lesion which lesion-only estimation scores as ineffective (even taking into account local context), perhaps because one lesion is not transmural, leaving a possible transmission gap. However, if the placement of other lesions (optionally including consideration of pre-existing scar tissue) is such that no effective electrical impulse can reach the allowed gap, then an ablation line estimator is potentially be able to detect that the overall ablation line remains effective.

Also, in some embodiments, an estimator built around features of the ablation line as a whole is potentially more convenient for the analysis of gaps between lesions. For example, since gaps can optionally be described directly in the ablation line effectiveness parameters, and their behavior even modeled, rather than be relegated to being the implicit consequence of inadequate ablation size or placement.

Figure 7A:
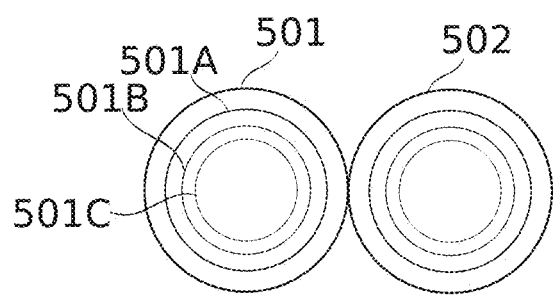
FIGS. 7A-7B schematically illustrate adjacency effects of tissue lesions made in two different sequences, in accordance with some exemplary embodiments of the present disclosure.
Figure 7B:
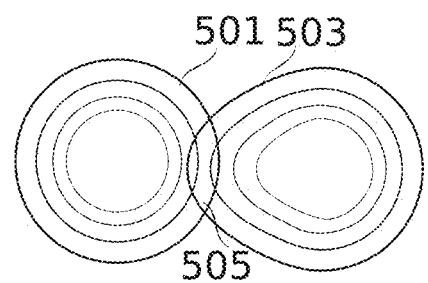

Reference is now made to FIGS. 7A-7B, which schematically illustrate adjacency effects of tissue lesions 501, 502, 503 made in two different sequences, in accordance with some exemplary embodiments of the invention.

A superficial extent of sub-lesion 501 is represented by the outer circle, while progressively smaller interior circles 501A, 501B, 501C represent lesion extent at gradually increasing depths (depth is similarly represented for sub-lesions 502 and 503). In some embodiments, after a first lesion 501 is made, a second lesion 502 is made only after the elapse of a cool-down period. Then the two lesions potentially are made as if independent from one another. Unless care is taken to ensure sufficient overlap, this can increase the potential for an impulse-permissive gap, particularly in the deeper layers.

In FIG. 7B, however, sub-lesion 503 is placed almost immediately after creation of lesion 501, while there remains some residual heating from the previous ablation. In this case, thermal simulation may show that the two sub-lesions will tend to merge, for example as shown at region 505.

The ablation effect (e.g., the lesion effectiveness) of a first sub-lesion may be estimated, for example as described in reference to FIG. 1A, e.g., using estimator 1604. For example, lesion effectiveness parameters and/or lesioning effects on tissue parameters may be inputs to an effectiveness estimator (e.g., estimator 1604) before second sub-lesion ablation occurs. Optionally, such estimating facilitates defining the sub-lesioning sequence; e.g., the order and/or timing by which sub-lesions are ablated.

Chained Lesion and Ablation Line Effectiveness Estimators

Figure 9:
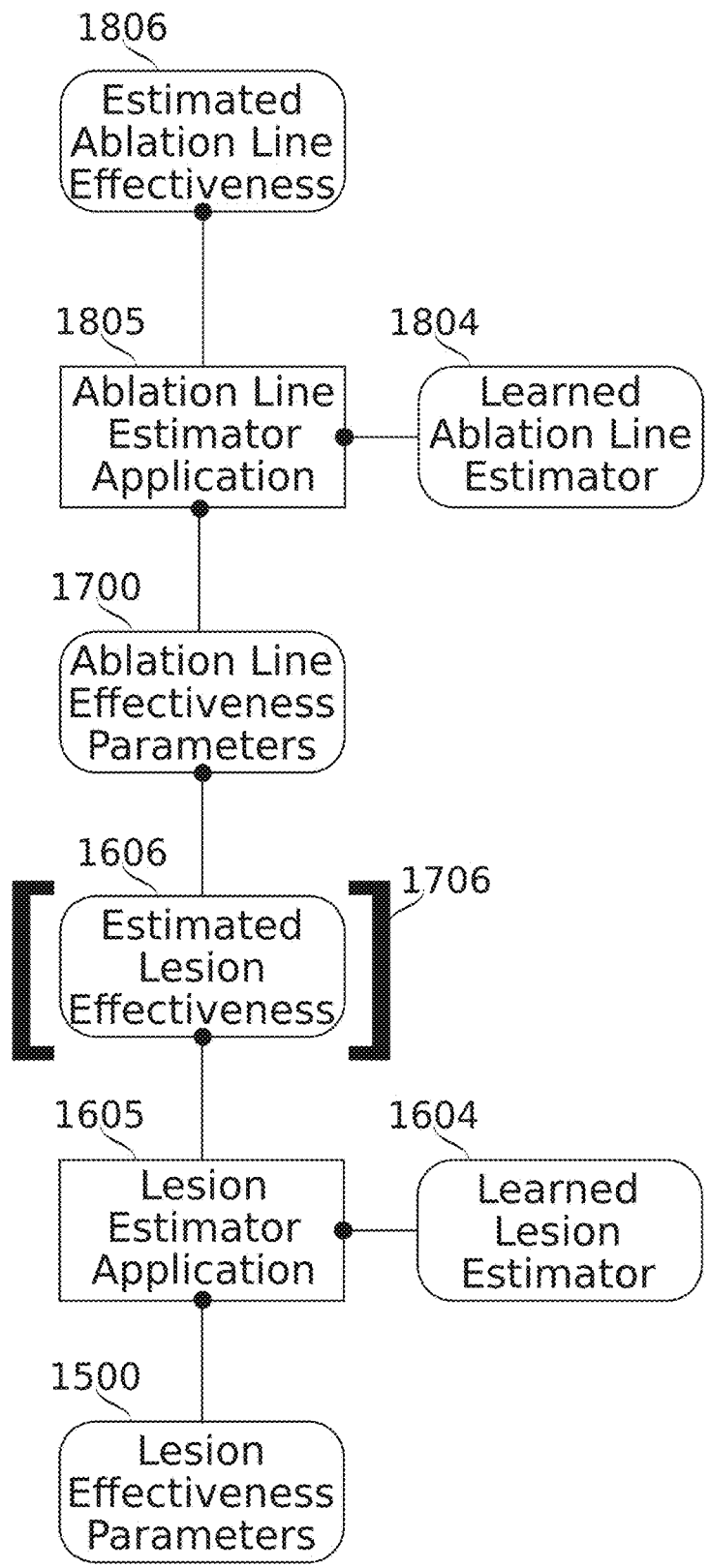
FIG. 9 is a schematic flowchart of a method of chaining estimators predicting lesion effectiveness and ablation line effectiveness into a sequence, according to some embodiments of the present disclosure.

Reference is now made to FIG. 9, which is a schematic flowchart of a method of chaining estimators predicting lesion effectiveness and ablation line effectiveness into a sequence, according to some embodiments of the present disclosure.

FIG. 9 comprises a chaining together of the estimation pathway portions of FIGS. 1B and 6, and the meaning of the blocks shared with them is the same. The difference is in the chaining. An estimated lesion effectiveness 1606 for each lesion in an ablation line may be collected in an estimation array 1706 of lesion effectiveness estimates. Then array 1706 may be provided in turn as part of the ablation line effectiveness parameters 1700, so that the estimation array 1706 becomes part of the input data, based on which the estimator function operates. It should be understood that in such an example, learned ablation line estimator 1804 was previously learned using training set data including examples of estimation array 1706.

In some embodiments, an effect of adding a second stage of estimator processing (ablation line effectiveness estimator chained onto results of a lesion effectiveness estimator) is to correct potential limitations of lesion-based estimations of effectiveness. For example, two apparently effective lesions (according to a lesion effectiveness estimator) may actually be too separated from one another to create electrical isolation. Conversely, as mentioned in relation to FIG. 6, an apparently ineffective lesion is potentially located where the gap that it allows is inaccessible to electrical impulses of the heart—and so the gap is functionally harmless, and the ablation line is potentially effective after all.

Figure 10A:
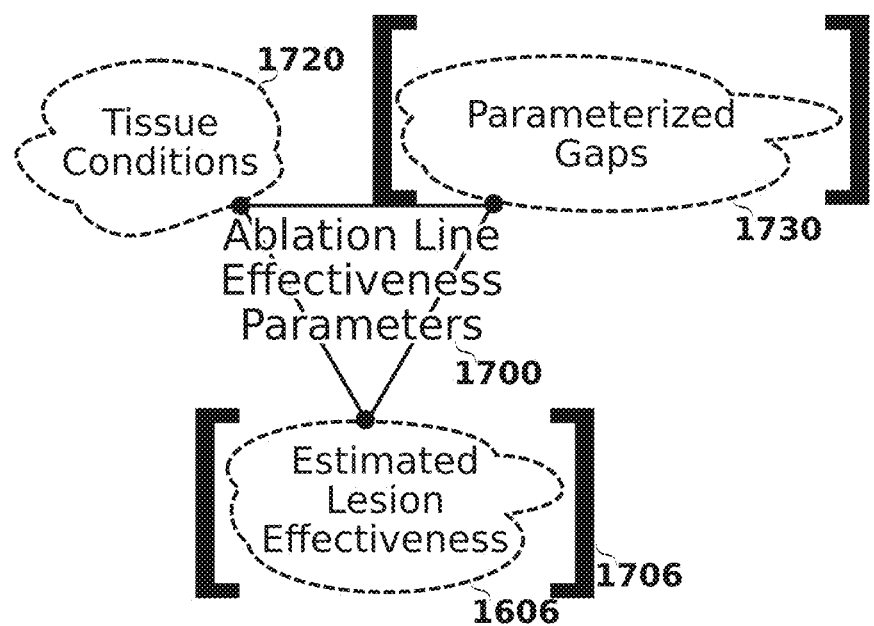
FIG. 10A schematically represents options for prior inputs to an ablation line effectiveness estimator and for machine learning of the estimator, comprising parameters potentially relating to ablation line effectiveness, including inputs comprising output of a lesion effectiveness estimator, according to some embodiments of the present disclosure.

Reference is now made to FIG. 10A, which schematically represents options for prior inputs to an ablation line effectiveness estimator 1804 and for machine learning of estimator 1804, comprising parameters potentially relating to ablation line effectiveness, including inputs comprising output of lesion effectiveness estimator 1604, according to some embodiments of the present disclosure. Output of lesion effectiveness estimator 1604 may include estimated lesion effectiveness 1606 and/or estimation array 1706.

Ablation line effectiveness parameters 1700 of FIG. 10A comprise parameters which are optionally supplied to the methods of FIGS. 6 and 9 as a basis for machine learning of an ablation line effectiveness estimator 1804, and/or for use of estimator 1804. Optionally, ablation line effectiveness parameters 1700 also includes any parameters described with respect to patient data parameters and/or ablation strategy in regards to lesion effectiveness parameters 1500. In some embodiments, ablation line effectiveness parameters 1700 may include dielectric measurements.

Ablation line effectiveness parameters 1700 of FIG. 10A may comprise Tissue conditions 1720 and/or parameterized gaps 1730.

Tissue conditions 1720 optionally comprise any suitable combination of the tissue condition parameters discussed in relation to FIG. 4A, or another parameter indicating tissue condition. Similarly to as in FIG. 4A, the parameters indicating tissue conditions 1720 are optionally considered as supplying information which can be weighted in the learned estimator to modulate the estimated effectiveness of the ablation line itself.

Compared to parameters used as lesion effectiveness parameters 1500, ablation line effectiveness parameters 1700 optionally include more information relating to global tissue structure. For example, data about fiber orientation 1525 is optionally incorporated not just for tissue immediately surrounding lesions, but also for regions that electrical impulses cross to reach the lesions. Similarly, measurements of impulse propagation over these regions are optionally incorporated into the ablation line effectiveness parameters. This potentially allows more refined prediction of the functional implication of gaps, derived, for example, from information about the strength of impulses that reach those gaps.

In some embodiments, parameterized gaps 1730 optionally includes any suitable combination of the parameters already discussed in relation to the parameterized lesions 1530 of FIG. 4A. However, the measurements are optionally parameterized in terms of characterizing gaps (or potential gaps) between lesions, rather than the lesions themselves (for which estimator results are already available).

Additionally or alternatively, data used to form parameterized gaps 1730 comprises dielectric characterization of regions into which lesions do not extend, and/or extend with incomplete electrical isolation. Optionally, gap parameter information comprises observations (e.g., measured from catheter electrodes) of places where electrical isolation is not achieved. Optionally, measurements delineate the extent of electrical isolation between lesions. Potentially, an early extent of impulse activity, even if it is presently electrically isolated, is indicative (e.g., because of how far it intrudes into a region of the ablation line) of possible later loss of electrical isolation as tissue recovers from a procedure. It should be understood that a parameter relating to a gap is optionally reconfigured as a parameter relating to a lesion (for example, by adding constraint parameters on lesion size, as described in relation to FIG. 4B, herein). In either case, the availability of input data giving at least relative lesion placements is important for the estimation of overall integrity of the electrical isolation created by the lesion line. This may be derived, for example, from the absolute shape of the ablation line, from the size of regions of mutual overlap for each lesion, from relative distances for each lesion from its neighbors combined with measured and/or inferred diameter, etc.

Finally, estimation array 1706 may be used, in some embodiments, to provide information relating to the effectiveness of electrical isolation, and/or the predicted persistence, of the lesions themselves.

Stand-Alone Ablation Line Effectiveness Estimator

Figure 10B:
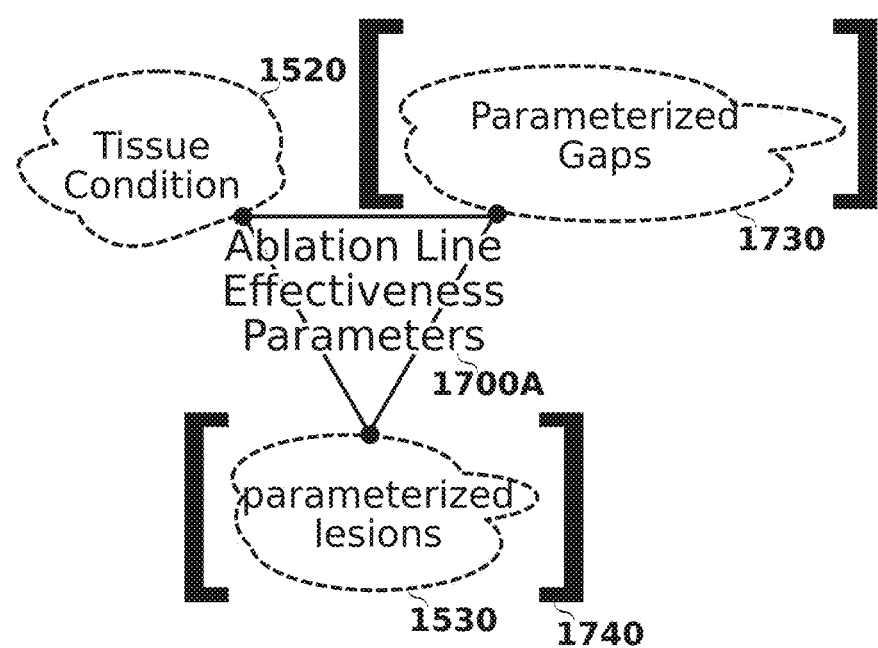
FIG. 10B schematically represents options for prior inputs to an ablation line effectiveness estimator and for machine learning of the estimator, comprising parameters potentially relating to ablation line effectiveness for use with a stand-alone ablation line effectiveness estimator according to some embodiments of the present disclosure.

Reference is now made to FIG. 10B, which schematically represents options for prior inputs to an ablation line effectiveness estimator and for machine learning of the estimator, comprising parameters potentially relating to ablation line effectiveness for use with a stand-alone ablation line effectiveness estimator according to some embodiments of the present disclosure.

FIG. 10B indicates an alternative implementation of ablation line effectiveness parameters 1700A, used, for example, in some embodiments of the present invention wherein the method of FIG. 6 for generating and using learned ablation line estimator 1804 is used standalone, without chaining to the results providing an estimated lesion effectiveness 1606. Optionally, ablation line effectiveness parameters 1700A also include any parameters described with respect to patient data parameters and/or ablation strategy in regards to lesion effectiveness parameters 1500.

Rather than including estimation array 1706, ablation line effectiveness parameters 1700A optionally directly include lesion parameterization array 1740 parameterising a plurality of lesions making up the ablation line. Lesion parameterization array 1740 may include an array of parametrized lesions 1530.

It should be understood that the parameter configurations of FIGS. 10A and 10B represent two ends of a spectrum. In some embodiments, both lesion parameterization array 1740 and array 1706 of estimated lesion effectiveness are used in combination. Moreover, the role of parameterized gaps 1730 in FIGS. 10A-10B is optionally replaced by extended parameterizations of the lesions, e.g., as allowing or not allowing space between each other.

Estimator Uses

Figure 11:
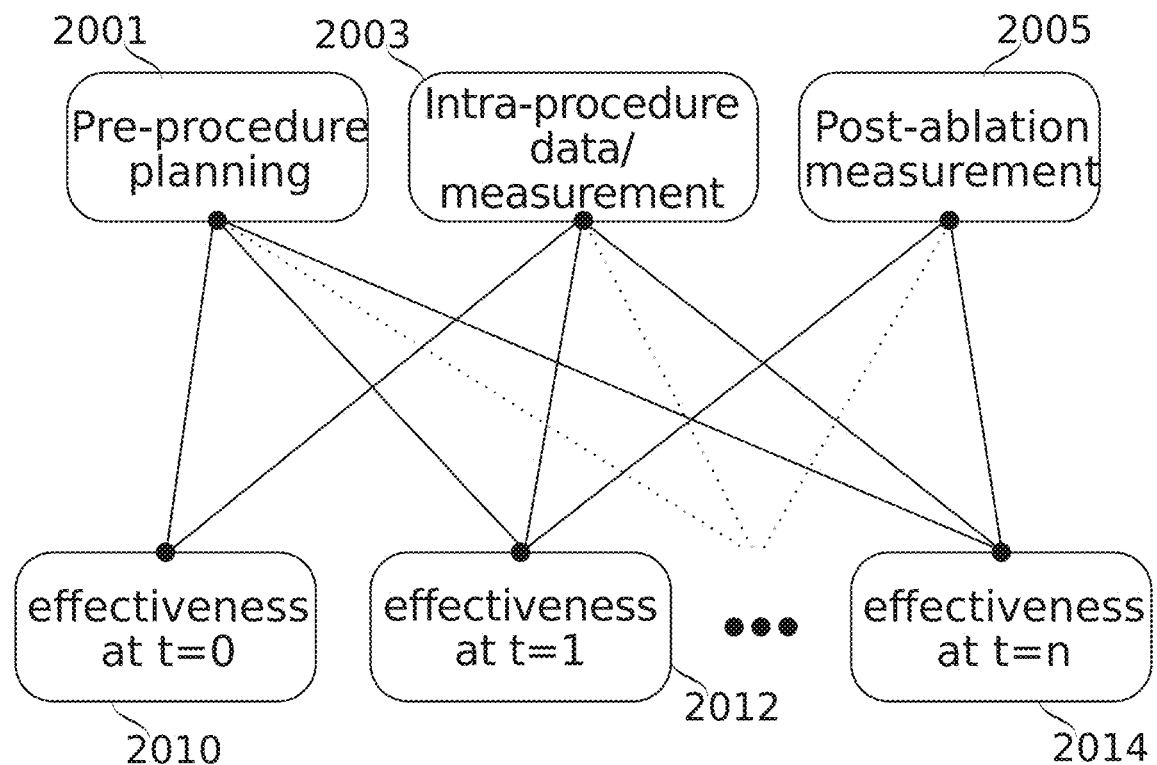
FIG. 11 schematically represents different periods for acquiring prior inputs to estimators, and their relationship to different periods for acquiring feedback inputs to estimators, according to some embodiments of the present disclosure.

Reference is now made to FIG. 11, which schematically represents different periods for acquiring prior inputs to estimators, and their relationship to different periods for acquiring feedback inputs to estimators, according to some embodiments of the present disclosure.

FIG. 11 illustrates an organizing principle mentioned in the discussion of FIG. 4A: that data sources for parameters may be assigned to one or more of the three time stages. The three stages are shown here as pre-procedure planning 2001, intra-procedure data and/or measurement 2003, and post-procedure measurement 2005.

Shown in the bottom row of FIG. 11 are three exemplary effectiveness estimations, each for a different point in time: at the time of the ablation procedure (t=0, block 2010), and for a plurality of times after the ablation procedure (t=1 . . . t=n; blocks 2012 and 2014). Estimators 2010, 2012 and 2014 may include any of the estimators described above; for example: lesion estimator 1603 and/or ablation line estimator 1804 and/or ablation segment estimator 2104 and/or edema estimator 2604.

Ideally, the only estimator needed would be the final one for t=n (for example, estimation of effectiveness at five years post-procedure), since permanent treatment of disease is the end goal. Practically, however, each estimator may find a use in different stages of pre-procedure planning, adjustment of ablation strategy during the procedure, and/or post-procedure follow-up. A plurality of estimators may be created to target different information—for example, to target a single outcome aspect (e.g., transmission blockage as such), or any suitable combination of outcome aspects (e.g., transmurality, inter sub-lesion connection, success at ablating before edema sets in, etc.). There is a potential advantage of single-aspect estimators in simplicity of implementation. There is also a potential advantage for interpretation, since knowing what specific portion of a procedure is problematic helps to target planning of mitigation and/or remediation. The three general stages are now discussed in turn.

Estimator use in pre-procedure planning: At the pre-procedure planning stage 2001, short-term estimations of the effectiveness of an ablation plan in achieving electrical isolation are potentially the most useful. In particular, there may be more detailed feedback information available for short-term estimator; particularly for estimators based on outcomes measured during the ablation procedure, and/or outcomes measured during a period of more active treatment and follow-up soon after a procedure.

However, it is potentially helpful to be informed that there is at least a possibility of long-term effectiveness for a particular plan, even though there remain a large number of unresolved variables (e.g., in carrying out the procedure itself) that could make estimation of likely future effectiveness difficult. Potentially, moreover, there are hidden long-term consequences of a plan—for example, lesions placed in a heart region which is, perhaps unknowingly, difficult to characterize. Long-term feedback data can potentially indicate that there is some problem related to such lesions. Such hidden problems may potentially result a lowered estimate of effectiveness, even if the physiological reason for the lowered estimate remains unknown.

Estimator use during a procedure: During the procedure itself (block 2003), estimator results are optionally updated regularly as new ablations are performed. Re-estimation is performed, for example, after or before every ablation of a sub-lesion and/or completion of an ablation segment, or after any suitable number of ablations sufficient to get useful data, for example, after at least 10-30 ablations. Estimations are optionally refreshed every time new data becomes available, or optionally every few seconds or minutes (e.g. 5 seconds, 10 seconds, 30 seconds, 1 minute, 2 minutes, 5 minutes or another longer, shorter or intermediate period). Since the estimation is by then largely based on effectiveness estimated from actual measurements and events, long-term estimates may begin to be more accurate. However, short-term estimators developed from detailed feedback data may again provide more useful feedback for evaluating potential adjustments to a procedure—e.g., which particular lesions are insufficient and should be revisited, or which parts of the ablation line are vulnerable to developing gaps.

Estimator-driven adjustments (e.g., adjustment of an ablation plan) are optionally manually guided (e.g., a computer shows an estimator result to an operator, who decides how to proceed), or automatic. The following is an example of an automatic adjustment:

Upon an operator selecting the position of the next ablation operation (such as: next lesion position), the ablation monitoring and/or treatment system optionally applies an estimator to predict effectiveness of the result using not only the current settings, but also other settings available from within current conditions—for example, different power levels, times of ablation, frequencies, phases, angles of approach and the like. This can be considered as a way of searching an envelope of possible ablation parameter settings in order to select the parameter settings which seem most likely to lead to a targeted effectiveness outcome. Optionally, the estimation is provided for effectiveness in a single respect (e.g., transmurality). Alternatively, estimation considers effectiveness in a plurality of respects such as safety, transmurality, gap-free connection with adjacent lesions, permanence of the lesion, gap-free connection between adjacent sub-lesions of an ablation segment, permanence of the ablation segment, etc.). Optionally, the different respects are at least partially in competition to each other (a large lesion may be less safe, for example).

An estimator feature potentially of particular use during ablation is estimation of the effects of edema on ablation. An initial ablation plan may attempt to account for edema by simply lesioning in a line, so that most ablations happen too quickly for edema from neighboring ablations to be a factor. However, adjusting an ablation plan to mitigate a possible gap in isolation may involve returning to a point where ablation has had time to become well-developed. In some embodiments, estimation of edema state can be used to find an optimal location for a repair ablation, and/or to reconfigure ablation parameters so that effective ablation is more likely.

Estimator use after a procedure: Once the post-procedure clinical situation has stabilized, the long-term estimators potentially become of more practical use, as key medical decisions also become more strategic in nature. An estimator looking months or years in advance at the likelihood of disease recurrence can help a clinician advise a patient when the next follow-up session should occur, and/or help to plan for an apparently likely eventuality of the return of disease. In some embodiments, an ablation segment effectiveness estimator estimates a likelihood (for example, a percentage likelihood, or another prediction, optionally including an estimate of specificity and/or sensitivity) of effective block for one or more ablation segments within a week, a month, three months, six months, a year, two years, five years, or any other suitable period after the procedure that created the ablation segment.

Estimators for Ablation Segment Effectiveness

For purposes of describing ablation segment effectiveness estimators herein, an ablation segment comprises any planned or actual segment of a longer ablation line selected for evaluation by an estimator. An ablation line, in some embodiments, comprises a group of one or more sub-lesions introduced together by ablation to achieve a clinical result. Typically a plurality of sub-lesions are selected. Two or more adjacent and/or overlapping sub-lesions along an ablation line may be referred as ablation segment.

Typically, the sub-lesions are introduced as a chain of ablations extending along a pathway, with the target of creating an uninterrupted barrier to electrical transmission from one side of the line to the other. In some embodiments, an ablation segment comprises at least two sub-lesions in proximity. "Effectiveness" of such a segment, in some embodiments, is defined as next described.

In some embodiments of the invention, an ablation segment effectiveness estimator is used to predict acute (e.g., immediate) and/or persistent (e.g., over a period of at least 1 month, 3 months, 6 months, 1 year, 2 years, 5 years, or another longer, shorter, or intermediate period) effectiveness of an ablation segment; optionally either a planned or actual ablation segment. Effectiveness of a segment, in some embodiments, relates to properties of the segment's sub-lesions, regions which may exist between those sub-lesions, and/or the extent of sub-lesions relative to the overall thickness of the ablation tissue (effective transmurality). Effectiveness of an ablation segment, in some embodiments, comprises completeness of electrical isolation across, under, or over the segment.

It should be noted that it is difficult to directly validate ablation success in humans, since direct visual inspection of sub-lesions in a living patient (e.g., for transmurality, interconnectedness, etc.) is unavailable. Accordingly, it is a potential advantage to make use of a wide variety of indirect and/or incomplete data sources which at least partially indicate (e.g. correlate with) procedure success, in order to supply a greater level of certainty for planning of procedures, correction of ongoing procedures, and/or prediction of procedure outcomes.

Figure 14A:
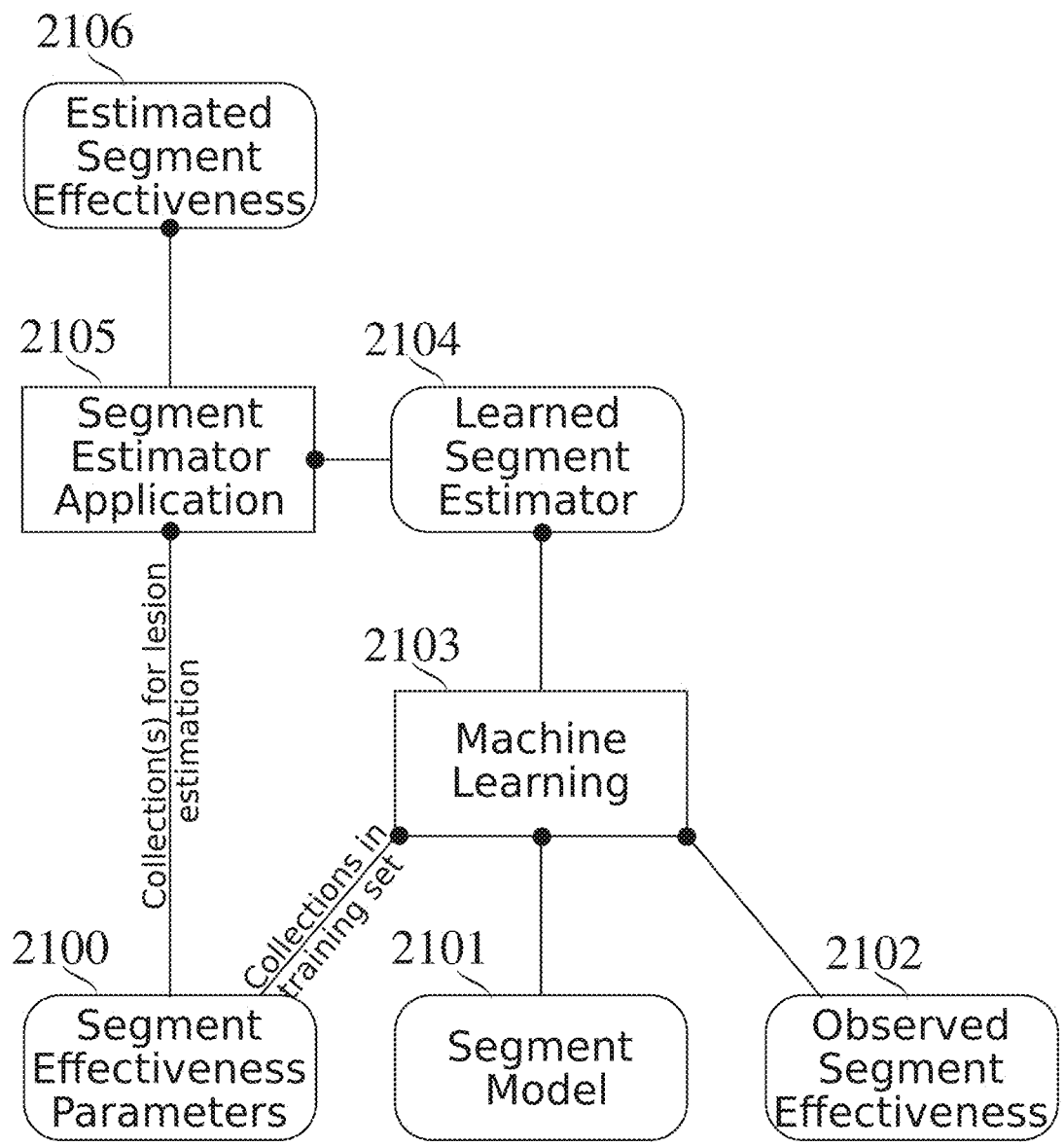
FIG. 14A is a schematic flowchart of a method of deriving and applying an estimator for predicting ablation segment effectiveness, according to some embodiments of the present disclosure.

Reference is now made to FIG. 14A, which is a schematic flowchart of a method of deriving and applying an ablation segment effectiveness estimator for predicting ablation segment effectiveness, according to some embodiments of the present disclosure. First, inputs to and operation of machine learning at block 2103 are described. Then application of a learned ablation segment effectiveness estimator 2104 at block 2105 is described (in FIG. 14A and other figures herein, both "segment estimator" and "ablation segment effectiveness estimator" are also used to refer to an ablation segment effectiveness estimator).

Prior Inputs to Machine Learning

In some embodiments, the block marked 2100 in FIG. 14A comprises a plurality of "collections" of ablation segment effectiveness parameters 2100. Each such collection in turn comprises a heterogeneous set of data inputs relating to one or more particular ablation segments. The particular ablation segment is formed (and/or is planned to be formed) by the operation of an ablation modality (e.g., radio frequency ablation, cryoablation, microwave ablation, laser ablation, irreversible electroporation, substance injection ablation, and high-intensity focused ultrasound ablation) acting on tissue which is targeted for ablation. The data inputs of a collection of ablation segment effectiveness parameters 2100 may include one or more of: sub-lesion measurements along the ablation segment, placement of sub-lesions comprising the ablation segment, ablation tool (e.g., ablation catheter) settings governing sub-lesion and/or ablation segment formation, calculated results of ablation, and tissue conditions within which the ablation segment is situated. Optionally, ablation segment effectiveness parameters 2100 include other data; for example: patient data parameters, and/or previously acquired ablation data for the same patient. Further details of ablation segment effectiveness parameters 2100 are provided in descriptions with reference to FIG. 14B herein.

Ablation segment effectiveness parameters 2100 may include dielectric measurements. Ablation segment effectiveness parameters 2100 may include indications of conditions of formation of the ablation segment; for example, lesion placement, ablation tool settings governing lesion formation (such as ablation power, dielectric quality of contact, angle of contact, force of contact, and timing of ablation), and/or tissue conditions within which the lesion is situated. Ablation segment effectiveness parameters 2100 may include indications of structure of an ablation segment (e.g., depth, size, volume of tissue etc.).

The inputs of each collection of ablation segment effectiveness parameters 2100 may at least potentially indicate (individually and/or in aggregate) information about the "effectiveness" of the particular ablation segment to which they relate. In some embodiments of the present invention, "effectiveness" is defined in relation to targeted outcomes of cardiac ablation treatments for atrial fibrillation (AF). In AF ablation treatments, an effective ablation segment comprises at least one, and preferably a plurality of sub-lesions in a cardiac wall (i.e., an atrial wall) which together substantially block electrophysiological impulse transmission from passing through, over, and/or under the ablation segment.

In some embodiments, persistence (or permanence) of the ablation segment, its sub-lesions, and/or its impulse blocking characteristics is a criterion of effectiveness. Other definitions of "effectiveness" applicable in some embodiments of the present invention are described hereinbelow. In some embodiments, effectiveness relates to conditions of safety. Optionally, for example, "effectiveness" is at least partially defined as comprising avoidance of some particular outcome, for example, avoiding lesioning of the esophagus, the phrenic nerve, and/or the venous roots, which could lead to serious complications. Optionally, an ablation segment effectiveness estimator is used for any combination of "effectiveness" conditions; additionally or alternatively, a plurality of ablation segment effectiveness estimators is used, which optionally each separately cover a one or more criteria of ablation segment effectiveness.

At block 2103, in some embodiments, a plurality of collections of ablation segment effectiveness parameters 2100 is provided as training set data for use in one or more machine learning methods, in order to generate a learned ablation segment effectiveness estimator 2104 (herein, black dots mark the usual receiving side of a connecting line, e.g., direction of data communication; however, use of this convention does not exclude two-way communication). The example of "machine learning" is used herein as an example of a method of creating an estimator, and should not be considered limiting. Alternatives include, for example general purpose statistical methods and/or estimator definition based on theoretical equations accounting for observed correlations. In some embodiments, training set data used in generating the learned ablation segment effectiveness estimator 2104 are obtained in vivo. In some embodiments, at least part of the training set data used to generate the learned ablation segment effectiveness estimator are obtained in vitro, for example based on ablation of porcine heart wall. Machine learning at block 2103 may be in accordance with techniques described in relation to machine learning 1603.

In some embodiments, an ablation segment effectiveness estimator may be trained (for example as explained in block 2103) from training set data including collections of ablation segment effectiveness parameters 2100 with observed lesion effectiveness 1602; to provide estimated lesion effectiveness 1606; for example: output of ablation segment effectiveness estimator 2104 may be an indication of the transmurality of a single lesion.

In some embodiments, training set data including collections of ablation segment effectiveness parameters 2100 may include examples of positive and negative outcomes. Positive outcome (in other words: effective ablation) may indicate that the ablation segment (e.g., two ablation points) is transmural. Negative outcome can happen for example: as a result of one non-transmural lesion and/or a non-contiguous ablation segment.

Feedback Inputs to Machine Learning

In some embodiments of the invention, for each collection of ablation segment effectiveness parameters 2100 in the training set data, there is also provided as input to block 2103 a corresponding data collection indicating observed ablation segment effectiveness 2102. For example, the observed ablation segment effectiveness optionally includes a measurement showing one or more of the following:

acute electrical isolation is established by the ablation segment at the end of the ablation procedure;

persistent electrical isolation remains for at least 5 days, 30 days, 60 days, 90 days, or another longer, shorter, or intermediate duration after the end of the ablation procedure;

asymptomatic;

hospitalization;

survival;

AF burden <5%;

a fibrotic area corresponding to the ablation segment persists for at least 5, 30, 60, 90, or another longer, shorter, or intermediate period after the end of the ablation procedure; and/or the patient is disease free (at least with respect to conduction across a particular ablation segment) for at least 1 month, 3 months, 6 months, 1 year, 2 years, 5 years, or another longer, shorter or intermediate period after the end of the ablation procedure.

In some embodiments, observed ablation segment effectiveness 2102 relates to safety—for example that the ablation segment was or was not associated with a complication such as damage to the esophagus, damage to the phrenic nerve, damage to the venous roots, and/or a risk-associated event during ablation such as charring or "steam pop". Steam pop is a term for a condition wherein rapid expansion of steam during an ablation creates an audible "pop"; this is associated in the literature with a risk of complications such as heart wall perforation.

In some embodiments, data indicating observed ablation segment effectiveness 2102 may be obtained by the same catheter that was used to form the ablation. For example, a probe of an RF ablation catheter is operated to ablate tissue, and then electrodes of the same catheter are used to measure potential electrical fields induced in the vicinity of the ablation. From these measurements, impedance properties indicating ablation segment and/or sub-lesion state may be calculated. In some embodiments, the impedance properties in turn indicate dielectric properties of tissue that are changed as a result of tissue ablation. Dielectric properties and/or impedance are optionally interpreted as indicating local tissue state and in particular, local tissue state(s) as being permanently ablated (e.g., converted to fibrotic tissue), edematous but not fibrotic, and/or healthy. Data provided as a collection of observed ablation segment effectiveness data 2102 is optionally expressed in any suitable format; for example: voltages, impedances, dielectric parameters, and/or tissue state(s) inferred therefrom. Optionally, another measure of observed ablation segment effectiveness is provided, for example, measurements of electrical isolation (e.g., lack of impulse conduction across the ablation segment), or clinical observation that disease is absent. In some embodiments dynamics of measurements such as impedance measurements are used. For example, impedance at an ablation region is optionally set to a baseline before ablation begins (e.g., as if the tissue is healthy). During and/or after ablation, changes in impedance (drops in impedance, for example) are measured (e.g., at frequencies up to about 1 MHz), and these changes optionally serve as input to an ablation segment effectiveness estimator. The relevant dynamics are optionally provided in terms of magnitude, rate (slope and/or exponent, for example), and/or in terms of function shape, for example, linear, exponential, logarithmic or another shape.

In some embodiments, the impedance measurements include measurements of impedance between different electrodes on a prove of the ablation catheter (e.g., between a tip electrode of the ablation catheter and another electrode on the same catheter), between one or more electrodes on the ablation catheter and one or more electrodes on another catheter, and/or between one of more of the ablation electrodes and one or more body surface electrodes. In some embodiments, the impedance measurements include measurement of impedances at various frequencies, e.g., from about 10 kHz to about 1 MHz.

Optionally, estimates of ablation segment effectiveness 2106 are accompanied by a metric of certainty, for example, sensitivity and/or selectivity. Estimated ablation segment effectiveness 2106 collected along a whole ablation line optionally are configured to identify the most likely location or locations along an ablation line where incomplete electrical isolation occurs or will occur. In some embodiments, estimated ablation segment effectiveness 2106 is displayed within an interactive user interface facilitating use by an operator to examine the estimate of ablation segment effectiveness from different perspectives: for example, to check certainty of results, to check estimated ablation segment effectiveness 2106 corresponding to estimated position of failed electrical isolation along the ablation line, to compare the current ablation segment with other ablation segments in a database which historically have produced similar ablation segment effectiveness estimator results, etc.

Model Input to Machine Learning, and Pre-Processing of Inputs

In some embodiments, the machine learning of block 2103 proceeds on the basis of an assumed ablation segment model 2101. Optionally, ablation segment model 2101 is naïvely structured. For example, it optionally simply hypothesizes for the machine learning of block 2103 a correlation (naïve as to underlying structure) between the prior inputs of ablation segment effectiveness parameters 2100 and the feedback inputs of observed ablation segment effectiveness 2102.

However, it is a potential advantage to at least partially structure inputs based on known physical and/or causal relationships. The structure can be provided as part of ablation segment model 2101, and/or by pre-processing of data provided as inputs. For example, inputs from the ablation segment effectiveness parameters 2100 are optionally pre-processed to be expressed in terms of sub-lesion size (diameter and/or depth, for example). Additionally or alternatively, inputs are structured by the ablation segment model itself into indications of sub-lesion size (e.g., machine learning is applied to a model equation operating on the ablation segment effectiveness parameters in one or more combined terms, rather than only in terms each comprising a different raw ablation segment effectiveness parameters).

Pre-interpretation of raw inputs indicating ablation segment effectiveness (e.g., interpretation of electrical field measurements such as dielectric measurements to identify local tissue state) provides a potential advantage by reducing complexity of the data space (and potentially noise in the data) before applying machine learning to it. However, there is a potential disadvantage in over-simplifying and/or distorting data in observed ablation segment effectiveness 2102 by pre-interpreting, as this can reduce or destroy correlations latent in the raw inputs.

Optionally, use of pre-processing enables creating ablation segment effectiveness estimators which are applicable to different types of raw input. For example, part of the difference between simulations of sub-lesion size (e.g., before ablation) and measurements of sub-lesion size after ablation can be abstracted away by making sub-lesion size itself one of the inputs in the ablation segment effectiveness parameters 2100. That has the potential advantage of facilitating comparison of predictions from a planned procedure with predictions from actual procedure results, for example.

In some embodiments, the raw measurements indicating ablation segment effectiveness (e.g., electrical field measurements such as dielectric measurements) may be used as ablation segment effectiveness parameters 2100 (e.g., without any calculations) and may be input as training set data.

Learned Ablation Segment Estimator

After the above-described inputs are suitably defined and received for a plurality of sub-lesions (e.g., 50, 100, 1000, or another larger, smaller, or intermediate number of sub-lesions), machine learning at block 2103 may use one or more machine learning methods to produce a learned ablation segment effectiveness estimator 2104. Examples of machine learning methods used in some embodiments of the present invention include, for example: decision tree learning, association rule learning, an artificial neural network, deep-learning artificial neural network, inductive logic programming, a support vector machine, cluster analysis, Bayesian networks, reinforcement learning, representation learning, similarity and metric learning, semi-supervised learning (for example: multi instance learning) and/or another technique taken from the art of machine learning. In some embodiments, the estimator output (e.g., estimated segment effectiveness) may include a binary prediction (e.g., +1, −1). In some embodiments, the estimator output (e.g., estimated segment effectiveness) may include a probabilistic output between zero and one (e.g., a dynamic score). Such embodiments may be advantageous when using an estimator during an ablation procedure. For example it may facilitate a user's decision whether to proceed or complete the procedure, and/or whether to adjust the ablation plan.

In some embodiments, the learned ablation segment effectiveness estimator 2104 comprises a set of learned weights applied to terms of ablation segment model 2101. Application of the ablation segment effectiveness estimate at block 2105 comprises plugging into the model appropriate values from a collection of ablation segment effectiveness parameters 2100, and calculating the result. The result is produced as an estimated ablation segment effectiveness 2106. Other collections of ablation segment effectiveness parameters 2100 may refer to ablation segment effectiveness parameters 2100 collected after learned ablation segment effectiveness estimator 2104 was created, e.g., ablation segment effectiveness parameters 2100 collected in run-time during a medical procedure. Other collections of ablation segment effectiveness parameters 2100 may include dielectric measurements measured run-time during a medical procedure. Such dielectric measurements may be used as inputs to learned ablation segment effectiveness estimator application 2105 to obtain estimates of ablation segment effectiveness 2106.

It should be noted that learned ablation segment effectiveness estimator 2104 may be updated and/or adjusted (also referred to as refreshed) based on such other collections of ablation segment effectiveness parameters 2100. Estimates of ablation segment effectiveness 2106 may be used to adjust an ablation plan.

In some embodiments, the estimated ablation segment effectiveness 2106 is expressed in the same terms as used by ablation segment model 2101 for learning. Optionally, the estimated ablation segment effectiveness 2106 is also accompanied by an estimate of the certainty of the prediction, for example, based on statistically determined specificity and/or sensitivity. Optionally, post-processing is applied to convert the estimated ablation segment effectiveness 2106 into another form. For example, the feedback input in the observed ablation segment effectiveness 2102 may not itself encode a spatial extent of the region electrically isolated by a particular ablation segment. Rather, for example, it may simply indicate that the electrical isolation is sufficient to maintain disease prevention across the ablation segment. Since this implies that sub-lesions contributing to the ablation segment are transmural, it is possible, optionally, to infer at a later stage that the depths of these sub-lesions are about the same as the thickness of the tissue. Similarly, the positions and sizes of adjoining sub-lesions optionally provide post-processing constraints on sub-lesion diameter within an ablation segment.

It should be understood that it is often possible to alternatively make such adjustments in a stage of pre-processing (rather than post-processing). For example evidence of "successful block" is optionally converted to size constraints in the feedback input indicating observed ablation segment effectiveness 2102. In some embodiments, constraints may be accounted for in the ablation segment model 2101 itself; for example, by defining ablation segment model 2101 to include a term comparing sub-lesion depth to atrial wall width.

Inputs to Ablation Segment Effectiveness Estimators

Figure 14B:
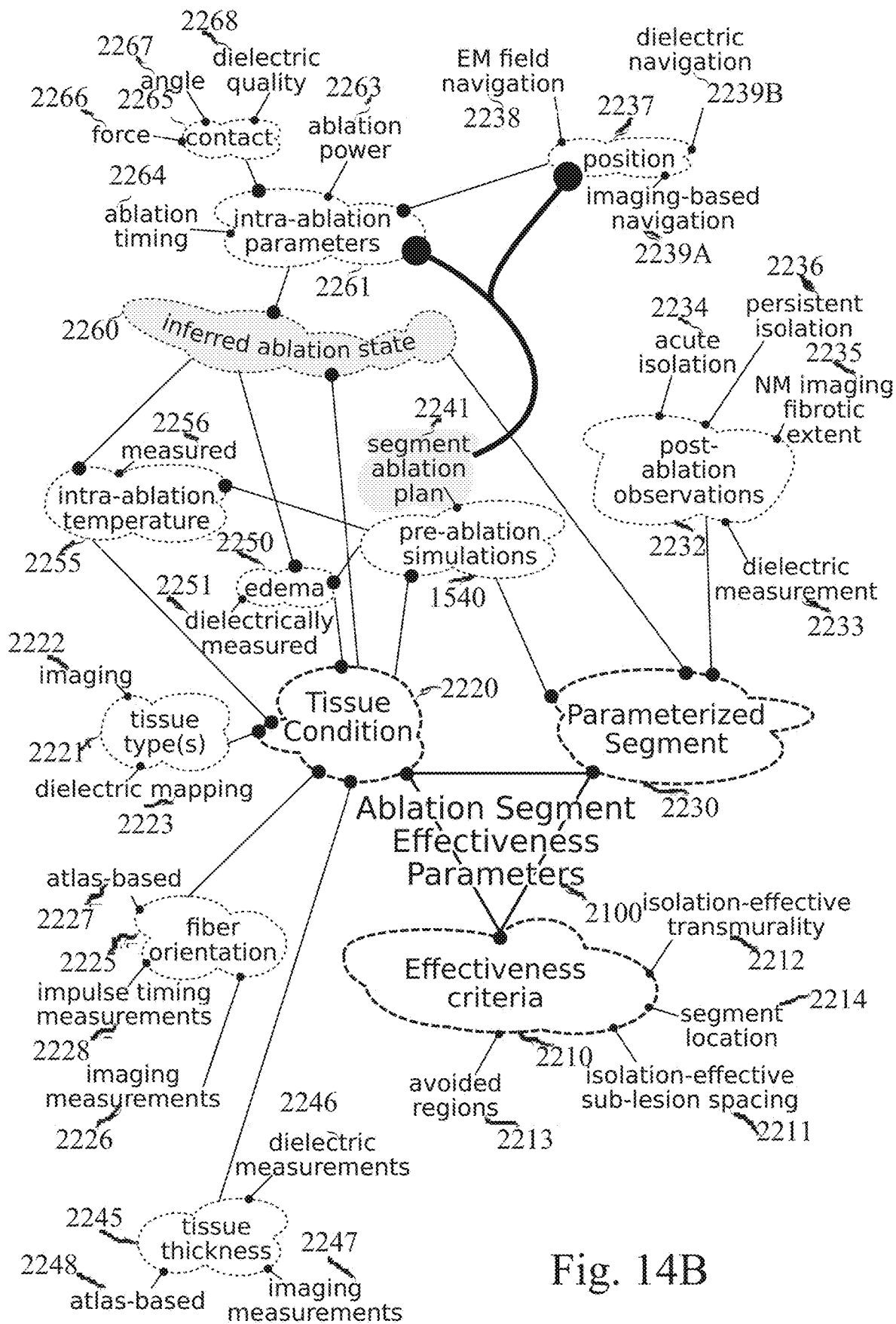
FIG. 14B schematically represents a range of options for prior inputs to an ablation segment effectiveness estimator and/or for machine learning of the estimator, comprising parameters potentially relating to ablation segment effectiveness, according to some embodiments of the present disclosure.

Reference is now made to FIG. 14B, which schematically represents a range of options for prior inputs to a ablation segment effectiveness estimator and/or for use in machine learning of the ablation segment effectiveness estimator, comprising parameters potentially relating to ablation segment effectiveness, according to some embodiments of the present disclosure.

The number of possible separate inputs to a collection of ablation segment effectiveness parameters, in some embodiments, is both large and optionally variable. Sets of ablation segment effectiveness parameters 2100 used, in some embodiments, and/or portions of such sets are also referred to herein as "input data" The inputs listed in FIG. 14B may be viewed as providing a menu of examples of parameters, from which any suitable subset is optionally used. Optionally, another parameter source not shown among those in the FIG. 14B is used.

The broadly hierarchical (mostly branched, but in some places looping) arrangement by which optional inputs are shown in FIG. 14B is primarily used as a guide to help organize the descriptions that follow. Terminal nodes (terms without borders) represent numerous types of basic inputs (e.g. measurements, settings, and outside data such as anatomical atlas data). Nodes surrounded by thin cloud-shaped borders list intermediate organizational concepts that link the basic inputs (and/or other organizational concepts) as alternative and/or complementary contributions to the full collection of ablation segment effectiveness parameters 2100, as detailed for each. Optionally (as indicated in the more detailed descriptions following), some of the cloud-bordered nodes represent higher level abstractions used in the ablation segment effectiveness parameters in place of one or more basic inputs (e.g., transformation of ablation parameters to an expected ablation state). With regard to the higher level abstractions described in particular, an ablation segment effectiveness estimator may or may not receive such information as part of ablation segment effectiveness parameters it receives. Such abstractions can help in the generation and/or use of an ablation segment effectiveness estimator for such reasons as providing prior accounting for variance and/or assisting in referencing estimator results to different types of raw input. However, they are often themselves based on estimates and/or theoretical considerations which the actual may or may not fully support.

Next to the triangle that indicates the root of the hierarchy of ablation segment effectiveness parameters 2100 are three clouds with thicker borders. These define a basic conceptual division of the ablation segment effectiveness parameters into three: (1) parameters indicating information about size and/or position of the ablation segment itself (parameterized ablation segment 2230, which may be said to be characterized by ablation segment parameterizing data), (2) parameters indicating information about the tissue environment in which the ablation segment is placed (tissue condition 2220), and (3) effectiveness criteria 2210, which define empirical, theoretical, clinical, and/or safety conditions within which an ablation procedure is operating.

Apart from the organization just described, the parameters of FIG. 14B belong to one or more of three time stages:

Pre-ablation Inputs indicate, for example, results of planning activities (ablation line definition, pre-ablation simulations of sub-lesion extent, effects on ablation segment of different spacings, etc.).

Intra-Lesioning Inputs include, for example, measurements taken and operational parameters used during an ablation procedure (optionally including parameters measured immediately after ablation but before the overall procedure ends).

Post-Lesioning Inputs include, for example, clinical observations in the period after the procedure ends (day to years), post-procedure imaging, and/or follow-up catheterization procedures.

For some parameters, stages are explicitly mentioned in FIG. 14B (e.g., as pre-ablation simulation 2240, intra-ablation parameters 2261, and post-ablation observations 2232). Staging relevant to other inputs is mentioned where those inputs are described.

Ablation Segment Parameterization

Starting now from the node for parameterized ablation segment 2230 ("segment" is again used in the figure as a shorthand for "ablation segment"): In some embodiments, the ablation segment is parameterized based on one or more of pre-ablation simulations 2240, post-ablation observations 2232, inferred ablation state 2260 after ablation (e.g., a high-level description of sub-lesion positions and sizes which is optionally inferred from measurements and/or activities), and/or any of the other parameters which are shown feeding into these nodes. Inferred ablation state 2260 may include one or more states inferred from dielectric measurements and/or any manipulation (such as mathematical manipulation) on such dielectric measurements). Inferred ablation state 2260 may include one or more results inferred from dielectric measurements by analytical calculations and/or machine learning techniques.

In some embodiments, the ablation segment and/or its sub-lesions is/are parameterized non-geometrically in the collection of ablation segment effectiveness parameters 2100 supplied to an ablation segment effectiveness estimator. For example, a dielectric measurement 2233 optionally provides information about how much local tissue in the region of a measurement electrode has been ablated, without necessarily providing information about how the ablation segment and/or its sub-lesions is shaped. Potentially, a non-geometrical parameterization may still provide enough information for machine learning to converge on an estimator linking the ablation segment parameterization to an estimated ablation segment effectiveness.

Additionally or alternatively, in some embodiments, the ablation segment and/or its sub-lesions is/are parameterized as a geometrical object having a defined shape. An ablation segment is optionally parameterized by one or more distances between a plurality of sub-lesions (which potentially affects the appearance of transmission gaps), and/or by a time elapsed between creation of the sub-lesions. Optionally elapsed time is measured between initiations of ablations, terminations of ablations, termination of one ablation and initiation of another, or any other suitable definition of elapsed time. Elapsed time could affect ablation segment shape due to merging of sub-lesions affected by residual temperature increases; and/or due to changes in edematous state, for example due to recent nearby ablations.

Optionally, a geometrical parameterization of sub-lesion shape defines at least a sub-lesion depth and a proximal diameter (diameter of a sub-lesion at the side directly in contact with the ablation device). Optionally, these parameters are incorporated into a definition of a geometrical solid representing the shape of the sub-lesion; for example, a frustum of a paraboloid, ellipsoid, cone, or another shape. Parameterization of ablation segment and/or its sub-lesions as geometrical shapes, though potentially subject to estimation errors of its own, has the potential advantage of being interconvertable between outputs of pre-ablation simulation 2240, inferred ablation results 2260 (and/or intra-ablation parameters 2261), and/or post-ablation observations 2232.

Optionally, such interconvertibility allows the same estimator to be used on data from different original sources. Additionally or alternatively, a non-spatial "common parameterization" is used. For example, a spatial definition of an ablation segment and/or its sub-lesions determined by simulation is optionally re-parameterized into the results of simulated "measurements" that would be expected from it. Optionally, re-parameterization is used to convert ablation segment effectiveness parameters size measurements known from in vitro studies into ablation segment effectiveness parameters more convenient for direct in vivo use, and/or conversely.

Each of the three main ablation segment parameterizing data stages is now discussed in turn.

In some embodiments, pre-ablation simulations 2240 produce parameterized descriptions of ablation segments (and/or their sub-lesions) which are planned to be formed during an ablation procedure. The pre-ablation simulations 2240 are based on an ablation segment ablation plan 2241 describing where and how ablations are to be made. Optionally the simulation results are further modulated by relevant parameters of tissue condition 2220 (e.g. tissue thickness 2245, state of edema 2250, tissue type(s) 2221, fiber orientation 2225, and/or intra-ablation temperature 2255; each is further described below). Optionally, the pre-ablation simulation 2240 is produced as part of creating the ablation segment ablation plan 2241 in the first place. Tissue thickness 2245 may be calculated and/or inferred (e.g., by machine learning methods) from dielectric measurements 2246.

Insofar as the pre-ablation simulation 2240 optionally comprises spatially defined simulations such as EM and/or thermal simulation, it is relatively straightforward, in some embodiments, to define the parameterized ablation segment 2230 in terms of geometrical shape.

In some embodiments, parameterized ablation segment 2230 is based on inferred ablation results 2260. Similarly as for pre-ablation simulations 2240, the inferred ablation results estimate the effects of parameters used during ablation, optionally modulated by the parameters of tissue condition 2220. However, instead of choosing ablation parameters from an ablation plan 2241 (e.g., as indicated by the connection in FIG. 14B shown between segment ablation plan 2241 and intra-ablation parameters 2261), the intra-ablation parameters 2261 used in actual ablation are used. Examples of intra-ablation parameters 2261 include ablation probe contact 2265, ablation power 2263, ablation timing 2264, and optionally other ablation parameters not shown, such as phase and/or frequency.

In some embodiments, contact 2265 is measured and/or estimated based on force measurements 2266 (e.g., measurements by one or more force sensors on the ablation probe), dielectrically-measured quality of contact 2268, and/or angle 2267 of probe contact with tissue, which can be measured, for example, by comparing readings from a plurality of force sensors, and/or based on indications of dielectrically measured quality of contact. Dielectric measurement of contact quality is described, for example in International Patent Application No. PCT/IB2016/052686. Optionally, any combination of one or more of the parameters used and/or measured during ablation are used directly by an ablation segment effectiveness estimator, optionally without the prior interpretation represented by inferred ablation results 2260.

In some embodiments, dynamics of contact (under any suitable measure of contact) is provided as an ablation segment effectiveness estimator input. As heart tissue moves (e.g., in synchrony with the heartbeat and/or respiratory cycles), an ablation probe in contact with tissue may move relative to the tissue. With lowered relative motion dynamics, in some embodiments, an ablation segment effectiveness estimator is potentially more likely to predict a higher effectiveness of an ablation segment. In some embodiments (e.g., for ablation segment effectiveness estimation during pre-planning), a prediction of relative motion dynamics is made for a particular heart region based on experience of this parameter in different heart regions. Optionally, a simulation of heart motion is used to predict relative ablation probe/cardiac tissue motion dynamics, e.g., under contact pressures typical for ablation procedures.

Also comprising ablation segment effectiveness parameters 2100, in some embodiments, are measured positions 2237 of the probe, which can be measured, for example, based on electromagnetic field-guided navigation 2238, dielectrically-guided navigation 2239B, and/or imaging-based navigation 2239A. In some embodiments, the probe is moved to be placed at measured positions 2237 based on indications in segment ablation plan 2241 (e.g., as indicated by the connection in FIG. 14B shown between segment ablation plan 2241 and positions 2237).

In some embodiments, post-ablation observations 2232 are made. The post-ablation observations 2232 optionally include one or more dielectric measurements 2233 characterizing tissue in the region of the ablation segment and/or sub-lesion, measurements of acute electrical isolation 2234 (that is, measurements made within the time of the initial ablation procedure), measurements of persistent electrical isolation 2236 (that is, measurements and/or clinical observations made in the days, months, and/or years after the initial ablation procedure), and/or measurements made by imaging 2235, for example, nuclear medicine imaging of fibrotic extent. Use of dielectric measurements for characterizing ablated/lesioned and/or other tissue states such as edema, is described, for example, in International Patent Application Nos. PCT/IB2016/052690 and PCT/IB2016/052686. In some embodiments, an intracardiac electrogram is measured in the region of an ablation segment and used as an input to an ablation segment effectiveness estimator. Dynamics of the electrogram during and/or after lesioning are potentially indicative of likely ablation segment effectiveness, according to an amount of amplitude decay from a base amplitude pre-ablation (more decay being generally associated with greater effectiveness).

Optionally, an ablation procedure is completed by making post-ablation observations at positions near ablation segments and/or along the ablation line which the ablation segments define. In some embodiments, the post-ablation observation positions are suggested automatically, for example, to check on tissue state at the locations between sub-lesions most at risk for allowing electrical reconnection (optionally, this risk is itself determined by use of the ablation segment effectiveness estimator), and/or to check the sub-lesions where there was some indication of problems during the ablation procedure itself.

Tissue Condition Influences on Ablation Segment Effectiveness

Turning now to tissue conditions 2220, several main relevant conditions were listed already above in relation to pre-ablation simulations 2240, and inferred ablation state 2260. In some embodiments, at least some of the tissue conditions 2220 are provided as part of the ablation segment effectiveness parameters 2100. For example, a sub-lesion partially characterized in the ablation segment effectiveness parameters by its depth may be transmural or not (and thus electrically isolating or not) depending on the thickness 2245 of the tissue ablated. Similarly, an ablation segment may more or less isolating depending on the local orientation 2225 of myocardial fibers.

In contrast, some tissue conditions shown are effectively accounted for, in some embodiments, by the parameterization of the ablation segment 2230. These can be optionally be left out of the ablation segment effectiveness parameters based on which machine learning and/or effectiveness estimation are performed. For example, temperature measured during ablation may affect how an ablation segment is parameterized, but leave little residual effect affecting the estimation of ablation segment effectiveness.

In some embodiments, tissue conditions are provided as input to an ablation segment effectiveness estimator indirectly, for example, as an indication of a region (e.g., a cardiac region) where an ablation is placed. Effects associated with a particular region are optionally due to a number of more specific effects (e.g., typical thickness, fiber orientation, thermal properties, etc.) which may or may not be explicitly available as inputs. The use of machine learning potentially allows accounting for such effects implicitly, through associated position information.

Tissue thickness 2245 is a factor partially governing transmurality. Thicker tissue potentially requires deeper ablation in order to achieve effective electrical isolation. Thickness is optionally characterized based on tissue atlas information 2248, and/or based on imaging measurements 2247 obtained by analysis of anatomical images of the individual patient (obtained, e.g., by MRI, CT, nuclear medicine, or another method).

Intra-ablation temperature 2255 is optionally simulated in pre-ablation simulations 2240, inferred from actual ablation parameters as part of inferred ablation results 2260, and/or measured 2256 during ablation. With RF ablation, for example, temperature can be an indication of ablation progress. In some embodiments dynamics of temperature serve as an input. For example, temperature measured at an ablation probe tip which rises and maintains stability during ablation is potentially an indication of successful ablation, while a temperature which drops is potentially and indication of less likely success.

Similarly, edema may be simulated, inferred, or dielectrically measured 2251. Edema in cardiac tissue is potentially elicited by nearby ablations, or even by rough contact with a probe. Edematous tissue is potentially more resistant to effective ablation: for example, edematous fluid can thicken tissue so that sub-lesion transmurality is harder to achieve.

Tissue type 2221 is optionally characterized (typically before a procedure) by one or more imaging modalities 2222. Tissue type 2221 can also be characterized intra-procedure by dielectric mapping 2223 (and/or impedance mapping), for example as described in relation to FIG. 4A.

In some embodiments, impedance mapping (optionally omitting conversion to a dielectric map) itself is performed at one or more frequencies, e.g., frequencies up to about 1 MHz. Impedance maps, and/or maps of impedance dynamics, optionally provide indications of (e.g., correlate with) one or more of the following:

Initial wall composition (e.g., living or fibrotic);
Heat conduction of neighboring organs (e.g., lung is less heat conducting);
Contact quality;
Wall thickness;
Tissue temperature;
Wall tissue decomposition (e.g., upon ablation);
Contact quality stability;

Several of these uses of impedance are described in connection to particular elements of FIG. 14B. It is noted that impedance measurements of these parameters are potentially at least somewhat entangled, statistically. However, correlations with other inputs, for example, other measurements, past observations, particular conditions of the measurement (e.g., force, position, current operations), etc. potentially assist in separation. It is noted that attribution of measured impedance characteristics to particular causes is not necessarily required and/or performed by an ablation segment effectiveness estimator, insofar as machine learning can operate on associations between observations without necessarily using and/or forming specific attributions of measurements to causes.

In some embodiments of the invention, the level of spatial resolution of adjacent features provided by the dielectric mapping 2223 is between about 0.1 and 1 mm. Optionally, the spatial resolution is about 0.1 mm, about 0.5 mm, 1 mm, 2 mm, 5 mm, or another larger, smaller, and/or intermediate value. In some embodiments, the map is made available for display to an operator.

Fiber orientation 2225 is discussed in detail herein in relation to FIGS. 5A-5B. The effectiveness of an ablation segment for creating electrical isolation is potentially affected by the direction of myocardial fibers running nearby: for example, fibers oriented to run through a gap (for example, as in FIG. 5B) apparently transmit impulses more efficiently than fibers oriented so that impulses must jump laterally from fiber to fiber to pass the gap (for example, as in FIG. 5A). Optionally, fiber orientation used in simulating or inferring ablation effects is derived from atlas-based assumptions 2227 about heart wall anatomy. Additionally or alternatively, fiber orientation is imaged 2226, for example, using echocardiography-based shear wave imaging, and/or diffusion tensor imaging. In some embodiments, fiber orientation between two points is inferred from the rate of impulse transmission 2228 therebetween. Optionally superficial fiber orientation is indicated by differences in contact indicated by impedance measurements made as an electrode travels, for example, along (in the direction of) or across (at least partially orthogonal to) a direction of fiber orientation.

In some embodiments of the invention, patient data parameters (also referred to herein as "patient data") are also provided as part of ablation segment effectiveness parameters 2100.

Optionally, any of the above, or another type of patient data, are used directly as inputs to machine learning. In some embodiments, factors which are particularly associated with risk (gender, left atrial appendicular morphology, alcohol consumption, obesity, hypertension, obstructive sleep apnea, age, etc.), and optionally still more particularly risk of mortality or morbidity as a result of having to re-perform a procedure, are used to set a threshold of acceptable ablation segment effectiveness. For example, during ablation plan adjustment, an automatic algorithm is optionally set to be more aggressive in indicating a potentially ineffective ablation segment, and/or more aggressive in making suggestions for mitigation of potentially ineffective ablation segments. In some embodiments, determination of elevated risk (or another patient-specific input) optionally leads to a suggestion to follow a qualitatively different plan: for example, to ablate along a different ablation path.

In another example: during ablation, an automatic algorithm estimates expected clinical outcome for a plurality of parameter sets of further ablation, e.g., expected outcome if the next ablation site is placed at a plurality of alternative positions, and/or if the next ablation begins (or potentially does not) within a given time period. The estimations of the clinical outcomes for different parameter sets may be displayed to the physician, who may choose between them. The physician's choice may be based on considerations such as the difference in the expected outcome and the difference in the difficulty of obtaining the required ablation parameters in a set. For example, if ablating at region that is difficult to reach with the catheter from its current position brings only slightly better results than ablating at a second region that is easier to reach, the physician may choose the second region.

Optionally, data indicating therapeutic strategy and/or events (as described above) are included in the ablation segment effectiveness parameters 2100.

Effectiveness Criteria

In some embodiments, effectiveness criteria 2210 are incorporated to the ablation segment effectiveness parameters. Optionally effectiveness criteria 2210 comprise criteria defining limits on what features of an ablation segment are expected to be needed in order for it to be an effective ablation segment. These can include, for example, descriptions of sub-lesion/tissue parameter pairings that are expected, based on theoretical and/or empirical data to allow and/or prevent effective transmurality of block (isolation-effective transmurality 2212). In some embodiments, ablation segment location 2214 itself is considered part of the ablation segment effectiveness parameters, since ablation segments should be positioned where they interfere with impulse transmission. Overall distribution of ablation segments will usually fit one of a small number of general profiles, such as encircling of pulmonary veins with one large loop or with a plurality of smaller loops.

Also optionally defined as part of the ablation segment effectiveness parameters is an empirical and/or theoretical model of how close inter-sub-lesion gaps defining ablation segments should be in order to produce effective block (isolation-effective sub-lesion spacing 2211). A distinction may be made between embodiments in which an ablation segment effectiveness estimator is at least initially uninformed as to this parameter, and embodiments of ablation segment effectiveness estimators which use it. An initially uniformed, machine-learned ablation segment effectiveness estimator potentially arrives at explicit or implicit estimation of what spacings between sub-lesions are effective by reference to the data of its training set, without any prior conditions on what the spacing should be. However, the learning of an informed machine-learned ablation segment effectiveness estimator is potentially "helped along" by such prior data; for example, for example, because a potentially significant part of the training set variance is already explained and/or attributed.

Optionally, effectiveness criteria 2210 relate to regions where ablation should be avoided (avoided regions 2213). These places optionally include, for example, sub-lesions located too near to the esophagus, too near the phrenic nerve, and/or too near the venous roots. Constraints such as avoided region 2213 optionally provide a potential advantage, e.g. for indicating whether or not an ablation plan is safe, and/or for indicating a potential for complications, in case the ablation procedure has already been performed. Additionally or alternatively, other safety constraints are used; for example, constraints on maximum power settings, maximum duration of ablation, etc., which, if exceeded, could indicate an increased potential for complications during and/or after a procedure.

Application and Dynamic Adaptation of an Ablation Plan

Figure 12:
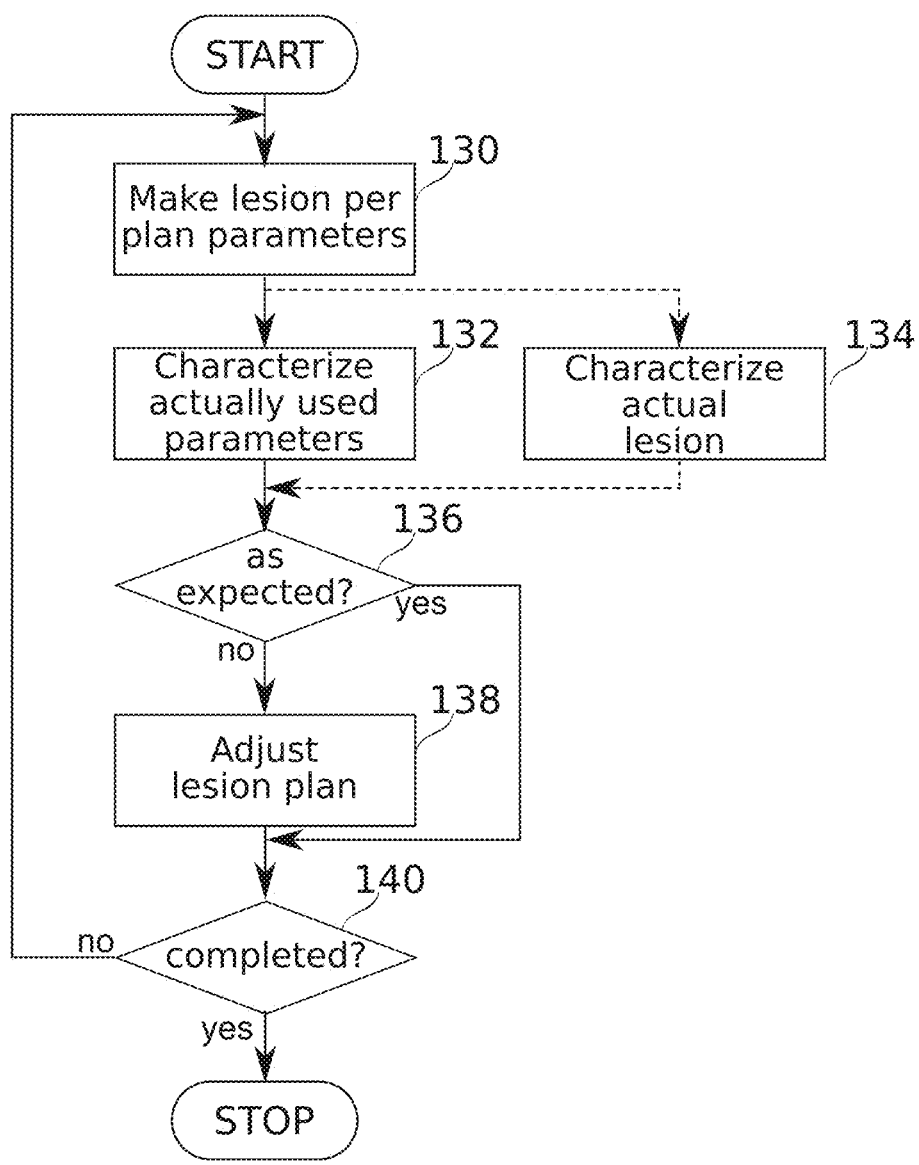
FIG. 12 schematically illustrates a method of real-time use of an ablation plan with optional adjustment, in accordance with some exemplary embodiments of the present disclosure.
Figure 13A:
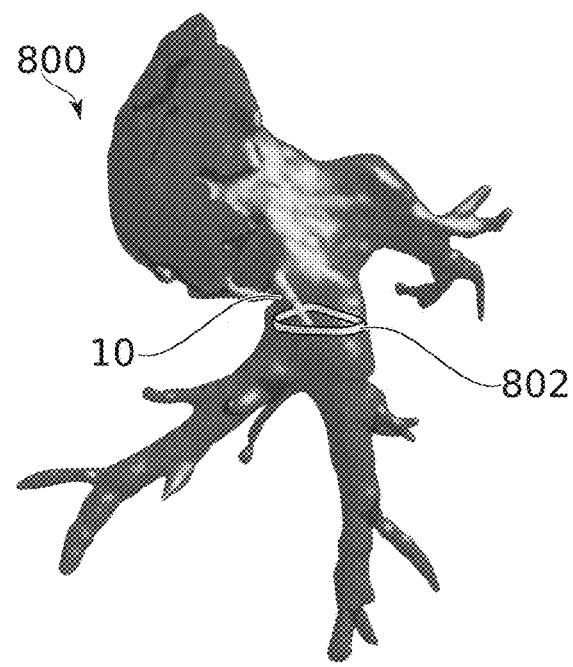
FIG. 13A illustrates the 3-D display of a planned lesion ablation line for a left atrium, along with an ablation probe, in accordance with some exemplary embodiments of the present disclosure.
Figure 13B:
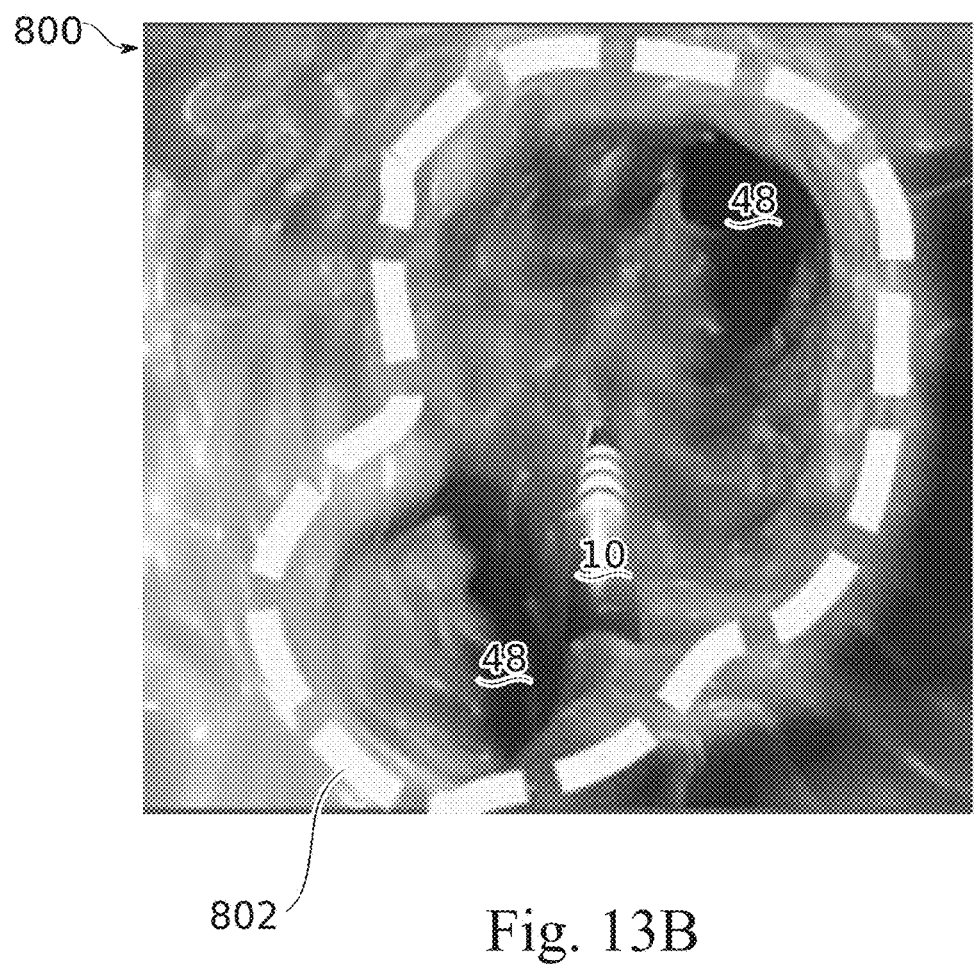
FIG. 13B illustrates an interior-D view of left atrium, probe, and planned ablation line, in accordance with some exemplary embodiments of the present disclosure.

Reference is now made to FIG. 12, which schematically illustrates a method of real-time use, with optional adjustment, of an ablation plan, in accordance with some exemplary embodiments of the invention. Reference is also made to FIG. 13A, which illustrates the 3-D display of a planned lesion ablation line for a left atrium 800, along with an ablation probe 10, in accordance with some exemplary embodiments of the invention. Reference is further made to FIG. 13B, which illustrates an interior 3-D view of left atrium 800, probe 10, and planned ablation line 802, in accordance with some exemplary embodiments of the invention.

In some embodiments, a line of planned ablation 802, together with parameters of planned sub-lesions may be used during a procedure by combining measured ablation probe positions within the body with cues to guide operation of the ablation probe so that the previously determined ablation plan is followed.

The flowchart begins (after production or receiving of an ablation plan). The ablation plan may be provided by a lesion planning system (for example as described in International Patent Application No. PCT/IB2016/052688, the contents of which are included by reference herein in their entirety) or may be provided by the user (e.g., the physician).

At block 130, in some embodiments, a portion of a planned lesion is made (e.g., a sub-lesion comprising ablation from a fixed ablation probe location, or a dragged-out portion of a lesion). A planned lesion may include one or more planned ablation segments. Optionally, the lesion is made in conjunction with visual guidance provided to the user, for example, visual guidance as shown in FIGS. 13A-13B. In FIG. 8A, visual guidance is presented from an outside-the-heart point of view. In FIG. 13B, the point of view is that of a probe of the ablation catheter itself, shown as if from within a heart chamber emptied of blood. Optionally, as the actual ablation probe is moved, its motions (measured, for example, by system 1100 of FIG. 1A) are shown also in a live presentation of the views of FIG. 13A and/or FIG. 13B. In some embodiments, the display is adjusted to also include anatomically realistic tissue coloring and/or responsiveness to ablation probe contact and/or to the effects of ablation itself.

Optionally, selection of pre-planned ablation parameters is automatically made when an ablation probe approaches the next planned lesion position. Optionally, the system guides the user to the next planned lesion position. Optionally, a user is provided with an interface which allows modifying or overriding these settings.

In some embodiments, the system adapts the ablation plan to actual events during ablation, for example, as now described in relation to blocks 132, 134, 136, 138, and 140. In some embodiments, the system adapts the ablation plan in response to one or more estimations of ablation line effectiveness, for example: lesion effectiveness, ablation line effectiveness, and/or ablation segment effectiveness. Estimated ablation line effectiveness may be obtained from one or more estimators (for example: as described in FIG. 6).

At block 132, in some embodiments, the system 1100 characterizes parameters such as ablation probe position and settings of the actual ablation operation performed (optionally, the ablation operation set to be performed based on the current ablation probe position and settings). Optionally, information about the ablation probe position includes a contact force or other assessment of contact quality (e.g. dielectric property contact quality assessment) between the ablation probe and target tissue. Optionally, the new state of tissue in the lesioned region is modeled, based on actual ablation position and parameters, and on data previously configured for thermal simulation. Additionally or alternatively, at block 134, in some embodiments, the lesion actually created is itself characterized, for example, by the analysis of dielectric measurements and/or temperature readings. In some embodiments, at block 134, lesion effectiveness, ablation line effectiveness, and/or ablation segment effectiveness are estimated.

In some embodiments, block 134 may include application of a segment effectiveness estimator, lesion estimator, ablation line estimator, using any suitable inputs available from blocks 132 and 134, and/or from previously available data; for example as described in relation to block 2105 of FIG. 14A, block 1605 of FIG. 1B or 1805 of FIG. 6.

At block 136, in some embodiments, a determination is made as to whether or not the plan is still being followed as currently defined and/or whether the lesion is effective. In some embodiments, block 136 may include a determination as to whether or not the resulting estimated ablation segment effectiveness (corresponding, in some embodiments, to block 2106 of FIG. 14A) indicates that an effective ablation segment has been formed (e.g., by placement of the most recent sub-lesion), and/or will be formed if the next sub-lesion is created as already planned. Any given sub-lesion optionally both completes a previous ablation segment and begins a new sub-lesion, so there may be one ablation segment effectiveness evaluation based largely on parameters describing and/or measuring what has happened already, and another ablation segment effectiveness evaluation which includes assumptions about future (planned) ablations.

If the plan is to remain unchanged, flow continues at block 140. For example, if the ablation segment effectiveness estimator result indicates an effective ablation segment is being and/or has been produced, the flowchart continues with block 140.

Otherwise, at block 138, in some embodiments, the ablation plan is adjusted. Adjustment may be made in any parameter of the ablation plan to adjust, for example: to a deviation from the previously planned timing and/or placement of sub-lesions, to a deviation from an expected effect of a lesioning operation (as measured, for example, from dielectric measurements of lesion extent), and/or for a deviation from an expected pre-lesion tissue state (for example, an expected pre-existing lesion is found to be of a different extent; measured, for example, by dielectric measurements and/or measurements to assess functional blockage of impulse transmission).

In some embodiments, the adjustment is selected so that the ablation segment effectiveness estimator estimates that the new resulting ablation segment will be effective. Underlying reasons for a currently poor ablation segment effectiveness estimator result potentially include, for example:

Deviation from the previously planned timing and/or placement of sub-lesions;

Deviation from an expected effect of an ablation operation (as measured, for example, from dielectric measurements of sub-lesion extent); and/or Deviation from an expected pre-ablation tissue state (for example, an expected pre-existing lesion is found to be of a different extent).

The ablation segment effectiveness estimator itself does not necessarily report reasons for a poor effectiveness estimate. Nevertheless, in some embodiments this is apparent from one or more of the ablation segment effectiveness estimator inputs (particularly if deviating from a planned result), and/or from the types of planned adjustments which restore a more confident ablation segment effectiveness estimate. Optionally, adjustment is based on inspection of the ablation segment effectiveness estimator inputs by a user.

In some embodiments, the ablation segment effectiveness estimator itself is used to automatically generate a suggested ablation plan alteration, for example by trying several different ablation plan adjustment options (for example using an effectiveness maximization search and/or an exhaustive search of effectiveness expected from key parameter changes), and presenting one or more of the best scoring ones for a user to select from. In some embodiments, the ablation line estimator and/or lesion estimator may be used to automatically generate a suggested ablation plan alteration.

In some embodiments, adjustment may include generating plurality of ablation plans, and selecting one of the plurality of ablation plans for use. For example, the user may select one of the plurality of plans, e.g., based on estimated indication of effectiveness.

For example, if a sub-lesion was placed with too large a gap between it and an adjacent sub-region, the plan may be adjusted to fill in the gap region. In another example, if more time has passed between sub-lesions than the current plan anticipates (such that there has been too much cooling in the interim), the recommended placement of the next sub-lesion is brought closer to the previous lesion. For example, if a sub-lesion was estimated to be non-effective, the plan may be adjusted to re-ablate, optionally at a higher power level and/or for a longer duration.

At block 140, in some embodiments, a determination is made as to whether or not the ablation plan has been adequately completed (e.g., according to completion of the planned sequence of steps, and/or based on verification measurements of the actual lesion). A determination as to whether or not the ablation plan has been adequately completed may be based on one or more of lesion effectiveness, ablation line effectiveness, and/or ablation segment effectiveness. For example, if an ablation line estimator (e.g., estimator 1804) estimates that the line is not effective, the flowchart returns to block 130 or block 138.

If not, the flowchart returns to block 130. Otherwise, the flowchart ends.

The flowchart is optionally re-entered as many times as necessary to complete an overall ablation line.

Visualizations Used with an Ablation Segment Effectiveness Estimator

Figure 15A:
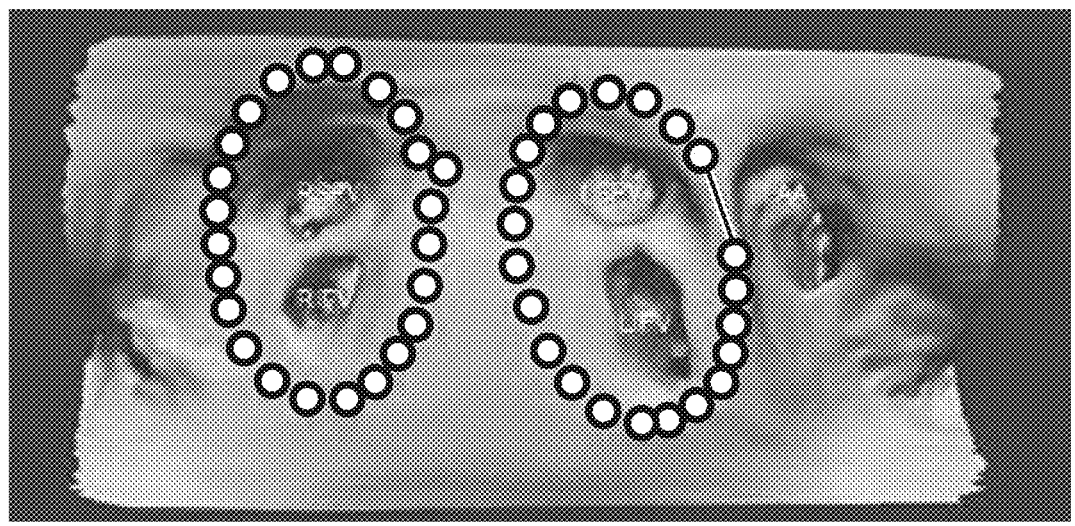
FIG. 15A schematically represents a visualization of results of an ablation segment effectiveness estimator applied to a plurality of ablation segment used in forming ablation lines within a left atrium, according to some embodiments of the present disclosure.
Figure 15B:
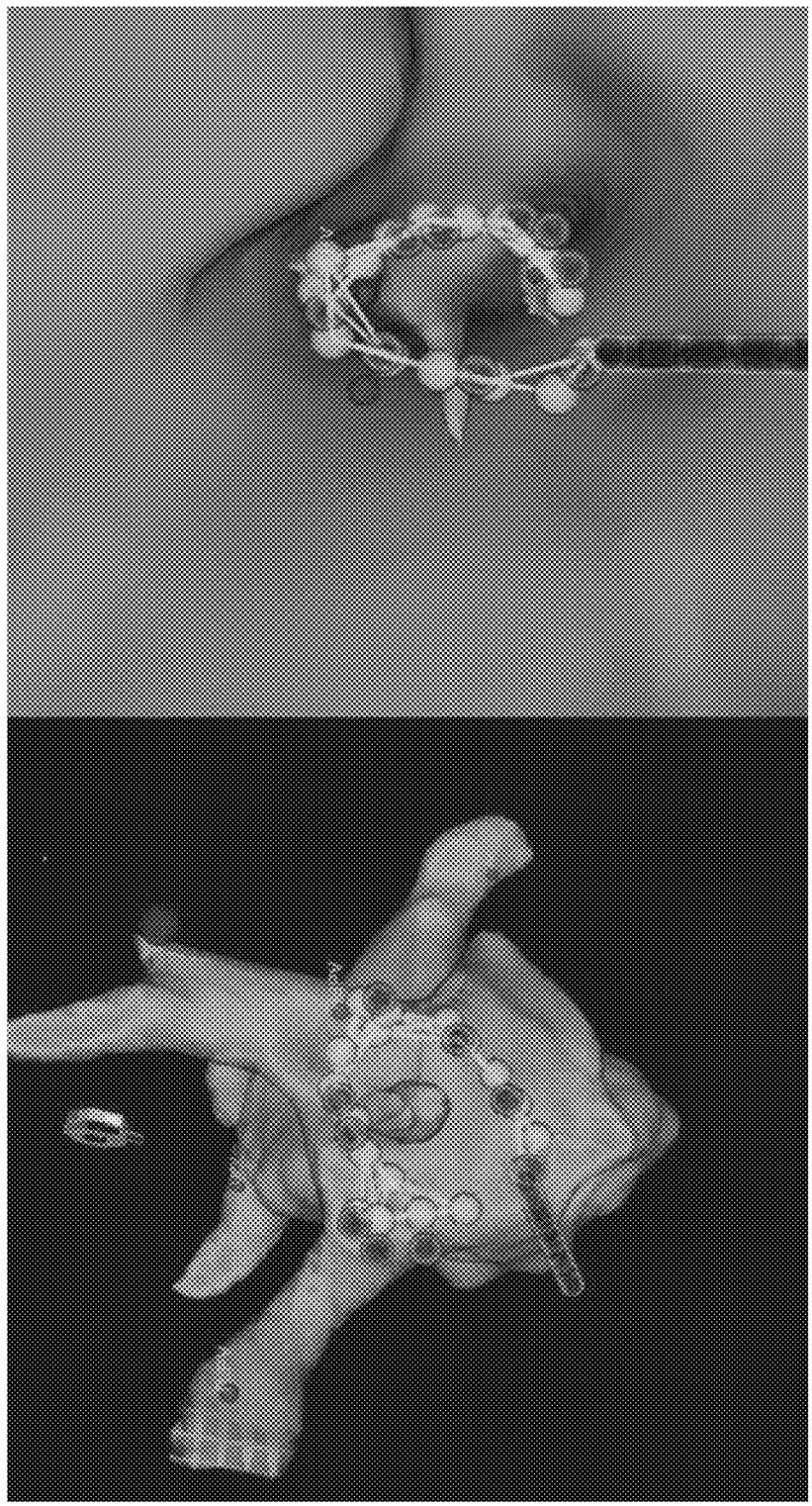
FIG. 15B schematically represents a visualization of results of an ablation segment effectiveness estimator applied to a plurality of ablation segment used in forming ablation lines within a left atrium, according to some embodiments of the present disclosure.

Reference is now made to FIG. 15A-15B, which schematically represents a visualization of results of an ablation segment effectiveness estimator applied to a plurality of ablation segment used in forming ablation lines within a left atrium, according to some embodiments of the present disclosure.

In some embodiments, the results are shown to a user and updated in real time as new ablation segments are formed. Green spheres (lightest gray spheres) represent sub-lesions and their sizes; segments drawn between these spheres represent ablation segments estimated to be effective. Blue spheres (darker spheres of same size as the lightest gray spheres, shown in FIG. 15B) represent currently planned sub-lesions in accordance with an ablation plan. Presenting both planned sub-lesions and actual sub-lesions may allow the user (physician) to better track the ablation procedure. An ablation probe is also shown in FIG. 15B. Small dark spheres anchor labels of anatomical landmarks such as the right inferior pulmonary vein (RIPV), right superior pulmonary vein (RSPV), atrial appendage (AA), and another pulmonary vein (PV).

In some embodiments, the ablation segments are displayed on an "unwrapped" and/or flattened 3-D display (for example: as shown in FIG. 15A) that allows simultaneous viewing of a large region of the heart chamber being treated. In FIG. 15A, the ring of light (green in color) circles represent ablations, and the dark line extending through a gap in the circles above the middle right of the right-hand ring of light circles comprises an indication that the ablation circle is estimated to remain incomplete.

Figure 16:
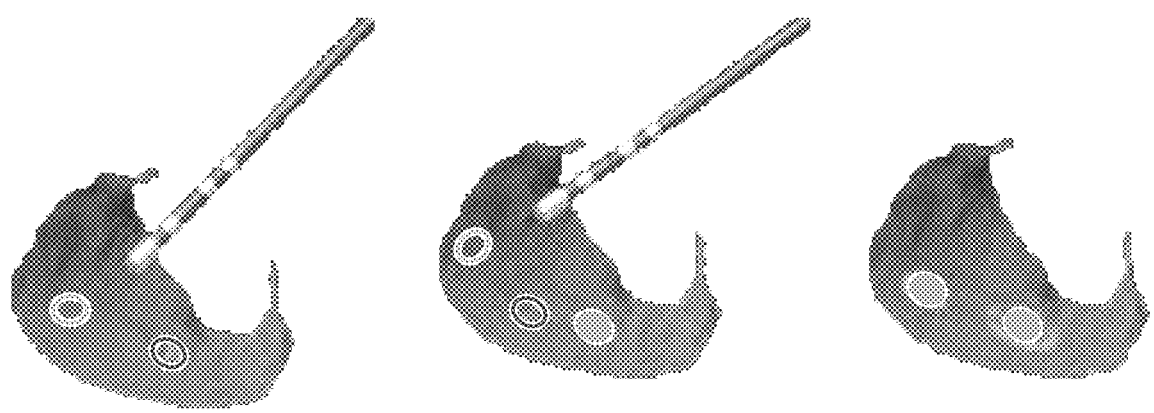
FIG. 16 schematically represents pairwise real-time lesion assessment based on use of an ablation segment effectiveness estimator, according to some embodiments of the present disclosure.

Reference is now made to FIG. 16, which schematically represents pairwise real-time lesion assessment based on use of an ablation segment effectiveness estimator, according to some embodiments of the present disclosure. In some embodiments, the images shown represent images displayed to a user in real time during an ablation procedure.

At left an ablation probe is shown navigating to a first sub-lesion target (e.g., the gray circle at right; blue if in color) in preparation for ablation to form the sub-lesion. The current surface region pointed to by the ablation probe is optionally marked, for example, by a circle (circle at left, red in color). Optionally, when the two circles come into alignment with the ablation probe contacting tissue, the ablation probe is optimally aligned for ablating.

At center, the ablation probe has ablated the sub-lesion, which is now shown in a lighter, filled shading (green, if shown in color). A new target is shown by a new position of an open circle in the middle, and the leftmost circle is again a pointed-at position. The ablation probe is again navigated to contact the region marked by the new open circle. During navigation, in some embodiments, a dotted line (or other indication, not shown) optionally indicates that the ablation segment which would potentially be formed from the indicated crossed circle is estimated to be ineffective (e.g., ineffective at creating impulse block). Optionally, the line indication changes when the probe is well-positioned to potentially create an effective block; e.g., it changes to a solid line.

At right, the second lesion has been formed (now also shown in a lighter color). If a connecting line is used, it would optionally remain, in this example, because the ablation segment effectiveness estimator would estimate (based on the large separation) that the two sub-lesions which now together define an ablation segment are insufficient to form an effective ablation segment. Optionally, the procedure continues by mitigating this situation, e.g., by further ablation directed to at least one of the existing sub-lesion locations, and/or by creation of one or more additional sub-lesions, e.g., an sub-lesion positioned between the first two sub-lesion.

Edema

Edema Time Course Simulation and Prediction

Figure 18:
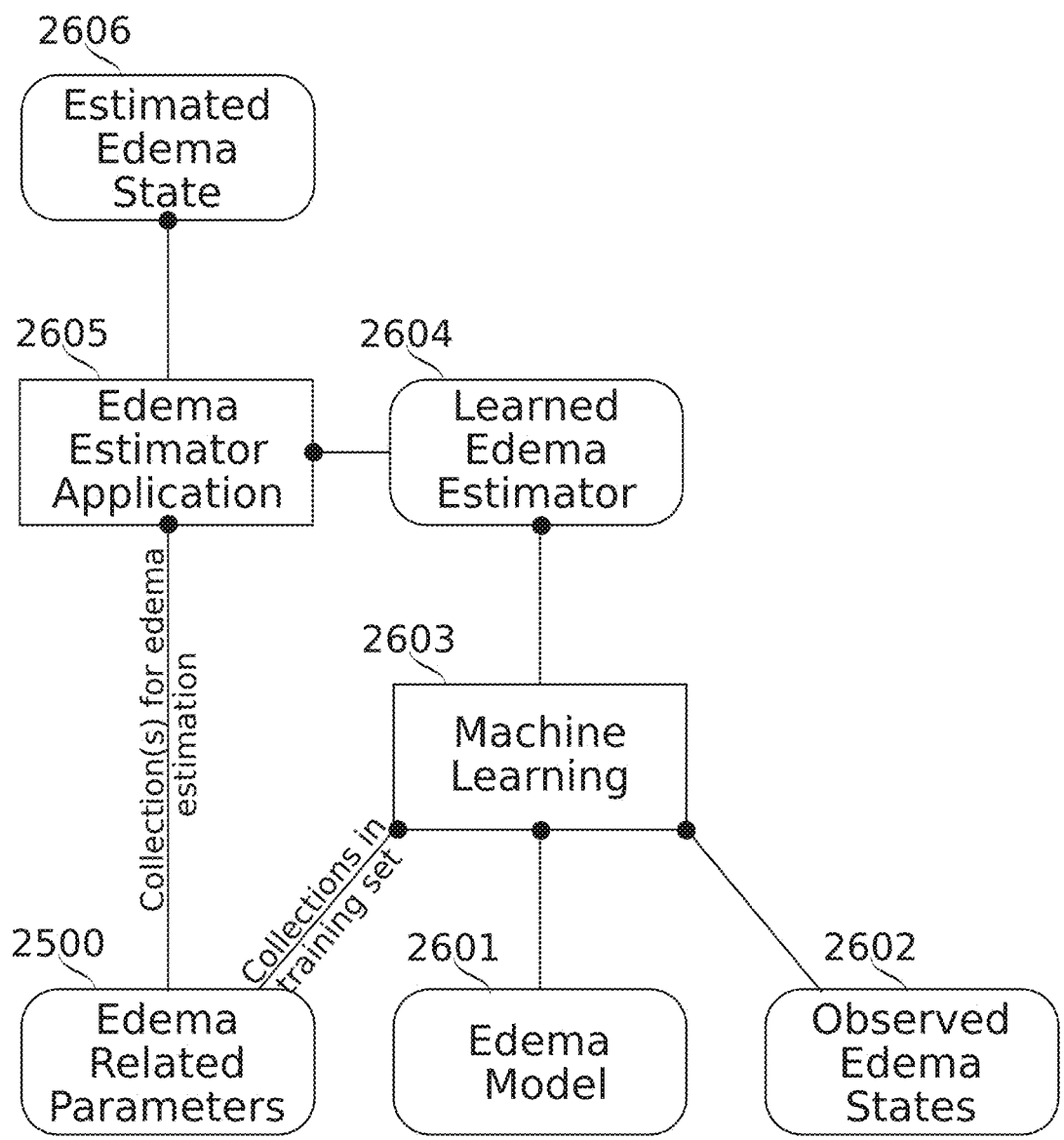
FIG. 18 is a schematic flowchart of a method of deriving and applying an elicited edema estimator for predicting edema, according to some embodiments of the present disclosure.

Reference is now made to FIG. 18 which is a schematic flowchart of a method of deriving and applying an elicited edema estimator for predicting edema, according to some embodiments of the present disclosure. First, inputs to and operation of machine learning at block 2603 are described. Then application of a learned elicited edema estimator 2604 at block 2605 is described (in FIG. 18 and other figures herein, "edema estimator" is also used to refer to an elicited edema estimator). Use is also made of the term "instance of edema", which refers to an actual, predicted, and/or simulated (as appropriate to the context) edematous tissue reaction following some particular eliciting stimulus such as operation of an ablation modality and/or mechanical contact. Optionally there can be more than one instance of edema developing in tissue at the same time, though elicited edema instances which come to overlap in area and/or time are optionally treated as parts of a single edematous scenario.

Prior Inputs to Machine Learning of an Edema Estimator

In some embodiments, the block marked 2500 in FIG. 18 comprises a plurality of "collections" of elicited edema parameters 2500. Sets of elicited edema parameters 2500 used, in some embodiments, and/or portions of such sets are also referred to herein as "input data" Each such collection in turn comprises a heterogeneous set of data inputs relating to one or more particular elicited edema instances. In some embodiments, the particular instance of edema is elicited (and/or is expected to be elicited) by the operation of an ablation modality (e.g., radio frequency ablation, cryoablation, microwave ablation, laser ablation, irreversible electroporation, substance injection ablation, and high-intensity focused ultrasound ablation) acting on tissue which is targeted for ablation or other medical treatment. In some embodiments, the instance of edema is elicited by mechanical contact between an intrabody probe (e.g. catheter probe) or other treatment modality and tissue.

The data inputs of a collection of elicited edema parameters 2500 include, for example, sub-lesion measurements made during and/or after sub-lesion ablation, placement of sub-lesions, ablation tool settings governing sub-lesion formation, calculated results of ablation, and/or tissue conditions within which the instance of edema is situated. In some embodiments, the data inputs comprise parameters describing force, and/or duration of mechanical contact.

Optionally, elicited edema parameters 2500 include other data; for example: patient data parameter, patient clinical data, and/or previously acquired ablation and/or mechanical contact data for the same patient. In some embodiments, parameters of elicited edema parameters 2500 include any suitable parameter described in connection with ablation segment effectiveness parameters 2100, for example, in reference to FIG. 14B herein and/or lesion effectiveness parameters 1500, for example, in reference to FIG. 4B herein. In some embodiments, raw measurements indicating edema (e.g., electrical field measurements such as dielectric measurements) may be used as elicited edema parameters 2500 (e.g., without any calculations) and may be input as training set data to edema estimator 2604.

The inputs of each collection of elicited edema parameters 2500 at least potentially indicate (individually and/or in aggregate) information about the initiation and/or time course of a particular instance of edema to which they relate.

At block 2603, in some embodiments, a plurality of collections of elicited edema parameters 2500 may be provided as a training set for use in one or more machine learning methods, in order to generate a learned elicited edema estimator 2604. The example of "machine learning" is used herein as an example of a method of creating an estimator, and should not be considered limiting. Alternatives include, for example general purpose statistical methods and/or estimator definition based on theoretical equations accounting for observed correlations. In some embodiments, training set data used in generating the learned elicited edema estimator 2604 are obtained at least in part in vivo. In some embodiments, at least part of the training set data used to generate the learned elicited edema estimator are obtained in vitro, for example based on ablation and/or mechanical stimulation of porcine heart wall.

Feedback Inputs to Machine Learning of an Edema Estimator

In some embodiments of the invention, for each collection of elicited edema parameters 2500 in the training set, there is also provided as input to block 2603 a corresponding data collection indicating observed edema states 2602. For example, the observed edema states optionally includes a measurement showing one or more of the following potential manifestations of edema: impedance and/or impedance dynamics, contact pressure, location of the eliciting stimulus (also referred to herein as a tissue "insult"), duration and/or power of the eliciting stimulus, lesion assessment or another tissue characteristic or any other parameter relating to an ablation operation which potentially also may manifest as edema.

In some embodiments, edema is observed by measurements of electrical signal through a tissue region, wherein there is no, attenuated, and/or dynamically attenuating electrical signal (e.g., reduction of electrical impulse transmitted across a pulmonary vein isolating ablation line comprising potentially edematous tissue), but this is not explained by full ablation (e.g., two ablations flanking the region of blocked transmission are apparently insufficiently close to comprise a permanent impulse blockade). Optionally, this measure of edema is confirmed by a later measurement (particularly for use in assembling a training set for use by machine learning 2603); for example, assessment of later recovery (or lack thereof), e.g., 1 month or more after edema was originally elicited.

In some embodiments, data indicating observed edema states are obtained by the same catheter that was used to form the ablation. For example, a probe of an RF ablation catheter is operated to ablate tissue, and then electrodes of the same catheter are used to measure potential electrical fields (e.g., high frequency electrical fields) induced in the vicinity of the ablation. From these measurements, impedance properties indicating edematous state are optionally calculated.

In some embodiments, the impedance properties in turn indicate dielectric properties of tissue that are changed as a result of tissue ablation. Dielectric properties and/or impedance are optionally interpreted as indicating local tissue state and in particular, local tissue state(s) as being permanently ablated (e.g., converted to fibrotic tissue), edematous but not fibrotic, and/or healthy. Data provided as a collection of observed edema states 2602 is optionally expressed in any suitable format; for example: voltages, impedances, dielectric properties, and/or tissue state(s) inferred therefrom. Optionally, another measure of observed edema states is provided, for example, imaging results, and/or direct thickness measurements (applicable in the case of in vitro experiments, for example).

In some embodiments dynamics of measurements such as impedance measurements are used. For example, impedance at an ablation region or region of mechanical contact is optionally set to a baseline before edema begins (e.g., before, during and/or immediately after ablation). During edema development, changes in impedance are measured (e.g., at frequencies up to about 1 MHz), and these changes optionally serve as input to an elicited edema estimator. The relevant dynamics are optionally provided in terms of magnitude, rate (slope and/or exponent, for example), and/or in terms of function shape, for example, linear, exponential, logarithmic or another shape.

In some embodiments, the impedance measurements include measurements of impedance between different electrodes on a probe of the ablation catheter or other probe (e.g., between a tip electrode of the ablation catheter and another electrode on the same catheter), between one or more electrodes on the ablation catheter and one or more electrodes on another catheter, and/or between one of more of the ablation electrodes and one or more body surface electrodes. In some embodiments, the impedance measurements include measurement of impedances at various frequencies, e.g., from about 10 kHz to about 1 MHz.

Optionally, estimated edema states 2606 are accompanied by a metric of certainty, for example, sensitivity and/or selectivity. In some embodiments, estimated edema states 2606 are displayed within an interactive user interface facilitating use by an operator to examine the estimate of edema, from different perspectives: for example, to check expected time course and/or distance of spread. In some embodiments, estimated edema states may be displayed as a map (to form an edema map, that is a representation of a surface showing positions of tissue which has entered a state of some degree of edema, optionally including representation of the degree of edema) on tissue regions, optionally as a function of current time any selected future time, or a combination of the two (e.g., an edema map optionally indicates both where edema is, and when and/or where it is currently expected to arise).

Model Input to an Edema Estimator

In some embodiments, the machine learning of block 2603 proceeds on the basis of an assumed model of edema 2601.

In some embodiments, sub-lesion modeling for the triggering of edema elicited by ablation is based on temperature modeling (for example combined EM and thermal modelling).

In some embodiments, parameters used in the temperature modeling include modeling of deformation of a contacted tissue region, e.g., in response to relative ablation probe angle and/or contact/pressure.

Other model parameters optionally include dielectric and/or thermal modeling of the body shape and internal organs including heart; as well as electrical energy transmission parameters of an ablation ground pad and electrodes of a catheter.

The model, in some embodiments, applies the EM and thermal model to simulate application of energy to an ablation area based on selected power, time, and/or EM frequency (e.g., around 460 kHz) parameters. Optionally, the EM and thermal model operates iteratively in time steps, e.g., of 100 msec, 250 msec, 500 msec, 1 sec, or another larger, smaller and/or intermediate time step. Simulated temperature changes result from power loss density conversion to thermal energy. In some embodiments, electrical properties which are themselves a function of temperature are also adjusted; for example, conductivity and relative permittivity. In some embodiments, changes to these properties are about 2%/° C. Optionally, thermal properties (e.g., specific heat and/or thermal conductivity) are also simulated.

Optionally, heated areas are divided into zones around the ablation region, based on temperature distribution. Each zone has a different geometry, evolving differently over time in temperature as result of different heat distributions, initial morphology (tip angled flat or perpendicular, for example) and/or tissue properties.

In some embodiments, a temperature range reached during ablation is used to distinguish fully ablated tissue from tissue which may go on to become edematous. For example, during ablation, tissue in a first zone (zone1) which reaches (and/or is modeled to reach under anticipated conditions of ablation) a temperature of at least 55° C. is optionally considered to be permanently non-conducting (and so, generally not in need or revisiting, whether or not it experiences some subsequent degree of edematous reaction).

Optionally, a distinction is made between two or more edema eliciting conditions experienced by tissue as the result of an ablation and/or mechanical contact. In some embodiments, the distinction is based on maximum temperature achieved during an ablation. For example, a zone (zone2) surrounding a permanently inactivated zone (e.g., reaching temperatures of 45° C.–55° C.) is distinguished from another zone (e.g., zone3, reaching temperatures of 40° C.–45° C.). Time courses and/or amplitudes of edema are optionally modeled with different constants for each of these two zones. Zone sizes are optionally determined by temperature modeling. Optionally, zone sizes are set by an empirically determined rule, e.g., the combined area of the two temperature zones has been found to be about twice as big as the corresponding size of the permanently ablated zone they arise with, and having the same general shape.

In some embodiments, zone1 and zone2 (or any other zone defined) are defined to differ from each other in one or more of edema lag time, rising phase time, and peak amplitude. The exact relative values chosen need not be exactly corresponding to actual edematous time courses, as they are often used to establish a "safety" function, within which ablation can proceed normally and with high chances of success, and outside of which, ablation requires adjustment of parameters, and/or the chances of success are lowered, Optionally, zone2 edema (the slower edema), is modeled to proceed with any of the time courses described herein above. Optionally, zone1 edema is faster than this in any suitable respect, for example, 10% faster, 20% faster, 30% faster, or faster by another larger, smaller, and/or intermediate fashion. Optionally, the fully developed amplitude of elicited edema is maximal within zone1 (e.g., full block complete prevention of further ablation), but smaller within zone2, unless added to by further ablations. For example, zone2 is optionally modeled as having reaching a maximum edema having half the power to temporarily block impulses and/or interfere with ablation as zone 1 reaches, or any other suitable ration such as 30%, 60%, 80%, or another larger, smaller, or intermediate number.

Over time (e.g., a month after ablation), the directly ablated zone has been observed in in vivo animal model preparations to tend to shrink by about 15%-20%, while zone2 and zone3 recover to their original thickness.

In some embodiments, more zones are defined. Optionally, edema eliciting conditions are modeled continuously, with corresponding continuous gradations in time course and/or amplitude constants.

Learned Edema Estimator

After the above-described inputs (observations of edema states 2602, parameters related to edema production 2500, and edema model 2601) are suitably defined and received for a plurality of elicited edema instances (e.g., 50, 100, 1000, or another larger, smaller, or intermediate number of elicited edema instances), machine learning at block 2603 uses of one or more machine learning methods, to produce a learned elicited edema estimator 2604. Examples of machine learning methods used in some embodiments of the present invention include, for example: decision tree learning, association rule learning, an artificial neural network, deep-learning artificial neural network, inductive logic programming, a support vector machine, cluster analysis, Bayesian networks, reinforcement learning, representation learning, similarity and metric learning, and/or another technique taken from the art of machine learning. Machine learning at block 2603 may be in accordance with techniques described in relation to machine learning 1603 and/or machine learning 2103.

In some embodiments, zones or other spatially characterized distributions of thermal initiation of edema are converted into expected time courses of edema development, e.g., time courses derived from machine learning (block 2603) of observed associations of elicited edema instances with elicited edema parameters. Use of machine learning, in some embodiments, comprises refinement of the basic model of edema described here, e.g., learning that assigns values adjusted from one or more of the default values described herein, based on particulars of the ablation scenario, in order to more accurately predict outcomes.

In some embodiments, this comprises assignment edematous time courses to tissue based one modeled temperature zone. Moreover, based on observations in the literature, an instance of edema may be expected to develop with a sigmoidal time course; i.e., initially slowly developing, followed by a rapid phase of edema development, leveling gradually off to a fully developed edematous state. A typical overall time course has been observed to be about 30 minutes to fully developed edema (e.g., ablation to at least 98% fully developed); optionally another total time course duration is used, for example, 20 minutes, 25 minutes 35 minutes, 40 minutes, or another larger, smaller and/or intermediate time. Optionally, termination of lag phase is defined with respect to a cutoff of about 10% of maximum amplitude, and termination of the rising phase defined with respect to a cutoff of about 90% of maximum amplitude. Optionally, constants of the sigmoid are set so that lag phase ends at about 1 minute 2 minutes after ablation, 3 minutes after ablation, 5 minutes after ablation 8 minutes after ablation, 10 minutes after ablation, or another longer, shorter or intermediate time after ablation. Optionally, lag phase is defined to begin the same number of minutes before the elapsing of about 30 minutes after ablation (or another rise-time). Lag phase and rising phase are optionally symmetrical in time. Optionally, they are asymmetrical (e.g., defined to have different termination/onset times respectively, relative to time from the 50% amplitude point of rising phase) The amplitude may be considered to rise from 0 to 1, wherein 1 is a state of complete edema. Optionally, amplitude is expressed in terms of effects (and/or maximum effects of edema referenced to current edema state, e.g., by multiplication), e.g., how much more power and/or time should be used to ablate in the edematous region successfully, last time post-ablation that ablation should be attempted without revision of an ablation plan, etc. Optionally, a physician can set any desired threshold or other function for these effects, based on their own preferences (which may be based on their own style of ablation, tolerance for uncertainty of result in the estimator output, assessment of patient risk, etc.), Calibration of time course of edema, and/or effects of edema on estimators or other uses of edema estimators which may use them, can be done by use of a test ablation with a subject (e.g., maximum edema is correlated to same-patient observations of ablation power absorption, etc.), avoiding a need for undue experimentation.

In some embodiments, predictions of edema include such observations in the assumptions of model of edema 2601, used to structure machine learning 2603. Sigmoidal constants are optionally defined to vary over the surface of a tissue extending away from the region of initial insult, e.g., according to temperature zone. Optionally, time course parameters vary with tissue depth.

Any suitable number of constants are optionally used to express observed edema time courses, e.g., one for amplitude and at least one more for dynamics (e.g., optionally, lag, rise, and leveling off are each separately assigned parameters; alternatively, two or more of these are optionally described by a shared parameter) The time course of edema development (e.g., constants of a sigmoidal functioning describing edema development) is optionally variable for different tissue regions, different patients, and/or different states of the same patient. Edema time course can also vary depending on the degree of insult that elicits it; for example, duration and power of ablation, maximum temperature reached (e.g., as just described) and/or contact pressure. In some embodiments, edema time course for a patient is calibrated based on measurements of actual edematous response to lesions made. Optionally, calibration is based on any partial or complete edema response (e.g., edema observed up to the end of a lag period, edema observed during the rapid rising phase, and/or edema observed during a levelling-off period). Optionally, an ablation "test lesion" is made at some isolated portion of the heart wall, and periodically observed. Optionally, any sub-lesion an ablation line (e.g., an initial sub-lesion) is measured for calibration. Optionally, calibrations are performed per region, and/or per region type (e.g, separately for thicker and thinner heart wall regions).

In some embodiments, the learned elicited edema estimator 2604 comprises a set of learned weights applied to terms of model of edema 2601, an equation, or an elicited edema estimator function in another suitable form. Application of the edema estimate at block 2605, in some embodiments, comprises plugging into the model appropriate values from a collection of elicited edema parameters 2500 for some new instance of edema, and calculating the result. The result is produced as an estimated edema state 2606, applied to an affected region of tissue, and optionally evolving over time for each particular instance of edema.

In some embodiments, estimated edema states 2606 are separately determined for a plurality of instance of edema time courses, which are optionally at least partially overlapping in space and time. Optionally, edema response for a particular region is according to the worst-case (largest/fastest edema) for any potentially contributing instance of edema. In some embodiments, effects are additive, optionally additive with a suitable adjustment (e.g., proportional decreases in additive amplitude) for a maximum-limited state of edema.

In some embodiments, estimated tissue state for a period after resolution of edema is also calculated from based on the elicited edema instances result, for example, by reverting the electrical properties of zone2 and zone3 to their pre-ablation states, while continuing to model zone1 as irreversibly ablated. Optionally, zone1 is further modified from an initial value (e.g., as initially reconstructed from a CT image) to reflect shrinkage (e.g., shrinkage of 15-20%).

In some embodiments, results of the immediate, time-evolving estimated edema state 2606 and/or estimated long-term state modeling are used as inputs to another estimator, for example, an ablation segment effectiveness estimator as described in relation to FIG. 14A, or another estimator, for example, a lesion estimator as described in relation to FIG. 1B or ablation line estimator as described in relation to FIG. 6.

In some embodiments, an elicited edema estimator and/or another estimator applied to a sequence of sub-lesions and/or ablation segments is used to assist a physician in defining a line of planned ablations; for example, optimizing the line of planned ablations to a minimal length and/or minimal number of ablation needed to isolate one or more features such as vein roots which a preliminary line of planned ablation surrounds, and/or which another indication by the physician otherwise delineates, indicates, and/or selects.

In some embodiments, results of the immediate, time-evolving estimated edema state 2606 and/or estimated long-term state modeling are used as inputs to another estimator or computer hardware for planning an ablation path, e.g., an optimal ablation path according to one or more criteria. Such computer hardware and/or methods are also described for example, in International Patent Publication No. WO2016/181317; the contents of which are included herein by reference in their entirety.

In some embodiments, results of the immediate, time-evolving estimated edema state 2606 and/or estimated long-term state modeling are used as inputs to another estimator or computer hardware for adjusting a pre-planned an ablation path, e.g., it may be used to add or reduce ablation points (or segments). Optionally, such adjusting is performed on-line during treatment.

In some embodiments, edema map is used as input to another estimator or computer hardware for planning and/or adjusting an ablation path. Optionally, such adjusting is performed on-line during treatment.

In another example, an initially proposed ablation path optionally defines 60 planned ablation regions (sub-lesions).

Upon suitable application of an elicited edema estimator and/or ablation segment effectiveness estimator to the purpose, a system optionally reports whether or not the path as defined will create a closed ablation line. The system optionally also advises if there is a shorter and/or simpler ablation line which could successfully create a similarly effective closed ablation line, for example, using only a sub-group of 40 ablation regions. Optionally, the system advises if there are additional ablation regions that should be added for a higher likelihood of ablation line closure.

Potentially, this saves ablating (and/or re-ablating) regions which are not required, and/or strengthens ablation segments which require additional ablation, for example by reducing distance between ablation regions. Optionally, such revision is performed on-line during treatment, e.g., in response to actual positions of sub-lesions.

Physiological Simulation—Example of Display of Edema Simulation Results

Reference is now made to FIGS. 17A-17D, which schematically represent indicating changes to the display of a rendered tissue region 2050 due to predicted and/or measured edema, according to some embodiments of the present disclosure.

In some embodiments, edema development (predicted and/or measured) is shown to an operator (e.g., a physician) in real time, during performing of a procedure such as ablation procedure, or another procedure liable to elicit edema. In some embodiments, edema development (predicted and/or measured) is shown to an operator (e.g., a physician) in real time in a form of edema map.

A potential advantage of real time prediction and/or display of edema development is that it may encourage an operator to ablate faster (e.g., at higher power) when edema is seen to and/or predicted to develop quickly.

Real time prediction and/or display of edema development potentially also guides a physician in the choice of ablation parameters. E.g., if edema from a preceding sub-lesion moves fast towards another targeted region for sub-lesion placement, an operator may change parameters to achieve full ablation faster, change the direction of the catheter, etc.

Optionally, an edema map assists an operator in choosing a next placement of a sub-lesion. Optionally, given a planned placement for a sub-lesion, an edema map assists in setting ablation parameters. In some embodiments, the system itself calculates and suggests a next sub-lesion placement and/or ablation parameters based in part on the edema map.

Figure 17A:
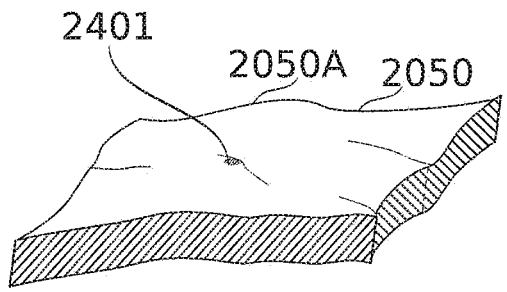
FIGS. 17A-17D schematically represent indicating changes to the display of a rendered tissue region due to predicted and/or measured edema, according to some embodiments of the present disclosure.
Figure 17B:
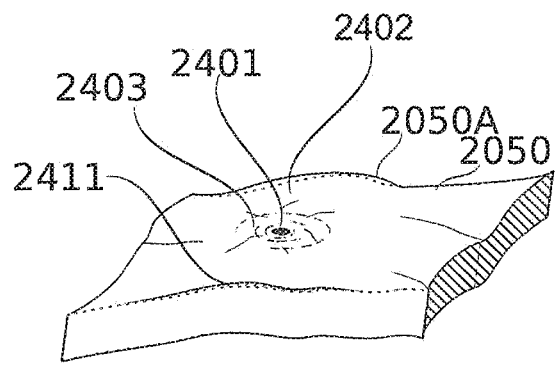
Figure 17C:
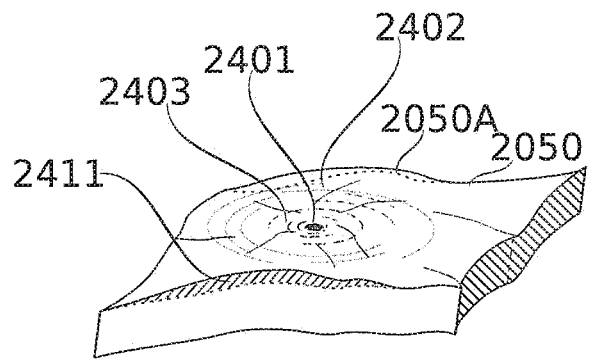
Figure 17D:
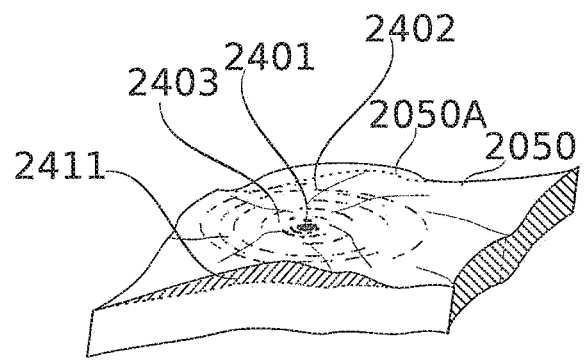

In FIG. 17A, lesion 2401 represents a recently formed lesion, for example, an RF ablation lesion. Over the course of a few minutes after RF ablation, tissue potentially reacts with an edematous swelling response. Optionally, edema is elicited by another even during a procedure, for example, mechanical contacts between a catheter and a tissue surface.

In some embodiments of the invention, the swelling response is simulated (for example, as a function of time, and/or based on measurements such as dielectric and/or impedance measurements that provide edema data) by one or both of increasing thickness in a region 2403 surrounding lesion 2401, and a change in color and/or texture in region 2402 (represented by the partial rings in the drawing). Thickness changes can also be seen in the changing (increasing) thickness of region 2411 between FIGS. 17B-17D; comparison also can be made to the baseline surface boundary 2050A.

In some embodiments, another representation of edema is used additionally and/or alternatively, for example, changes in color, texture, or another visual feature.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention.

Certain features described in the context of various embodiments are not to be considered essential features of those embodiments, unless the embodiment is inoperative without those elements.

What is claimed is:

1. A method of estimating effectiveness of ablation to form a lesion, the method comprising:
    receiving lesion effectiveness parameters including parameters indicative of the conditions of formation and/or structure of the ablation lesion in the tissue and measurements of pre-lesioning condition of the tissue;
    estimating an effectiveness of the ablation lesion in the tissue based upon applying received lesion effectiveness parameters to an estimator, wherein the estimator is constructed by computer circuitry and is based upon observed association between previously analyzed lesion effectiveness parameters and observed lesion effectiveness stored data; and
    proceeding or completing an ablation treatment procedure of the tissue based upon an output of the estimation of the effectiveness of the ablation lesion.

2. The method of claim 1, wherein the lesion effectiveness parameters further include patient parameter data and parameters of the ablation treatment procedure of the tissue.

3. The method of claim 2, wherein said estimator is constructed by machine learning methods.

4. The method of claim 1, wherein the pre-lesioning condition of the tissue is tissue thickness, fiber orientation, tissue types and/or dielectric measurements.

5. The method of claim 4, wherein the pre-lesioning condition of the tissue is selected from the group consisting of tissue thickness, determined from dielectric measurements measured by an ablation catheter used to produce the lesion.

6. The method of claim 1, wherein the conditions of formation of the ablation lesion is ablation power, dielectric quality of contact, angle of contact, force of contact and/or timing of ablation.

7. The method of claim 1, wherein the structure of the ablation lesion is indicated by a measure of the depth, size and/or volume of the ablation lesion.

8. The method of claim 1, wherein the step of receiving and estimating are performed during the ablation of the tissue.

9. The method of claim 1, wherein the method further comprises adjusting a plan of ablation treatment based on the output of the estimation of the effectiveness of the ablation lesion.

10. The method of claim 1, wherein the ablation lesion comprises a lesion formed by a single event of applying ablation energy to a focal region of the tissue.

11. The method of claim 1, wherein the step of proceeding or completing the ablation of the tissue is based upon comparing the output of the estimation of the effectiveness of the ablation lesion with one or more criteria of effectiveness.

12. The method of claim 11, wherein the one or more criteria of effectiveness comprises successful electrical isolation of electrical impulses.

13. A method of estimating effectiveness of ablation to form an ablation line, the method comprising:
    receiving ablation line effectiveness parameters including parameters indicative of the conditions of formation and/or structure of the ablation line in the tissue and measurements of pre-lesioning condition of the tissue; and
    estimating an effectiveness of the ablation line in the tissue based upon applying the received line effectiveness parameters to an estimator, wherein the estimator is constructed by a computer circuitry and is based upon observed association between previously analyzed ablation line effectiveness parameters and observed ablation line effectiveness stored data; and
    proceeding or completing an ablation treatment procedure of the tissue based upon an output of the estimation of the effectiveness of the ablation line.

14. The method of claim 13, wherein the ablation line effectiveness parameters further include patient parameter data and procedural parameters of the ablation treatment procedure of the tissue.

15. The method of claim 14, wherein said estimator is constructed by machine learning methods.

16. The method of claim 13, wherein the pre-lesioning condition of the tissue is selected from the group consisting of tissue thickness, fiber orientation, tissue types and/or dielectric measurements.

17. The method of claim 16, wherein a lesion of the ablation line comprises a lesion formed by a single event of applying ablation energy to a focal region of the tissue.

18. The method of claim 13, wherein the conditions of formation of the ablation line is selected from the group consisting of ablation power, dielectric quality of contact, angle of contact, force of contact and/or timing of ablation.

19. The method of claim 13, wherein the structure of the ablation line is indicated by a measure of the depth, size and/or volume of a lesion of the ablation line.

20. The method of claim 13, wherein the steps of receiving and estimating are performed during the ablation of the tissue.

21. The method of claim 13, wherein the method further comprises adjusting a plan of ablation treatment based on the output of the estimation of the effectiveness of the ablation line.

22. The method of claim 13, wherein the step of proceeding or completing the ablation of the tissue is based upon comparing the output of the estimation of the effectiveness of the ablation line with one or more criteria of effectiveness, wherein the one or more criteria of effectiveness comprises successful electrical isolation of electrical impulses across the ablation line.

23. A method of estimating effectiveness of ablation to form an ablation segment, the method comprising:
receiving ablation segment effectiveness parameters including parameters indicative of the conditions of formation and/or structure of the ablation segment in the tissue and measurements of pre-lesioning condition of the tissue; and
constructing an estimator, by computer circuitry, based upon observed associations between previously analyzed ablation segment effectiveness parameters and observed ablation segment effectiveness stored data;
estimating an effectiveness of the ablation segment in the tissue based upon applying the received segment effectiveness parameters to the estimator, wherein the estimator is constructed by a computer circuitry and is based upon observed association between previously analyzed ablation segment effectiveness parameters and observed ablation segment effectiveness stored data; and
proceeding or completing an ablation treatment procedure of the tissue based upon an output of the estimation of the effectiveness of the ablation segment.

24. The method of claim 23, wherein the ablation segment effectiveness parameters further include patient parameter data and procedural parameters of the ablation treatment procedure of the tissue.

25. The method of claim 24, wherein said estimator is constructed by machine learning methods.

26. The method of claim 23, wherein the pre-lesioning condition of the tissue is selected from the group consisting of tissue thickness, fiber orientation, tissue types and/or dielectric measurements.

27. The method of claim 23, wherein the conditions of formation of the ablation segment is selected from the group consisting of ablation power, dielectric quality of contact, angle of contact, force of contact and/or timing of ablation.

28. The method of claim 23, wherein the structure of the ablation segment is indicated by a measure of the depth, size and/or volume of a lesion of the ablation segment.

29. The method of claim 23, wherein the steps of receiving and estimating are performed during the ablation of the tissue.

30. The method of claim 23, wherein the method further comprises adjusting a plan of ablation treatment based on the output of the estimation of the effectiveness of the ablation segment.

31. The method of claim 23, wherein a lesion of the ablation segment comprises a lesion formed by a single event of applying ablation energy to a focal region of the tissue.

32. The method of claim 23, wherein the step of proceeding or completing the ablation of the tissue is based upon comparing the output of the estimation of the effectiveness of the ablation segment with one or more criteria of effectiveness, wherein the one or more criteria of effectiveness comprises successful electrical isolation of electrical impulses across the ablation segment.

33. A method of estimating effectiveness of ablation to form an ablation, the method comprising:
receiving ablation effectiveness parameters including parameters indicative of the conditions used in forming the ablation and/or structure of a created ablation in the tissue, after an ablation treatment to achieve a clinical result and measurements of pre-lesioning condition of the tissue;
estimating an effectiveness of the ablation in the tissue based upon applying the received effectiveness parameters to the estimator, wherein the estimator is constructed by computer circuitry and is based upon observed associations between previously analyzed ablation effectiveness parameters and observed ablation effectiveness on clinical results; and
proceeding or completing an ablation treatment procedure of the tissue based upon an output of the estimation of the effectiveness of the ablation.

* * * * *